United States Patent
Tiebes et al.

(10) Patent No.: US 6,521,610 B2
(45) Date of Patent: *Feb. 18, 2003

(54) 4-HALOALKYL-3-HETEROCYCLYLPYRIDINES AND 4-HALOALKYL-5-HETEROCYCLYL-PYRIMIDINES, PROCESSES FOR THEIR PREPARATION, COMPOSITIONS COMPRISING THEM, AND THEIR USE AS PESTICIDES

(75) Inventors: Jörg Tiebes, Offenbach (DE); Thomas Taapken, Frankfurt (DE); Burkhard Rook, Selters (DE); Manfred Kern, Lörzweiler (DE); Ulrich Sanft, Hofheim (DE)

(73) Assignee: Hoechst Schering AgrEvo GmbH, Frankfurt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/808,194

(22) Filed: Mar. 14, 2001

(65) Prior Publication Data
US 2002/0013326 A1 Jan. 31, 2002

Related U.S. Application Data

(62) Division of application No. 09/096,748, filed on Jun. 12, 1998, now Pat. No. 6,239,160.

(30) Foreign Application Priority Data

Jun. 16, 1997 (DE) .......................................... 197 25 450

(51) Int. Cl.[7] ...................... A61K 31/33; A61K 31/505; C07D 239/02
(52) U.S. Cl. ...................... 514/183; 514/256; 544/242; 544/333; 544/335
(58) Field of Search ...................... 514/183, 256; 544/242, 333, 335

(56) References Cited

U.S. PATENT DOCUMENTS

| | | | |
|---|---|---|---|
| 4,788,210 A | 11/1988 | Luthy et al. | 514/383 |
| 5,571,815 A | 11/1996 | Schaper et al. | 514/269 |
| 5,633,267 A | 5/1997 | Heinemann et al. | 514/342 |
| 5,723,450 A | 3/1998 | Reuschling et al. | 514/63 |

FOREIGN PATENT DOCUMENTS

| | | |
|---|---|---|
| DE | 2 127 404 A | 4/1984 |
| DE | 42 39 727 A1 | 6/1994 |
| EP | 0185256 A2 | 6/1986 |
| EP | 0 185 256 B1 | 6/1986 |
| EP | 0 357 241 A1 | 3/1990 |
| EP | 371925 * | 6/1990 |
| EP | 0371925 A2 | 6/1990 |
| WO | WO 93/19050 | 9/1993 |
| WO | WO 95/07891 | 3/1995 |

OTHER PUBLICATIONS

Maybridge Catalog 1996/1997 (Maybridge Chemical Company, Ltd.).

* cited by examiner

Primary Examiner—Mukund J. Shah
Assistant Examiner—Sudhaker B. Patel
(74) Attorney, Agent, or Firm—Frommer Lawrence & Haug LLP

(57) ABSTRACT

4-Haloalkyl-3-heterocyclylpyridines and 4-haloalkyl-5-heterocyclyl-pyrimidines, processes for their preparation, compositions comprising them, and their use as pesticides The present invention relates to 4-haloalkyl-3-heterocyclylpyridines and 4-haloalkyl-5-heterocyclylpyrimidines of the formula (I), to processes for their preparation, to compositions comprising them, and to the use of these compounds for controlling animal pests, in particular insects, spider mites, ectoparasites and helminths.

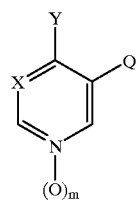

(I)

In the formula (I), Q is a 5-membered heterocyclic group which is optionally substituted by halogen or organic radicals, Y is halo-$C_1$–$C_6$–alkyl, X is CH or N and m is 0 or 1.

12 Claims, No Drawings

4-HALOALKYL-3-HETEROCYCLYLPYRIDINES AND 4-HALOALKYL-5-HETEROCYCLYL-PYRIMIDINES, PROCESSES FOR THEIR PREPARATION, COMPOSITIONS COMPRISING THEM, AND THEIR USE AS PESTICIDES

This application is a divisional of application U.S. Ser. No. 09/096,748, filed on Jun. 12, 1998, now U.S. Pat. No. 6,239,160, which claims priority to German application 197 25 450.0, filed Jun. 16, 1997.

DESCRIPTION

The present invention relates to 4-haloalkyl-3-heterocyclylpyridines and 4-haloalkyl-5-heterocyclylpyrimidines, to processes for their preparation, to compositions comprising them and to the use of novel and known 4-haloalkyl-3-heterocyclylpyridines and 4-haloalkyl-5-heterocyclylpyrimidines for controlling animal pests, in particular insects, spider mites, ectoparasites and helminths.

It is already known that appropriately substituted pyridines or pyrimidines have acaricidal and insecticidal activity. Thus, WO 95/07891 describes pyridines which carry a cycloalkyl radical in position 4 which is linked via a hetero atom and a group of various substituents in position 3. WO 93119050 discloses 4-cycloalkylamino-and 4-cycloalkoxypyrimidines which carry in position 5 inter alia alkyl, alkoxy or haloalkoxy groups. However, the desired activity against the harmful organisms is not always sufficient. Additionally, these compounds often have undesirable toxicologic properties toward mammals and aquatic living beings.

Pyridyl-1,2,4-thiadiazoles having fungicidal properties are described in DE-A 42 39 727. The compounds disclosed therein carry the thiadiazole ring in position 2, 3 or 4 of the unsubstituted pyridine.

EP-A 0 371 925 discloses some 1,3,4-oxadiazolyl- and 1,3,4-thiadiazolyl-pyrimidines having nematicidal and fungicidal properties. In the biologically effective compounds disclosed in this publication, the pyrimidine carries the oxadiazolyl or thiadiazolyl ring either a) in position 5 and is optionally substituted by a thiomethyl group in position 2, or b) in position 2 and is optionally substituted in position 4 and 6, in each case by a methyl group.

Aryltriazole derivatives for use as pesticides are known from EP-A 0,185,256. In addition to the phenyltriazoles, which are particularly preferred, three haloalkyl-3-pyridyltriazoles are disclosed:

3-(2-chlorophenyl)-1-methyl-5-(4-trifluoromethyl-3-pyridyl)-1H-1,2,4-triazole 3-(2,6-difluorophenyl)-1-methyl-5-(4-trifluoromethyl-3-pyridyl)-1H-1,2,4-triazole and 3-(2-chloro4-fluorophenyl)-1-methyl-5-(4-trifluoromethyl-3-pyridyl)-1H-1,2,4-triazole, their desired activity at low application rates, however, is not always satisfactory, especially when controlling insects and spider mites.

Some commercially available 4-haloalkyl-3-heterocyclylpyridines are known from the Maybridge Catalogue 1996/1997, Maybridge Chemical CO. LTD., Trevillett Tintagel, GB:

3-(3,5-dichlorophenyl)-5-(4-trifluoromethyl-3-pyridyl)-1,2,4-oxadiazole 5-(4-trifluoromethyl-3-pyridyl)-3-phenyl-1,2,4-oxadiazole 3-(4-trifluoromethyl-3-pyridyl)-5-phenyl-1,2,4-oxadiazole 5-(2-chlorophenyl)-3-(4-trifluoromethyl-3-pyridyl)-1,2,4-oxadiazole 5-(3-chlorophenyl)-3-(4-trifluoromethyl-3-pyridyl)-1,2,4-oxadiazole 5-(4-chlorophenyl)-3-(4-trifluoromethyl-3-pyridyl)-1,2,4oxadiazole 5-(2-fluorophenyl)-3-(4-trifluoromethyl-3-pyridyl)-1,2,4-oxadiazole 5-(4-fluorophenyl)-3-(4-trifluoromethyl-3-pyridyl)-1,2,4-oxadiazole 5-(2,4-dichlorophenyl)-3-(4-trifluoromethyl-3-pyridyl)-1,2,4-oxadiazole 5-(3,4-dichlorophenyl)-3-(4-trifluoromethyl-3-pyridyl)-1,2,4-oxadiazole 5-(3,5-dichlorophenyl)-3-(4-trifluoromethyl-3-pyridyl)-1,2,4-oxadiazole 5-(2,6-dichloro-4-pyridyl)-3-(4-trifluoromethyl-3-pyridyl)-1,2,4-oxadiazole 5-(3,5-bistrifluoromethylphenyl)-3-(4-trifluoromethyl-3-pyridyl)-1,2,4-oxadiazole 2-(2-chlorophenyl)-5-(4-trifluoromethyl-3-pyridyl)-1,3,4-oxadiazole 2-(3-chlorophenyl)-5-(4-trifluoromethyl-3-pyridyl)-1,3,4-oxadiazole 2-(4-chlorophenyl)-5-(4-trifluoromethyl-3-pyridyl)-1,3,4-oxadiazole 2-(2-trifluoromethoxyphenyl)-5-(4-trifluoromethyl-3-pyridyl)-1,3,4-oxadiazole 2-(4-trifluoromethoxyphenyl)-5-(4-trifluoromethyl-3-pyridyl)-1,3,4-oxadiazole 2-(4-trifluoromethyl-3-pyridyl)-5-phenyl-1,3,4-oxadiazole 2-(4-trifluoromethyl-3-pyridyl)-4-methylthiazolecarbohydrazide ethyl 2-(4-trifluoromethyl-3-pyridyl)-4-methylthiazolecarboxylate N-(4-chlorophenyl)carbonyl-N'-[2-(4-trifluoromethyl-3-pyridyl)4-methyl-5-thiazolyl]carbonylhydrazine 2-(4-trifluoromethyl-3-pyridyl)-4-thiazolecarbohydrazide 4-(4-chlorophenyl)-2-(4-trifluoromethyl-3-pyridyl)thiazole 4-(4-cyanophenyl)-2-(4-trifluoromethyl-3-py(idyl)thiazole N-(4-trifluoromethylphenyl)carbonyl-N'-[2-(4-trifluoromethyl-3-pyridyl)-4-thiazolyl]carbonylhydrazine 2-(2-(4-trifluoromethyl-3-pyridyl)thiazolyl)-5-chloro-3-methylbenzo[b]thiophene 2-(4-chlorophenylmethylthio)-5-(4-trifluoromethyl-3-pyridyl)-1 -methyl-1 H-1,3,4-triazole 2-(4-chlorophenylcarbonylmethylthio)-5-(4-trifluoromethyl-3-pyridyl)-1-methyl-1H-1,3,4-triazole and 2-ethoxycarbonylmethylthio-5-(4-trifluoromethyl-3-pyridyl)-1-methyl-1H-1,3,4-triazole.

However, a biological activity toward harmful organisms has hitherto not been disclosed.

It is an object of the present invention to provide compounds having good insecticidal and acaricidal properties and simultaneously low toxicity toward mammals and aquatic living beings.

It has now been found that compounds of the formula I, optionally as salts, have a wider activity spectrum against animal pests and simultaneously more favorable toxicologic properties toward mammals and aquatic living beings than the prior art compounds.

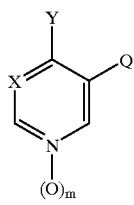

(I)

In the formula (I):
Y is halo-$C_1$–$C_6$–alkyl;
x is CH or N;
m is 0 or 1;
Q is a 5-membered heterocyclic group

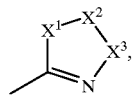

in which

| | | | |
|---|---|---|---|
| a) $X^1$ = W, | $X^2$ = $NR^a$, | $X^3$ = $CR^bR^1$ | or |
| b) $X^1$ = $NR^a$, | $X^2$ = $CR^bR^1$, | $X^3$ = W | or |
| c) $X^1$ = V, | $X^2$ = $CR^aR^1$, | $X^3$ = $NR^b$ | or |
| d) $X^1$ = V, | $X^2$ = $CR^aR^2$, | $X^3$ = $CR^bR^3$ | or |
| e) $X^1$ = V, | $X^2$ = $CR^4R^5$, | $X^3$ = $CR^6R^7$ | or |
| f) $X^1$ = $NR^a$, | $X^2$ = $CR^bR^1$, | $X^3$ = $NR^8$; | |

$R^a$ and $R^b$ together are a bond
V is oxygen, sulfur or $NR^9$;
W is oxygen or sulfur;
$R^1$ is hydrogen,
($C_1$–$C_{20}$)-alkyl, ($C_2$–$C_{20}$)-alkenyl, ($C_2$–$C_{20}$)-alkynyl, ($C_3$–$C_8$)-cycloalkyl,
($C_4$–$C_8$)-cycloalkenyl, ($C_6$–$C_8$)-cycloalkynyl,
where the six last-mentioned radicals are optionally substituted by one or more radicals from the group
halogen, cyano, nitro, hydroxyl, —C(=W)$R^{10}$, —C(=NO$R^{10}$)$R^{10}$, —(=NN$R^{10}_2$)$R^{10}$, —C(=W)O$R^{10}$, —C(=W)N$R^{10}_2$, —OC(=W)$R^{10}$, —OC(=W)O$R^{10}$, —N$R^{10}$C(=W)$R^{10}$, —N[C(=W)$R^{10}$]$_2$, —N$R^{10}$C(=W) O$R^{10}$, —C(=W)N$R^{10}$—N$R^{10}$C(=W)N$R^{10}$—N$R^{10}$[C (=W)$R^{10}$], —N$R^{10}$—C(=W)N$R^{10}_2$, —N$R^{10}$—N$R^{10}$C (=W)$R^{10}$, —N$R^{10}$—N[C(=W)$R^{10}$]$_2$, —N[(C=W)$R^{10}$]— N$R^{10}_2$, —N$R^{10}$—N$R^{10}$[(C=W)$R^{10}$], —N$R^{10}$—N$R^{10}$ [(C=W)W$R^{10}$], —N$R^{10}$—$R^{10}$[(C=W)N$R^{10}_2$], —N$R^{10}$ (C=N$R^{10}$)$R^{10}$, —N$R^{10}$(C=N$R^{10}$)N$R^{10}_2$, —O—N$R^{10}_2$, —O—N$R^{10}$(C=W)$R^{10}$, —SO$_2$N$R^{10}_2$, —N$R^{10}$SO$_2$$R^{10}$, —SO$_2$O$R^{10}$, —OSO$_2$$R^{10}$—O$R^{10}$, —N$R^{10}_2$, —S$R^{10}$, —SiR$^{10}_3$, —SeR$^{10}$, —P$R^{10}_2$, —P(=W)$R^{10}_2$, —SO$R^{10}$, —SO$_2$$R^{10}$, —PW$_2$$R^{10}_2$, —PW$_3$$R^{10}_2$, aryl and heterocyclyl, the two last-mentioned radicals optionally being substituted by one or more radicals from the group
($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_6$–$C_8$)-cycloalkynyl, ($C_1$–$C_6$)-haloalkyl, ($C_2$–$C_6$)-haloalkenyl, ($C_2$–$C_6$)-haloalkynyl, halogen, —O$R^{10}$, —N$R^{10}_2$, —S$R^{10}$, —SiR$^{10}_3$, —C(=W)$R^{10}$, —C(=W)O$R^{10}$, —C(=W) N$R^{10}_2$, —SO$R^{10}$, —SO$_2$$R^{10}$, nitro, cyano and hydroxyl, aryl,
which is optionally substituted by one or more radicals from the group ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl,
where these six abovementioned radicals are optionally substituted by one or more radicals from the group
halogen, cyano, nitro, —C(=W)$R^{10}$, —C(=W)O$R^{10}$, —C(=W)N$R^{10}_2$, —O$R^{10}$, —N$R^{10}_2$, —S$R^{10}$, —SO$R^{10}$ and —SO$_2$$R^{10}$,
halogen, cyano, nitro, —(=W)$R^{10}$, —C(=NO$R^{10}$)$R^{10}$, —C(=NN$R^{10}_2$)$R^{10}$, —C(=W)O$R^{10}$, —C(=W)N$R^{10}_2$, —OC(=W)$R^{10}$, —OC(=W)O$R^{10}$, —N$R^{10}$C(=W)$R^{10}$, —N[C(=W)$R^{10}$]$_2$, —N$R^{10}$C(=W)O$R^{10}$, —O$R^{10}$, —N$R^{10}_2$, —S$R^{10}$, —SiR$^{10}_3$, —P$R^{10}_2$, —SO$R^{10}$, —SO$_2$$R^{10}$, —PW$_2$$R^{10}_2$ and —PW$_3$$R^{10}_2$, heterocyclyl,
which is optionally substituted by one or more radicals from the group ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl and ($C_6$–$C_8$)-cycloalkynyl,
where the six abovementioned radicals are optionally substituted by one or more radicals from the group
cyano, nitro, halogen, —C(=W)$R^{10}$, —C(=W)O$R^{10}$, —C(=W)N$R^{10}_2$, —N$R^{10}$C(=W)$R^{10}$, —N[C(=W)$R^{10}$]$_2$, —OC(=W)$R^{10}$, —OC(=W)O$R^{10}$, —O$R^{10}$, —N$R^{10}_2$, —S$R^{10}$, —SO$R^{10}$ and —SO$_2$$R^{10}$);
halogen, cyano, nitro, —C(=W)$R^{10}$, —C(=W)O$R^{10}$, —C(=W)N$R^{10}_2$, —OC(=W)$R^{10}$, —O$R^{10}$, —N$R^{10}_2$, —S$R^{10}$, —SO$R^{10}$ and —SO$_2$$R^{10}$; —O$R^{10}$, —N$R^{10}_2$, —S$R^{10}$, —SO$R^{10}$, —SO$_2$$R^{10}$, —C(=W)$R^{10}$, —C(=NO$R^{10}$)$R^{10}$, —C(=NN$R^{10}_2$)$R^{10}$, —C(=W)O$R^{10}$, —C(=W)N$R^{10}_2$, —OC(=W)$R^{10}$, —OC(=W)O$R^{10}$, —N$R^{10}$C(=W)$R^{10}$, —N[C(=W)$R^{10}$]$_2$, —N$R^{10}$C(=W) O$R^{10}$, —C(=W)N$R^{10}$—N$R^{10}_2$, —C(=W)N$R^{10}$—N$R^{10}$[C (=W)$R^{10}$], —N$R^{10}$—C(=W)N$R^{10}_2$, —N$R^{10}$—N$R^{10}$C (=W)$R^{10}$, —N$R^{10}$—NC(=W)$R^{10}_2$, —N(C=W)$R^{10}$— N$R^{10}_2$, —N$R^{10}$—N$R^{10}$[(C=W)$R^{10}$], —N$R^{10}$—N$R^{10}$ [(C=W)W$R^{10}$], —N$R^{10}$—N$R^{10}$[(C=W)N$R^{10}_2$], —N$R^{10}$ (C=N$R^{10}$)$R^{10}$, —N$R^{10}$(C=N$R^{10}$)N$R^{10}_2$, —O—N$R^{10}_2$, —O—N$R^{10}$(C=W)$R^{10}$, —SO$_2$N$R^{10}_2$, —N$R^{10}$SO$_2$$R^{10}$, —SO$_2$O$R^{10}$, —OSO$_2$$R^{10}$, —SC(=W)$R^{10}$, —SC(=W) O$R^{10}$, —SC(=W)$R^{10}$, —P$R^{10}_2$, —PW$_2$$R^{10}_2$, —PW$_3$$R^{10}_2$, SiR$^{10}_3$ or halogen;
$R^2$ and $R^3$ independently of one another have the definitions given in $R^1$;
$R^2$ and $R^3$ together form a 5- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals $R^1$; $R^4$ and $R^6$ independently of one another have the definitions given in $R^1$;
$R^4$ and $R^6$ together form a 4- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals $R^1$;
$R^5$ and $R^7$ independently of one another are hydrogen, ($C_1$–$C_{20}$)-alkyl, ($C_2$–$C_{20}$)-alkenyl, ($C_2$–$C_{20}$)-alkynyl, ($C_3$–$C_8$)-cycloalkyl, ($C_4$–$C_8$)-cycloalkenyl, ($C_6$–$C_8$)-cycloalkynyl,
where the six last-mentioned radicals are optionally substituted by one or more radicals from the group halogen, cyano, nitro, hydroxyl, —C(=W)R$^{10}$, —C(=NOR$^{10}$)R$^{10}$, —C(=NNR$^{10}{}_2$)R$^{10}$, —C(=W)OR$^{10}$, —C(=W)NR$^{10}{}_2$, —OC(=W)R$^{10}$, —OC(=W)OR$^{10}$, —NR$^{10}$C(=W)R$^{10}$, —N[C(=W)R$^{10}$]$_2$, —NR$^{10}$C(=W)OR$^{10}$, —C(=W)NR$^{10}$—NR$^{10}{}_2$, —(=W)NR$^{10}$—NR$^{10}$[C(=W)R$^{10}$], —NR$^{10}$—C(=W)NR$^{10}{}_2$, —NR$^{10}$—NR$^{10}$C(=W)R$^{10}$, —NR$^{10}$—N[C(=W)R$^{10}$]$_2$, —N[(C=W)R$^{10}$]—NR$^{10}{}_2$, —NR$^{10}$—NR$^{10}$[(C=W)R$^{10}$], —NR$^{10}$—NR$^{10}$[(C=W)WR$^{10}$], —NR$^{10}$—NR$^{10}$[(C=W)NR$^{10}{}_2$], —NR$^{10}$(C=NR$^{10}$)R$^{10}$, —NR$^{10}$(C=NR$^{10}$)NR$^{10}{}_2$, —O—NR$^{10}{}_2$, —O—NR$^{10}$(C=W)R$^{10}$, —OR$^{10}$, —NR$^{10}{}_2$, —SR$^{10}$, —SiR$^{10}{}_3$, —SeR$^{10}$, —PR$^{10}{}_2$, —P(=W)R$^{10}{}_2$, —SOR$^{10}$, —SO$_2$R$^{10}$, —PW$_2$R$^{10}{}_2$, —PW$_3$R$^{10}{}_2$, aryl and heterocyclyl, of which the two mentioned last are optionally substituted by one or more radicals from the group (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl, (C$_6$–C$_8$)-cycloalkynyl, (C$_1$–C$_6$)-haloalkyl, (C$_2$–C$_6$)-haloalkenyl, (C$_2$–C$_6$)-haloalkynyl, halogen, —OR$^{10}$, —NR$^{10}{}_2$, —SR$^{10}$, —SiR$^{10}{}_3$, —C(=W)R$^{10}$, —C(=W)OR$^{10}$, —C(=W)NR$^{10}{}_2$, —SOR$^{10}$, —SO$_2$R$^{10}$, nitro, cyano and hydroxyl, aryl, which is optionally substituted by one or more radicals from the group (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl and (C$_6$–C$_8$)-cycloalkynyl, where these six abovementioned radicals are optionally substituted by one or more radicals from the group halogen, cyano, nitro, —C(=W)R$^{10}$, —C(=W)OR$^{10}$, —C(=W)NR$^{10}{}_2$, —OR$^{10}$, —NR$^{10}{}_2$, —SR$^{10}$, —SOR$^{10}$ and —SO$_2$R$^{10}$;

halogen, cyano, nitro, —C(=W)R$^{10}$, —C(=NOR$^{10}$)R$^{10}$, —C(=NNR$^{10}{}_2$)R$^{10}$, —C(=W)OR$^{10}$, —C(=W)NR$^{10}{}_2$, —OC(=W)R$^{10}$, —OC(=W)OR$^{10}$, —NR$^{10}$C(=W)R$^{10}$, —N[C(=W)R$^{10}$]$_2$, —NR$^{10}$C(=W)OR$_{10}$, —OR$^{10}$, —NR$^{10}{}_2$, —SR$^{10}$, —SiR$^{10}{}_3$, —PR$^{10}{}_2$, —SOR$^{10}$, —SO$_2$R$^{10}$, —PW$_2$R$^{10}{}_2$ and —PW$_3$R$^{10}{}_2$; pyridyl, which is optionally substituted by one or more radicals from the group (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl and (C$_6$–C$_8$)-cycloalkynyl, where the six abovementioned radicals are optionally substituted by one or more radicals from the group cyano, nitro, halogen, —C(=W)R$^{10}$, —C(=W)OR$^{10}$, —C(=W)NR$^{10}{}_2$, —OR$^{10}$, —NR$^{10}{}_2$, —SR$^{10}$, —SOR$^{10}$ and —SO$_2$R$^{10}$, halogen, cyano, nitro, —C(=W)R$^{10}$, —C(=W)OR$^{10}$, —C(=W)NR$^{10}{}_2$, —OC(=W)R$^{10}$, —OR$^{10}$, —NR$^{10}{}_2$, —SR$^{10}$, —SOR$^{10}$ and —S$^{10}{}_2$R$^{10}$;

—C(=W)R$^{10}$, —C(=NOR$^{10}$)R$^{10}$, —C(=NNR$^{10}{}_2$)R$^{10}$, —C(=W)OR$^{10}$, —C(=W)NR$^{10}{}_2$ or halogen;

R$^4$ and R$^5$ together form a 4- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals R$^1$; R$^4$ and R$^5$ together form one of the groups =O, =S or =N—R$^9$; R$^6$ and R$^7$ together form a 5- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals R$^1$;

R$^6$ and R$^7$ together form one of the groups =O, =S or =N—R$^9$;

R$^8$ is hydrogen, (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl, (C$_3$–C$_8$)-cycloalkyl-(C$_1$–C$_4$)-alkyl, (C$_4$–C$_8$)-cycloalkenyl-(C$_1$–C$_4$)-alkyl, (C$_3$–C$_8$)-cycloalkyl-(C$_2$–C$_4$)-alkenyl, (C$_4$–C$_6$)-cycloalkenyl-(C$_1$–C$_4$)-alkenyl, (C$_1$–C$_6$)-alkyl-(C$_3$–C$_8$)-cycloalkyl, (C$_2$–C$_6$)-alkenyl-(C$_3$–C$_8$)-cycloalkyl, (C$_2$–C$_6$)-alkynyl-(C$_3$–C$_8$)-cycloalkyl, (C$_1$–C$_6$)-alkyl-C$_4$–C$_8$)-cycloalkenyl, (C$_2$–C$_6$)-alkenyl-C$_4$–C$_8$)-cycloalkenyl, where the fourteen last-mentioned radicals are optionally substituted by one or more radicals from the group halogen, cyano, nitro, hydroxyl, thio, amino, formyl, (C$_1$–C$_6$)-alkoxy, (C$_2$–C$_6$)-alkenyloxy, (C$_2$–C$_6$)-alkynyloxy, (C$_1$–C$_6$)-haloalkyloxy, (C$_2$–C$_6$)-haloalkenyloxy, (C$_2$–C$_6$)-haloalkynyloxy, (C$_3$–C$_8$)-cycloalkoxy, (C$_4$–C$_8$)-cycloalkenyloxy, (C$_3$–C$_8$)-halocycloalkoxy, (C$_4$–C$_8$)-halocycloalkenyloxy, (C$_3$–C$_8$)-cycloalkyl-(C$_1$–C$_4$)-alkoxy, (C$_4$–C$_8$)-cycloalkenyl-(C$_1$–C$_4$)-alkoxy, (C$_3$–C$_8$)-cycloalkyl-(C$_2$–C$_4$)-alkenyloxy, (C$_4$–C$_8$)-cycloalkenyl-(C$_1$–C$_4$)-alkenyloxy, (C$_1$–C$_6$)-alkyl-(C$_3$–C$_8$)-cycloalkoxy, (C$_2$–C$_6$)-alkenyl-(C$_3$–C$_8$)-cycloalkoxy, (C$_2$–C$_6$)-alkynyl-(C$_3$–C$_8$)-cycloalkoxy, (C$_1$–C$_6$)-alkyl-(C$_4$–C$_8$)-cycloalkenyloxy, (C$_2$–C$_6$)-alkenyl-(C$_4$–C$_8$)-cycloalkenyloxy, (C$_1$–C$_6$)-alkoxy-(C$_1$–C$_6$)-alkoxy, (C$_1$–C$_4$)-alkoxy-(C$_2$–C$_6$)-alkenyloxy, carbamoyl, (C$_1$–C$_6$)-mono- or dialkylcarbamoyl, (C$_1$–C$_6$)-mono- or dihaloalkylcarbamoyl, (C$_3$–C$_8$)-mono- or dicycloalkylcarbamoyl, (C$_1$–C$_6$)-alkoxycarbonyl, (C$_3$–C$_8$)-cycloalkoxycarbonyl, (C$_1$–C$_6$)-alkanoyloxy, (C$_3$–C$_8$)-cycloalkanoyloxy, (C$_1$–C$_6$)-haloalkoxycarbonyl, (C$_1$–C$_6$)-haloalkanoyloxy, (C$_1$–C$_6$)-alkaneamido, (C$_1$–C$_6$)-haloalkaneamido, (C$_2$–C$_6$)-alkeneamido, (C$_3$–C$_8$)-cycloalkaneamido, (C$_3$–C$_8$)-cycloalkyl-(C$_1$–C$_4$)-alkaneamido, (C$_1$–C$_6$)-alkylthio, (C$_2$–C$_6$)-alkenylthio, (C$_2$–C$_6$)-alkynylthio, (C$_1$–C$_6$)-haloalkylthio, (C$_2$–C$_6$)-haloalkenylthio, (C$_2$–C$_6$)-haloalkynylthio, (C$_3$–C$_8$)-cycloalkylthio, (C$_4$–C$_8$)-cycloalkenylthio, (C$_3$–C$_8$)-halocycloalkylthio, (C$_4$–C$_8$)-halocycloalkenylthio, (C$_3$–C$_8$)-cycloalkyl-(C$_1$–C$_4$)-alkylthio, (C$_4$–C$_8$)-cycloalkenyl-(C$_1$–C$_4$)-alkylthio, (C$_3$–C$_8$)-cycloalkyl-(C$_2$–C$_4$)-alkenylthio, (C$_4$–C$_8$)-cycloalkenyl-(C$_1$–C$_4$)-alkenylthio, (C$_1$–C$_6$)-alkyl-(C$_3$–C$_8$)-cycloalkylthio, (C$_2$–C$_6$)-alkenyl-(C$_3$–C$_8$)-cycloalkylthio, (C$_2$–C$_6$)-alkynyl-(C$_3$–C$_8$)-cycloalkylthio, (C$_1$–C$_6$)-alkyl-(C$_4$–C$_8$)-cycloalkenylthio, (C$_2$–C$_6$)-alkenyl-(C$_4$–C$_8$)-cycloalkenylthio, (C$_1$–C$_6$)-alkylsulfinyl, (C$_2$–C$_6$)-alkenylsulfinyl, (C$_2$–C$_6$)-alkynylsulfinyl, (C$_1$–C$_6$)-haloalkylsulfinyl, (C$_2$–C$_6$)-haloalkenylsulfinyl, (C$_2$–C$_6$)-haloalkyny, sulfnyl, (C$_3$–C$_8$)-cycloalkylsulinyl, (C$_4$–C$_8$)-cycloalkenylsulfinyl, (C$_3$–C$_8$)-halocycloalksulfinyl, (C$_4$–C$_8$)-halocycloalkenylsulfinyl, (C$_3$–C$_8$)-cycloalkyl-(C$_1$–C$_4$)-alkylsulfinyl, (C$_4$–C$_8$)-cycloalkenyl-(C$_1$–C$_4$)-alkylsulfinyl, (C$_3$–C$_8$)-cycloalkyl-(C$_2$–C$_4$)-alkenylsulfinyl, (C$_4$–C$_8$)-cycloalkenyl-(C$_1$–C$_4$)-alkenylsulfinyl, (C$_1$–C$_6$)-alkyl-(C$_3$–C$_8$)- cycoalkylsulfinyl, (C$_2$–C$_6$)- alkenyl-(C$_3$–C$_8$)-cycloalkylsulfinyl, (C$_2$–C$_6$)-alkynyl-(C$_3$–C$_8$)-cycloalkylsulfinyl, (C$_1$–C$_6$)-alkyl-(C$_4$–C$_8$)-cycloalkenylsulfinyl, (C$_2$–C$_6$)-alkenyl-(C$_4$–C$_8$)-cycloalkenylsulfinyl, (C$_1$–C$_6$)-alkylsulfonyl, (C$_2$–C$_6$)-alkenylsulfonyl, (C$_2$–C$_6$)-alkynylsulfonyl, (C$_1$–C$_6$)-haloalkylsulfonyl , (C$_2$–C$_6$)-haloalkenylsulfonyl, (C$_2$–C$_6$)-haloalkynylsulfonyl, (C$_3$–C$_8$)-cycloalkylsulfonyl, (C$_4$–C$_8$)-cycloalkenylsulfonyl, (C$_3$–C$_8$)-halocycloalkylsulfonyl, (C$_4$–C$_8$)-halocycloalkenyisulfonyl, (C$_3$–C$_8$)-cycloalkyl-(C$_1$–C$_4$)-alkylsulfonyl, (C$_4$–C$_8$ )-cycloalkenylony-(C$_1$–C$_4$)-alkylsulfonyl, (C$_3$–C$_8$)-cycloalkyl-(C$_2$–C$_4$)-alkenylsulfonyl, (C$_4$–C$_8$)-cycloalkenyl-(C$_1$–C$_4$)-alkenylsulfonyl, (C$_1$–C$_6$)-alkyl-(C$_3$–C$_8$)-cycloalkylsulfonyl, (C$_2$–C$_6$)-alkenyl-(C$_3$–C$_8$)-cycloalkylsulfonyl, (C$_2$–C$_6$)-alkynyl-(C$_3$–C$_8$)-cycloalkylsulfonyl, (C$_1$–C$_6$)-alkyl-(C$_4$–C$_8$)- cycloalkenylsulfonyl, ($C_2$–$C_6$)-alkenyl-($C_4$–$C_8$)-cycloalkenylsulfonyl, ($C_1$–$C_6$)-alkylamino, ($C_2$–$C_6$)-alkenylamino, ($C_2$–$C_6$)-alkynylamino, ($C_1$–$C_6$)-haloalkylamino, ($C_2$–$C_6$)-haloalkenylamino, ($C_2$–$C_6$)-haloalkynylamino, ($C_3$–$C_8$)-cycloalkylamino, ($C_4$–$C_8$)-cycloalkenylamino, ($C_3$–$C_8$)-halocycloalkamino, ($C_4$–$C_8$)-halocycloalkenylamino, ($C_3$–$C_8$)-cycloalkyl-($C_1$–$C_4$)-alkylamino, ($C_4$–$C_8$)-cycloalkenyl-($C_1$–$C_4$)-alkylamino, ($C_3$–$C_8$)-cycloalkyl-($C_2$–$C_4$)-alkenylamino, ($C_4$–$C_8$)-cycloalkenyl-($C_1$–$C_4$)-alkenylamino, ($C_1$–$C_6$)-alkyl-($C_3$–$C_8$)-cycloalkylamino, ($C_2$–$C_6$)-alkenyl-($C_3$–$C_8$)-cycloalkylamino, ($C_2$–$C_6$)-alkynyl-($C_3$–$C_8$)-cycloalkylamino, ($C_1$–$C_6$)-alkyl-($C_4$–$C_8$)-cycloalkenylamino, ($C_2$–$C_6$)-alkenyl-($C_4$–$C_8$)-cycloalkenylamino, ($C_1$–$C_6$)-trialkylsilyl, aryl, aryloxy, arylthio, arylamino, arylcarbamoyl, aroyl, aroyloxy, aryloxycarbonyl, aryl-($C_1$–$C_4$)-alkoxy, aryl-($C_2$–$C_4$)-alkenyloxy, aryl-($C_1$–$C_4$)-alkylthio, aryl-($C_2$–$C_4$)-alkenylthio, aryl-($C_1$–$C_4$)-alkylamino, aryl-($C_2$–$C_4$)-alkenylamino, aryl-($C_1$–$C_6$)-dialkylsilyl, diaryl-($C_1$–$C_6$)-alkylsilyl, triarylsilyl and 5- or 6-membered heterocyclyl, of which the nineteen last-mentioned radicals are optionally substituted in their cyclic moiety by one or more substituents from the group halogen, cyano, nitro, amino, hydroxyl, thio, ($C_1$–$C_4$)-alkyl, ($C_1$–$C_4$)-haloalkyl, ($C_1$–$C_4$)-alkoxy, ($C_1$–$C_4$)-haloalkoxy, ($C_1$–$C_4$)-alkylthio, ($C_1$–$C_4$)-haloalkylthio, ($C_1$–$C_4$)-alkylamino, ($C_1$–$C_4$)-haloalkylamino, formyl and ($C_1$–$C_4$)-alkanoyl; aryl, which is optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, carbamoyl, ($C_1$–$C_6$)-mono- or dialkylcarbamoyl, ($C_1$–$C_6$)-alkoxycarbonyl, ($C_1$–$C_6$)-alkanoyloxy, ($C_1$–$C_6$)-mono- or dihaloalkylcarbamoyl, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_1$–$C_6$)-alkylthio, ($C_2$–$C_6$)-alkenylthio, ($C_2$–$C_6$)-alkynylthio, ($C_1$–$C_6$)-haloalkylthio, ($C_2$–$C_6$)-haloalkenylthio, ($C_2$–$C_6$)-haloalkynylthio, ($C_3$–$C_8$)-cycloalkylthio, ($C_4$–$C_8$)-cycloalkenylthio, ($C_3$–$C_8$)-halocycloalkthio, ($C_4$–$C_8$)-halocycloalkenylthio, ($C_1$–$C_6$)-alkylsulfinyl, ($C_2$–$C_6$)-alkenylsulfinyl, ($C_2$–$C_6$)-alkynylsulfinyl, ($C_2$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_1$–$C_6$)-alkylsulfonyl, ($C_2$–$C_6$)-alkenylsulfonyl, ($C_2$–$C_6$)-alkynylsulfonyl, ($C_1$–$C_6$)-haloalkylsulfonyl, ($C_2$–$C_6$)-haloalkenylsulfonyl, ($C_2$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalksulfonyl, ($C_4$–$C_8$)-halocycloalkenylsulfonyl, ($C_2$–$C_6$)-alkylamino, ($C_2$–$C_6$)-alkenylamino, ($C_2$–$C_6$)-alkynylamino, ($C_1$–$C_6$)-haloalkylamino, ($C_2$–$C_6$)-haloalkenylamino, ($C_2$–$C_6$)-haloalkynylamino, ($C_3$–$C_8$)-cycloalkylamino, ($C_4$–$C_8$)-cycloalkenylamino, ($C_3$–$C_8$)-halocycloalkamino and ($C_4$–$C_8$)-halocycloalkenylamino, —C(=W)$R^{11}$, $OR^{11}$ or $NR^{11}_2$;

$R^9$ is ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_3$–$C_8$)-cycloalkyl-($C_1$–$C_4$)-alkyl, ($C_4$–$C_8$)-cycloalkenyl-($C_1$–$C_4$)-alkyl, ($C_3$–$C_8$)-cycloalkyl-($C_2$–$C_4$)-alkenyl, ($C_4$–$C_8$)-cycloalkenyl-($C_1$–$C_4$)-alkenyl, where the nine last-mentioned radicals are optionally substituted by one or more radicals from the group halogen, cyano, ($C_1$–$C_6$)-alkoxy, ($C_2$–$C_6$)-alkenyloxy, ($C_2$–$C_6$) alkynyloxy and ($C_1$–$C_6$)-haloalkyloxy;

$R^{10}$ is hydrogen, ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_3$–$C_8$)-cycloalkyl-($C_1$–$C_4$)-alkyl, ($C_4$–$C_8$)-cycloalkenyl-($C_1$–$C_4$)-alkyl, ($C_3$–$C_8$)-cycloalkyl-($C_2$–$C_4$)-alkenyl, ($C_4$–$C_8$)-cycloalkenyl-($C_1$–$C_4$)-alkenyl, ($C_1$–$C_6$)-alkyl-($C_3$–$C_8$)-cycloalkyl, ($C_2$–$C_6$)-alkenyl-($C_3$–$C_8$)-cycloalkyl, ($C_2$–$C_6$)-alkynyl-($C_3$–$C_8$)-cycloalkyl, ($C_1$–$C_6$)-alkyl-($C_4$–$C_8$)-cycloalkenyl, ($C_2$–$C_6$)-alkenyl-($C_4$–$C_8$)-cycloalkenyl, where the fourteen last-mentioned radicals are optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, ($C_3$–$C_8$)-cycloalkyl-($C_1$–$C_4$)-alkoxy, ($C_4$–$C_8$)-cycloalkenyl-($C_1$–$C_4$)-alkoxy, ($C_3$–$C_8$)-cycloalkyl-($C_2$–$C_4$)-alkenyloxy, ($C_4$–$C_8$)-cycloalkenyl-($C_1$–$C_4$)-alkenyloxy, ($C_1$–$C_6$)-alkyl-($C_3$–$C_8$)-cycloalkoxy, ($C_2$–$C_6$)-alkenyl-($C_3$–$C_8$)-cycloalkoxy, ($C_2$–$C_6$)-alkynyl-($C_3$–$C_8$)-cycloalkoxy, ($C_1$–$C_6$)-alkyl-($C_4$–$C_8$)-cycloalkenyloxy, ($C_2$–$C_6$)-alkenyl-($C_4$–$C_8$)-cycloalkenyloxy, ($C_1$–$C_4$)-alkoxy-($C_1$–$C_6$)-alkoxy, ($C_1$–$C_4$)-alkoxy-($C_2$–$C_6$)-alkenyloxy, carbamoyl, ($C_1$–$C_6$)-mono- or dialkylcarbamoyl, ($C_1$–$C_6$)-mono- or dihaloalkylcarbamoyl, ($C_3$–$C_8$)-mono- or dicycloalkylcarbamoyl, ($C_1$–$C_6$)-alkoxycarbonyl, ($C_3$–$C_8$)-cycloalkoxycarbonyl, ($C_1$–$C_6$)-alkanoyloxy, ($C_3$–$C_8$)-cycloalkanoyloxy, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_3$–$C_8$)-cycloalkaneamido, ($C_3$–$C_8$)-cycloalkyl-($C_1$–$C_4$)-alkaneamido, ($C_1$–$C_6$)-alkylthio, ($C_2$–$C_6$)-alkenylthio, ($C_2$–$C_6$)-alkynylthio, ($C_1$–$C_6$)-haloalkylthio, ($C_2$–$C_6$)-haloalkenylthio, ($C_2$–$C_6$)-haloalkynylthio, ($C_3$–$C_8$)-cycloalkylthio, ($C_4$–$C_8$)-cycloalkenylthio, ($C_3$–$C_8$)-halocycloalkthio, ($C_4$–$C_8$)-halocycloalkenylthio, ($C_3$–$C_8$)-cycloalkyl-($C_1$–$C_4$)-alkylthio, ($C_4$–$C_8$)-cycloalkenyl-($C_1$–$C_4$)-alkylthio, ($C_3$–$C_8$)-cycloalkyl-($C_2$–$C_4$)-alkenylthio, ($C_4$–$C_8$)-cycloalkenyl-($C_1$–$C_4$)-alkenylthio, ($C_1$–$C_6$)-alkyl-($C_3$–$C_8$)-cycloalkylthio, ($C_2$–$C_6$)-alkenyl-($C_3$–$C_8$)-cycloalkylthio, ($C_2$–$C_6$)-alkynyl-($C_3$–$C_8$)-cycloalkylthio, ($C_1$–$C_6$)-alkyl-($C_4$–$C_8$)-cycloalkenylthio, ($C_2$–$C_6$)-alkenyl-($C_4$–$C_8$)-cycloalkenylthio, ($C_1$–$C_6$)-alkylsulfinyl, ($C_2$–$C_6$)-alkenylsulfinyl, ($C_2$–$C_6$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_3$–$C_8$)-cycloalkyl-($C_1$–$C_4$)-alkylsulfinyl, ($C_4$–$C_8$)-cycloalkenyl-($C_1$–$C_4$)-alkylsulfinyl, ($C_3$–$C_8$)-cycoalkyl-($C_2$–$C_4$)-alkenylsulfinyl, ($C_4$–$C_8$)-cycloalkenyl-($C_1$–$C_4$)-alkenylsulfinyl, ($C_1$–$C_6$)-alkyl-($C_3$–$C_8$)-cycloalkylsulfinyl, ($C_2$–$C_6$)-alkenyl-($C_3$–$C_8$)-cycloalkylsulfinyl, ($C_2$–$C_6$)-alkynyl-($C_3$–$C_8$)-cycloalkylsulfinyl, ($C_1$–$C_6$)-alkyl-($C_4$–$C_8$)-cycloalkenylsulfinyl, ($C_2$–$C_6$)-alkenyl-($C_4$–$C_8$)-cycloalkenylsulfinyl, ($C_1$–$C_6$)-alkylsulfonyl, ($C_2$–$C_6$)-alkenylsulfonyl, ($C_2$–$C_6$)-alkynylsulfonyl, ($C_1$–$C_6$)-haloalkylsulfonyl, ($C_2$–$C_6$)-haloalkenylsulfonyl, ($C_2$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalksulfonyl, ($C_4$–$C_8$)-halocycloalkenylsulfonyl, ($C_3$–$C_8$)-cycloalkyl-($C_1$–$C_4$)-alkylsulfonyl, ($C_4$–$C_8$)-cycloalkenyl-($C_1$–$C_4$)-alkylsulfonyl, ($C_3$–$C_8$)- ycloalkyl-($C_2$–$C_4$)-alkenylsulfonyl, ($C_4$–$C_8$)-cycloalkenyl-($C_1$–$C_4$)-alkenyl sulfonyl, ($C_1$–$C_8$)-alkyl-($C_3$–$C_8$)-cycloalkylsulfonyl, ($C_2$–$C_6$)-alkenyl-($C_3$–$C_8$)-cycloalkylsulfonyl, ($C_2$–$C_6$)-alkynyl-($C_3$–$C_8$)-cycloalkylsulfonyl, ($C_1$–$C_6$)-alkyl-($C_4$–$C_8$)-cycloalkenylsulfonyl, ($C_2$–$C_6$)-alkenyl-($C_4$–$C_8$)-cycloalkenylsulfonyl, ($C_1$–$C_6$)-alkylamino, ($C_2$–$C_6$)-alkenylamino, ($C_2$–$C_6$)-alkyenyl amino, ($C_1$–$C_6$)-haloalkylamino, ($C_2$–$C_6$)-haloalkenylamino, ($C_2$–$C_6$)-haloalkynylamino, ($C_3$–$C_8$)-cycloalkylamino, ($C_4$–$C_8$)-cycloalkenylamino, ($C_3$–$C_8$)-halocycloalkamino, ($C_4$–$C_8$)-halocycloalkenylamino, ($C_3$–$C_8$)-cycloalkyl-($C_1$–$C_4$)-alkylamino, ($C_4$–$C_8$)-cycloalkenyl-($C_1$–$C_4$)-alkylamino, ($C_3$–$C_8$)-cycloalkyl-($C_2$–$C_4$)-alkenylamino, ($C_4$–$C_8$)-cycloalkenyl-($C_1$–$C_4$)-alkenylamino, ($C_1$–$C_6$)-alkyl-($C_3$–$C_8$)-cycloalkylamino, ($C_2$–$C_6$)-alkenyl-($C_3$–$C_8$)-cycloalkylamino, ($C_2$–$C_6$)-alkynyl-($C_3$–$C_8$)-cycloalkylamino, ($C_1$–$C_6$)-alkyl-($C_4$–$C_8$)-cycloalkenylamino, ($C_2$–$C_6$)-alkenyl-($C_4$–$C_8$)-cycloalkenylamino, ($C_1$–$C_6$)-trialkylsilyl, aryl, aryloxy, arylthio, arylamino, aryl-$C_1$–$C_4$)-alkoxy, aryl-($C_2$–$C_4$)-alkenyloxy, aryl-($C_1$–$C_4$)-alkylthio, aryl-($C_2$–$C_4$)-alkenylthio, aryl-($C_1$–$C_4$)-alkylamino, aryl-($C_2$–$C_4$)-alkenylamino, aryl-($C_1$–$C_6$)-dialkylsilyl, diaryl-($C_1$–$C_6$)-alkylsilyl, triarylsilyl and 5- or 6-membered heterocyclyl, where the cyclic moiety of the fourteen last-mentioned radicals is optionally substituted by one or more radicals from the group halogen, cyano, nitro, amino, hydroxyl, thio, ($C_1$–$C_4$)-alkyl, ($C_1$–$C_4$)-haloalkyl, ($C_3$–$C_8$)-cycloalkyl, ($C_1$–$C_4$)-alkoxy, ($C_1$–$C_4$)-haloalkoxy, ($C_1$–$C_4$)-alkylthio, ($C_1$–$C_4$)-haloalkylthio, ($C_1$–$C_4$)-alkylamino, ($C_1$–$C_4$)-haloalkylamino, formyl and ($C_1$–$C_4$)-alkanoyl;

aryl, 5- or 6-membered heteroaromatic, where the two last-mentioned radicals are optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, carbamoyl, ($C_1$–$C_6$)-mono- or dialkylcarbamoyl, ($C_1$–$C_6$)-alkoxycarbonyl, ($C_1$–$C_6$)-alkanoyloxy, ($C_1$–$C_6$)-mono- or dihaloalkylcarbamoyl, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_1$–$C_6$)-alkylthio, ($C_2$–$C_6$)-alkenylthio, ($C_2$–$C_6$)-alkynylthio, ($C_1$–$C_6$)-haloalkylthio, ($C_2$–$C_6$)-haloalkenylthio, ($C_2$–$C_6$)-haloalkynylthio, ($C_3$–$C_8$)-cycloalkylthio, ($C_4$–$C_8$)-cycloalkenylthio, ($C_3$–$C_8$)-halocycloalkthio, ($C_4$–$C_8$)-halocycloalkenylthio, ($C_1$–$C_6$)-alkylsulfinyl, ($C_2$–$C_6$)-alkenylsulfinyl, ($C_2$–$C_6$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_1$–$C_6$)-alkylsulfonyl, ($C_2$–$C_6$)-alkenylsulfonyl, ($C_2$–$C_6$)-alkynylsulfonyl, ($C_1$–$C_6$)-haloalkylsulfonyl, ($C_2$–$C_6$)-haloalkenylsulfonyl, ($C_2$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalksulfonyl, ($C_4$–$C_8$)-halocycloalkenylsulfonyl, ($C_1$–$C_6$)-alkylamino, ($C_2$–$C_6$)-alkenylamino, ($C_2$–$C_6$)-alkynylamino, ($C_1$–$C_6$)-haloalkylamino, ($C_2$–$C_6$)-haloalkenylamino, ($C_2$–$C_6$)-haloalkynylamino, ($C_3$–$C_8$)-cycloalkylamino, ($C_4$–$C_8$)cycloalkenylamino, ($C_3$–$C_8$)-halocycloalkylamino and ($C_4$–$C_8$)-halocycloalkenylamino;

$R^{11}$ is ($C_1$–$C_{10}$)-alkyl, haloalkyl, aryl, which is optionally substituted by one or more radicals from the group halogen, cyano, nitro, ($C_1$–$C_4$)-alkoxy, ($C_1$–$C_4$)-alkyl, amino, ($C_1$–$C_4$)-monoalkylamino and ($C_1$–$C_4$)-dialkylamino; $NR^{10}{}_2$, $OR^{10}$ or $SR^{10}$.

The term "halogen" includes fluorine, chlorine, bromine and iodine.

The term "($C_1$–$C_4$)-alkyl" is to be understood as a straight-chain or branched hydrocarbon radical having 1, 2, 3 or 4 carbon atoms, such as, for example, the methyl, ethyl, propyl, isopropyl, 1-butyl, 2-butyl, 2-methylpropyl or tert-butyl radical. Correspondingly, alkyl radicals having a greater range of carbon atoms are to be understood as straight-chain or branched saturated hydrocarbon radicals which contain a number of carbon atoms which corresponds to the range stated. Thus, the term "($C_1$–$C_6$)-alkyl" includes the abovementioned alkyl radicals, and, for example, the pentyl, 2-methylbutyl, 1,1-dimethylpropyl, hexyl radical. The term "($C_1$–$C_{10}$)-alkyl" is to be understood as the abovementioned alkyl radicals, and, for example, the nonyl, 1-decyl or 2-decyl radical and the term "($C_1$–$C_{20}$)-alkyl" is to be understood as the abovementioned alkyl radicals, and, for example, the undecyl, dodecyl, pentadecyl or eicosyl radical.

"($C_1$–$C_4$)-Haloalkyl" is to be understood as an alkyl group mentioned under the term "($C_1$–$C_4$)-alkyl" in which one or more hydrogen atoms are replaced by the same number of identical or different halogen atoms, preferably by fluorine or chlorine, such as the trifluoromethyl, the 1-fluoroethyl, the 2,2,2-trifluoroethyl, the chloromethyl, fluoromethyl, the difluoromethyl and the 1,1,2,2-tetrafluoroethyl group.

"($C_1$–$C_4$)-Alkoxy" is to be understood as an alkoxy group whose hydrocarbon radical has the meaning given under the term "($C_1$–$C_4$)-alkyl". Alkoxy groups embracing a greater range of carbon atoms are to be understood correspondingly.

The terms "alkenyl" and "alkynyl" having a prefix stating the range of carbon atoms denote a straight-chain or branched hydrocarbon radical having a number of carbon atoms corresponding to the range stated which comprises at least one multiple bond which may be in any position of the unsaturated radical in question. "($C_2$–$C_4$)-Alkenyl" is thus, for example, the vinyl, allyl, 2-methyl-2-propene or 2-butenyl group; "($C_2$–$C_6$)-alkenyl" denotes the abovementioned radicals and, for example, the pentenyl, 2-methylpentenyl or the hexenyl group. The term "($C_2$–$C_{20}$)-alkenyl" is to be understood as the abovementioned radicals and, for example, the 2-decenyl or the 2-eicosenyl group. "($C_2$–$C_4$)-Alkynyl" is, for example, the ethynyl, propargyl, 2-methyl-2-propyne or 2-butynyl group. "($C_2$–$C_6$)-Alkynyl" is to be understood as the abovementioned radicals and, for example, the 2-pentynyl- or the 2-hexynyl group and "($C_2$–$C_{20}$)-alkynyl" is to be understood as the abovementioned radicals and, for example, the 2-octynyl or the 2-decynyl group.

"($C_3$–$C_8$)-cycloalkyl" denotes monocyclic alkyl radicals, such as the cyclopropyl, cyclobutyl, cyclopentyl, cyclohexyl, cycloheptyl or cyclooctyl radical and bicyclic alkyl radicals, such as the norbornyl radical.

The term "($C_3$–$C_8$)-cycloalkyl-($C_1$–$C_4$)-alkyl" is to be understood as, for example, the cyclopropylmethyl, cyclopentylmethyl, cyclohexylmethyl, cyclohexylethyl and cyclohexylbutyl radical, and the term "($C_1$–$C_6$)-alkyl-($C_3$–$C_8$)-cycloalkyl is to be understood as, for example, the 1-methylcyclopropyl, 1-methylcyclopentyl, 1-methylcyclohexyl, 3-hexylcyclobutyl and 4-tert-butyl-cyclohexyl radical.

"($C_1$–$C_4$)-Alkoxy-($C_1$–$C_6$)-alkyloxy" is an alkoxy group as defined above which is substituted by a further alkoxy group, such as, for example, 1-ethoxyethoxy.

"($C_3$–$C_8$)-cycloalkoxy" or "($C_3$–$C_8$)-cycloalkylthio" is to be understood as one of the abovementioned ($C_3$–$C_8$)-cycloalkyl radicals which is linked via an oxygen or sulfur atom.

"(C₃–C₈)-cycloalkyl-(C₁–C₆)-alkoxy" is, for example, the cyclopropylmethoxy, cyclobutylmethoxy, cyclopentylmethoxy, cyclohexylmethoxy, cyclohexylethoxy or the cyclohexylbutoxy group;

The term "(C₁–C₄)-alkyl-(C₃–C₈)-cycloalkoxy" is, for example, the methylcyclopropyloxy, methylcyclobutyloxy or the butylcyclohexyloxy group.

"(C₁–C₆)-Alkylthio" is an alkylthio group whose hydrocarbon radical has the meaning given under the term "(C₁–C₆)-alkyl".

Correspondingly, "(C₁–C₆)-alkylsulfinyl" is, for example, the methyl-, ethyl-, propyl-, isopropyl-, butyl-, isobutyl-, sec-butyl- or tert-butylsulfinyl group and "(C₁–C₆)-alkylsulfonyl" is, for example, the methyl-, ethyl-, propyl-, isopropyl-, butyl-, isobutyl-, sec-butyl- or tert-butylsulfonyl group.

"(C₁–C₆)-Alkylamino" is a nitrogen atom which is substituted by one or two identical or different alkyl radicals of the above definition.

The term "(C₁–C₆)-mono- or dialkylcarbamoyl" is a carbamoyl group having one or two hydrocarbon radicals which have the meaning given under the term "(C₁–C₆–alkyl)" and which, in the case of two hydrocarbon radicals, may be identical or different.

Correspondingly, "(C₁–C₆)-dihaloalkylcarbamoyl" is a carbamoyl group which carries two (C₁–C₆)-haloalkyl radicals in accordance with the above definition or one (C₁–C₆)-haloalkyl radical and one (C₁–C₆)-alkyl radical in accordance with the above definition.

"(C₁–C₆)-Alkanoyl" is, for example, the acetyl, propionyl, butyryl or 2-methylbutyryl group.

The term "aryl" is to be understood as an isocyclic aromatic radical preferably having 6 to 14, in particular 6 to 12, carbon atoms, such as, for example, phenyl, naphthyl or biphenylyl, preferably phenyl. "Aroyl" is thus an aryl radical as defined above which is attached via a carbonyl group, such as, for example, the benzoyl group.

The term "heterocyclyl" denotes a cyclic radical which may be fully saturated, partially unsaturated or fully unsaturated and which may be interrupted by at least one or more identical atoms from the group nitrogen, sulfur or oxygen, oxygen atoms, however, not being directly adjacent to one another and at least one carbon atom being present in the ring, such as, for example, a thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine 4H-quinolizine; piperidine, pyrrolidine, oxazoline, tetrahydrofuran, tetrahydropyran, isoxazolidine or thiazolidine radical. The term "heteroaromatic" thus embraces, from among the meanings mentioned above under "heterocyclyl", in each case the fullly unsaturated aromatic heterocyclic compounds.

"Aryl-(C₁–C₄)-alkoxy" is an aryl radical which is attached via a (C₁–C₄)-alkoxy group, for example the benzyloxy, phenylethoxy, phenylbutoxy or naphthylmethoxy radical.

"Arylthio" is an aryl radical attached via a sulfur atom, for example the phenylthio or the 1- or 2-naphthylthio radical. Correspondingly, "aryloxy" is, for example, the phenoxy or 1- or 2-naphthyloxy radical.

"Aryl-(C₁–C₄)-alkylthio" is an aryl radical which is attached via an alkylthio radical, for example the benzylthio, naphthylmethylthio or the phenylethylthio radical.

The term "(C₁–C₆)-trialkylsilyl" denotes a silicon atom which carries three identical or different alkyl radicals in accordance with the above definition. Correspondingly "aryl-(C₁–C₆)-dialkylsilyl" is a silicon atom which carries one aryl radical and two identical or different radicals in accordance with the above defition, "diaryl-(C₁–C₆)-alkylsilyl" is a silicon atom which carries one alkyl radical and two identical or different aryl radicals in accordance with the above definition, and "triarylsilyl" is a silicon atom which carries three identical or different aryl radicals in accordance with the above definition.

In cases where two or more radicals $R^{10}$ are present in a substituent, such as, for example, in $-C(=W)NR^{10}{}_2$, these radicals may be identical or different.

Preference is given to those compounds of the formula I in which

Y is C₁–C₆–alkyl which is mono- or polysubstituted by chlorine and/or fluorine;

m is zero;

Q is a 5-membered heterocyclic group

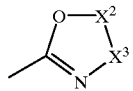

in which a) $X^2=NR^a$ and $X^3=CR^bR^1$ or b) $X^2=CR^aR^2$ and $X^3=CR^bR^3$ or c) $X^2=CR^4R^5$ and $X^3=CR^6R^7$;

$R^a$ and $R^b$ together are a bond;

$R^1$, $R^2$, $R^3$, $R^4$ and $R^6$ are each independently of one another hydrogen, halogen, C₁–C₁₂-alkyl, C₃–C₈–cycloalkyl, C₂–C₈–alkenyl, C₂–C₈–alkynyl, where the four last-mentioned hydrocarbon radicals are optionally mono- or polysubstituted by identical or different radicals from a group A1 consisting of C₁–C₆–alkylcarbonyl, C₁–C₆-alkylaminocarbonyl, C₁–C₆–alkoxy, C₁–C₆–alkylthio, C₁–C₆–alkylamino, C₁–C₆–alkylcarbonylamino, C₁–C₆–alkylsulfonylamino, phenyl, furyl, pyrryl, thienyl, halogen, cyano, phenyloxy, phenylthio and phenylamino, where the eleven first-mentioned radicals of group A1 are each optionally mono- or polysubstituted by identical or different radicals from a group B1 consisting of halogen, cyano, C₁–C₃–alkoxy and phenyl which is optionally mono- or polysubstituted by one or more halogen atoms and where the three last-mentioned radicals of group A1 are each optionally mono- or polysubstituted by identical or different radicals from a group B2 consisting of halogen, cyano, nitro, C₁–C₃–alkyl and C₁–C₃–alkoxy, or are C₁–C₆–alkylcarbonyl, C₁–C₆–alkylaminocarbonyl, C₁–C₆–alkoxycarbonyl, phenyl, pyridyl, furyl, thienyl, pyrryl, where the eight last-mentioned radicals are optionally mono- or polysubstituted by identical or different radicals from group B1, or are $OR^{10}$, $SR^{10}$ or $N(R^{10})_2$;

$R^5$ and $R^7$ are each independently of one another hydrogen, halogen, C₁–C₁₂-alkyl, C₃–C₈–cycloalkyl, C₂–C₈–alkenyl, C₂–C₈–alkynyl, where the four last-mentioned hydrocarbon radicals are optionally mono- or polysubstituted by identical or different radicals from a group A2 consisting of $C_1$–$C_6$-alkylcarbonyl, $C_1$–$C_6$-alkylaminocarbonyl, $C_1$–$C_6$-alkoxy, $C_1$–$C_6$-alkylthio, $C_1$–$C_6$-alkylamino, $C_1$–$C_6$-alkylcarbonylamino, phenyl, furyl, pyrryl, thienyl, halogen, cyano, phenyloxy, phenylthio and phenylamino, where the ten first-mentioned radicals of group A2 are each optionally mono- or polysubstituted by identical or different radicals from the group B1 and the three last-mentioned radicals of group A2 are each optionally mono- or polysubstituted by identical or different radicals from the group B2, or are $C_1$–$C_6$-alkylcarbonyl, $C_1$–$C_6$-alkylaminocarbonyl, $C_1$–$C_6$-alkoxycarbonyl, phenyl, pyridyl, furyl, thienyl, pyrryl, where the eight last-mentioned radicals are optionally mono- or polysubstituted by identical or different radicals from the group B1, or are $OR^{10}$, $SR^{10}$ or $N(R^{10})_2$;

$R^{10}$ is hydrogen, benzyl, $C_1$–$C_6$-alkyl, $C_1$–$C_6$-cycloalkyl, $C_2$–$C_6$-alkenyl, $C_2$–$C_6$-alkynyl, phenyl, $C_1$–$C_6$-alkylcarbonyl or $C_1$–$C_6$-alkylsulfonyl, where the eight last-mentioned radicals are optionally mono- or polysubstituted by identical or different halogen atoms.

Particular preference is given to compounds of the formula I in which

Y is trifluoromethyl;

$R^1$, $R^2$, $R^3$, $R^4$ and $R^6$ are each independently of one another halogen, $C_1$–$C_{12}$-alkyl, $C_2$–$C_{12}$-alkenyl, where the two last-mentioned radicals are optionally mono- or polysubstituted by identical or different radicals from a group A3 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, $C_1$–$C_4$-alkylsulfonylamino, phenyl, furyl, pyrryl, thienyl, fluorine, chlorine, bromine, cyano, phenyloxy, phenylthio and phenylamino, where the eleven first-mentioned radicals of group A3 are each optionally mono- or polysubstituted by identical or different radicals from the group B1 and the three last-mentioned radicals of group A3 are each optionally mono- or polysubstituted by identical or different radicals from the group B2, or are $OR^{10}$, $SR^{10}$ or $N(R^{10})_2$;

$R^5$ and $R^7$ are each independently of one another halogen, $C_1$–$C_{12}$-alkyl, $C_2$–$C_{12}$-alkenyl, where the two last-mentioned radicals are optionally mono- or polysubstituted by identical or different radicals from a group A4 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, phenyl, furyl, pyrryl, thienyl, fluorine, chlorine, bromine, cyano, phenyloxy, phenylthio and phenylamino, where the ten first-mentioned radicals of group A4 are each optionally mono- or polysubstituted by identical or different radicals from the group B1 and the three last-mentioned radicals of group A4 are each optionally mono- or polysubstituted by identical or different radicals from the group B2, or are $OR^{10}$, $SR^{10}$ or $N(R^{10})_2$;

$R^{10}$ is hydrogen, $C_1$–$C_6$-alkyl, $C_2$–$C_6$-alkenyl, $C_2$–$C_6$-alkynyl, phenyl, $C_1$–$C_4$-alkylcarbonyl or $C_1$–$C_4$-alkylsulfonyl, where the six last-mentioned radicals are optionally mono- or polysubstituted by identical or different halogen atoms.

Very particular preference is given to compounds of the formula I in which $R^1$, $R^2$, $R^3$, $R^4$ and $R^6$ are each independently of one another $C_1$–$C_{10}$-alkyl, $C_2$–$C_{10}$-alkenyl, where the two last-mentioned radicals are optionally mono- or polysubstituted by identical or different radicals from a group A5 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, $C_1$–$C_4$-alkylsulfonylamino, phenyl, fluorine, chlorine, bromine, cyano, phenyloxy, phenylthio and phenylamino, where the eight first-mentioned radicals of group A5 are each optionally mono- or polysubstituted by identical or different radicals from the group B1 and the three last-mentioned radicals of group A5 are each optionally mono- or polysubstituted by identical or different radicals from the group B2;

$R^5$ and $R^7$ are each independently of one another $C_1$–$C_{10}$-alkyl, $C_2$–$C_{10}$-alkenyl, where the two last-mentioned radicals are optionally mono- or polysubstituted by identical or different radicals from a group A6 consisting of $C_1$–$C_4$-alkylcarbonyl, $C_1$–$C_4$-alkylaminocarbonyl, $C_1$–$C_4$-alkoxy, $C_1$–$C_4$-alkylthio, $C_1$–$C_4$-alkylamino, $C_1$–$C_4$-alkylcarbonylamino, phenyl, fluorine, chlorine, bromine, cyano, phenyloxy, phenylthio and phenylamino, where the seven first-mentioned radicals of group A6 are each optionally mono- or polysubstituted by identical or different radicals from the group B1 and the three last-mentioned radicals of group A6 are each optionally mono- or polysubstituted by identical or different radicals from the group B2.

Depending on the nature of the substituents defined above, the compounds of the formula (I) have acidic or basic properties and can form salts. If the compounds of the formula (I) carry, for example, groups such as hydroxyl, carboxyl and other groups inducing acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, further ammonia, primary, secondary and tertiary amines having ($C_1$–$C_4$)-alkyl radicals and also mono-, di- and trialkanolamines of ($C_1$–$C_4$)-alkanols. If the compounds of the formula (I) carry, for example, groups such as amino, alkylamino and other groups inducing basic properties, these compounds can be reacted with acids to give salts. Suitable acids are, for example, mineral acids, such as hydrochloric acid, sulfuric acid and phosphoric acid, organic acids, such as acetic acid, oxalic acid and acidic salts, such as $NaHSO_4$ and $KHSO_4$. The salts which can be obtained in this manner likewise have insecticidal, acaricidal and nematicidal properties.

The compounds of the formula (I) may have one or more asymmetric carbon atoms or stereoisomers on double bonds. Enantiomers or diastereomers may therefore be present. The invention embraces both the pure isomers and mixtures thereof. The mixtures of diastereomers can be separated into the isomers by customary methods, for example by selective crystallization from suitable solvents or by chromatography. Racemates can be separated into the enantiomers by customary methods.

The present invention also provides processes for preparing compounds of the formula I:

To prepare compounds of the formula (I) in which a) $X^1$=W, $X^2$=$NR^a$, $X^3$=$CR^bR^1$ and $R^a$, $R^b$ and $R^1$ are as defined above and W is oxygen, activated derivatives of the acid of the formula (II)

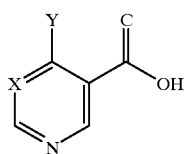

(II)

where X and Y are as defined above, are reacted in the presence of a base with a compound of the formula (III)

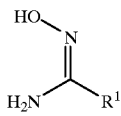

(III)

in which the radical $R^1$ is as defined in formula (I). Suitable activated derivatives are, for example, acyl halides, esters and anhydrides. Suitable bases are amines, such as triethylamine, diisopropylethylamine, pyridine or lutidine, alkali metal hydroxides, alkali metal alkoxides, such as sodium ethoxide or potassium tert-butoxide, or alkylmetal compounds, such as butyllithium.

Depending on the conditions, the reaction described above can be carried out as a one-step process or as a two-step process via intermediates of the formula (IV):

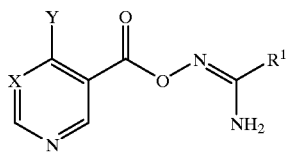

(IV)

Compounds of the formula (IV) can be cyclized to the 1,2,4-oxadiazoles by heating in an inert solvent at temperatures of up to 180° C.

Compounds of the formula (IV) are also directly obtainable from the acid of the formula (II) and amidoximes of the formula (III) by using a dehydrating reagent such as dicyclohexylcarbodiimide, 1-ethyl-3-(3-dimethylaminopropyl)carbodiimide or N,N'-carbonyldiimidazole.

Both acids of the formula (II) and amidoximes of the formula (III) are commercially available or can be prepared by methods known from the literature (see, for example: Houben-Weyl, Methoden der organischen Chemie, Volume X/4, pages 209–212; EP-A 0 580 374; G. F. Holland, J. N. Pereira, J. Med. Chem., 1967, 10, 149).

In the abovementioned case a) where W is sulfur, the compounds of the formula (I) can be obtained in a manner known from the literature by reaction of a compound of the formula (VII) with an electrophilic amination reagent, such as hydroxylamine-O-sulfonic acid (Y. Lin, S. A. Lang, S. R. Petty, J. Org. Chem. 1980, 45, 3750).

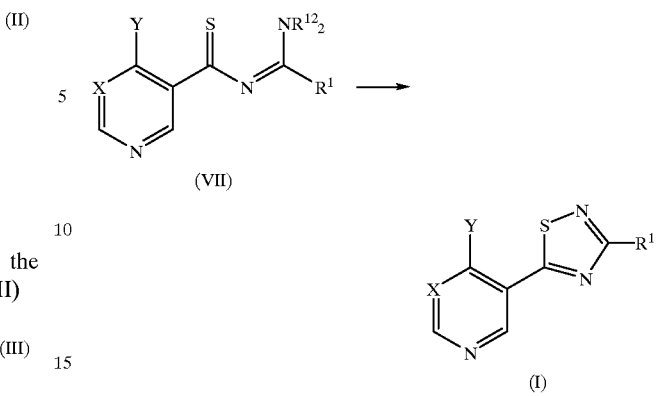

The compounds of the formula (VII) required as starting materials for this reaction can be prepared by reacting the thioamides of the formula (VIII) with dialkylamide dialkyl acetals, of formula (IX), where $R^1$ is as defined above and $R^{12}$ and $R^{13}$ are each $C_1$–$C_4$–alkyl.

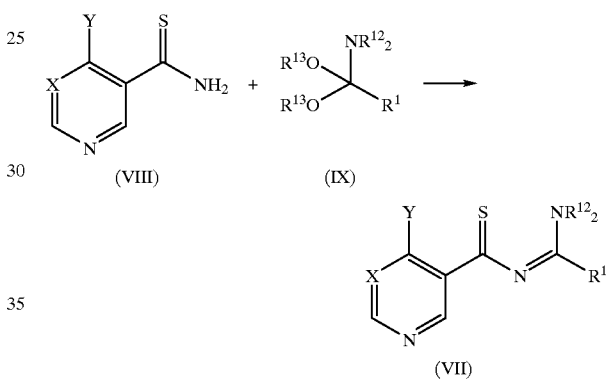

To prepare compounds of the formula (I) in which
 b) $X^1$=NR$^a$, $X^2$=CR$^b$R$^1$, $X^3$=W and R$^a$, R$^b$ and R$^1$ are as defined above, and W is oxygen, amidoximes of the formula (V) can be reacted with activated derivatives of the acids of the formula (VI) or with the acids of the formula (VI) themselves.

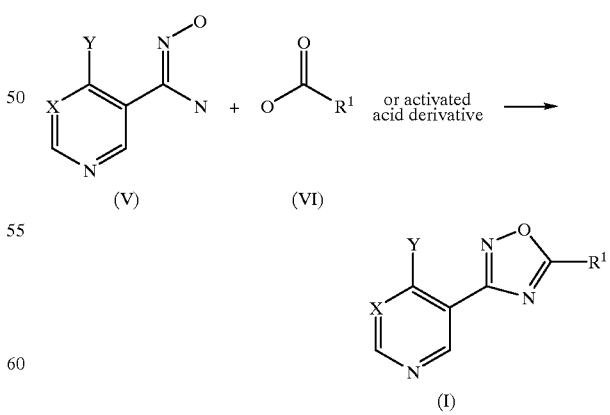

To prepare compounds of the formula (I) in which
 c) $X^1$=V, $X^2$=CR$^a$R$^1$, $X^3$=NR$^b$ and R$^a$, R$^b$ and R$^1$ are as defined above and V is sulfur, N,N'-diacylhydrazines of the formula (XIII) can be cyclized with a thiolation reagent, such as Lawesson's reagent (A. A. El-Barbary, S. Scheibyl, S. O. Lawesson, H. Fritz, Acta Chem. Scand. 1980, 597), in an inert solvent, such as toluene.

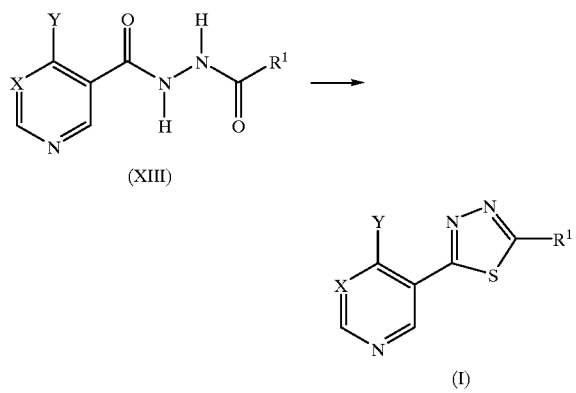

In the abovementioned case b) where W is oxygen, the compounds of the formula (I) can be prepared by reaction of acids of the formula (II) with hydrazines of the formula (X), in which $R^1$ is as defined above, using an activating reagent, such as phosphorus oxychloride or phosphorus pentachloride.

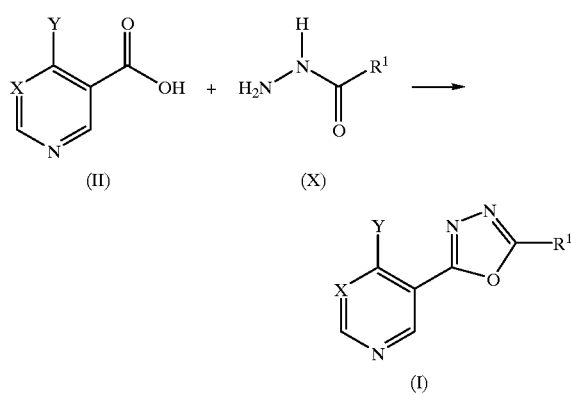

It is also possible to react acid hydrazides of the formula (XI) with ortho esters of the formula (XII) where $R^1$ is as defined above, and $R^{12}$ is $(C_1-C_4)$-alkyl.

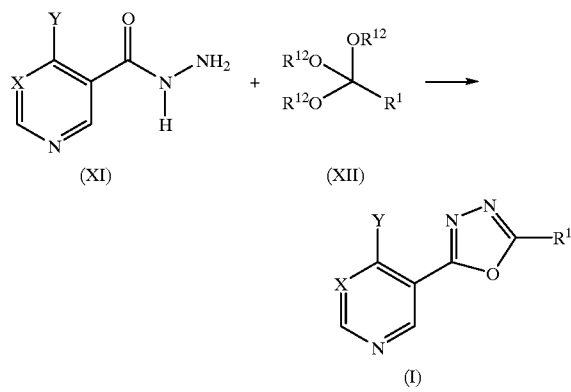

The reaction can be carried out with or without solvent and with or without an activating reagent. Suitable solvents are hydrocarbons, such as toluene, or ethers, such as 1,2-dimethoxyethane. A suitable activating reagent is, for example, phosphorus oxychloride. The reaction temperature is generally the reflux temperature of the solvent.

To prepare compounds of the formula (I) in which d) $X^1$=V, $X^2$=$CR^aR^2$, $X^3$=$CR^bR^3$ and $R^a$, $R^b$ and $R^3$ are as defined above and V is oxygen, compounds of the formula (XIV) are reacted with a dehydrating reagent.

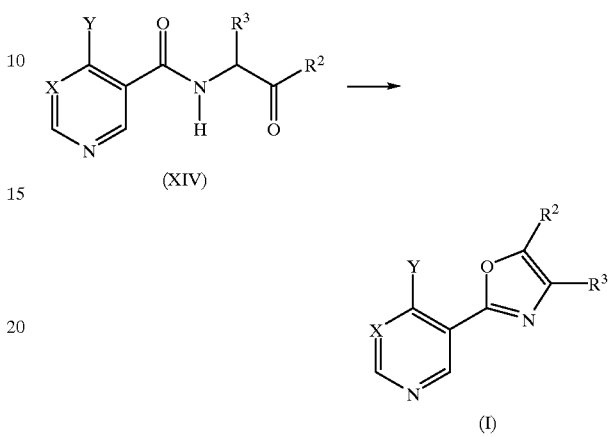

Suitable dehydrating reagents are inorganic acyl chlorides, such as phosphorus oxychloride or thionyl chloride, inorganic acids, such as sulfuric acid or polyphosphoric acid, or a mixture of phosphoric acid and acetic anhydride (Houben-Weyl, Methoden der organischen Chemie, Volume E8a, pages 935–941). The reaction can be carried out with or without a solvent. Suitable solvents are inert solvents, such as toluene, benzene, dimethoxyethane, dimethylformamide, dimethylacetamide and chlorobenzene. The reaction temperature is advantageously in a range between 50° C. and 150° C.

Compounds of the formula (XIV) can be obtained, for example, by oxidation of the corresponding hydroxyl compound of the formula (XV), it being possible to employ all reagents which are customarily used for this purpose in organic chemistry. (Milos Hudlický, "Oxidations in Organic Chemistry", ACS Monograph 186, American Chemical Society, Washington, D.C., 1990)

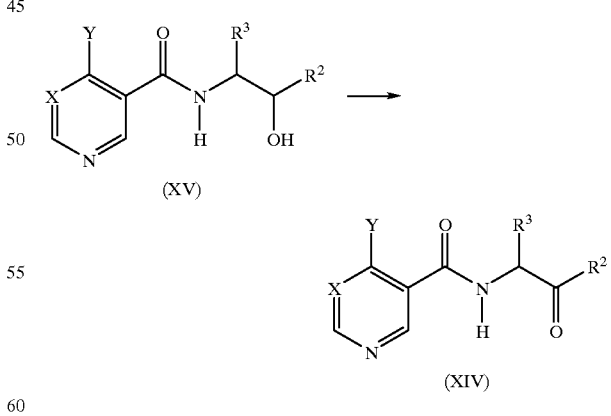

In the abovementioned case d) where V is sulfur, the compounds of the formula (I) can be prepared by condensation of thioamides of the formula (XVII) with carbonyl derivatives of the formula (XVIII), where Z is halogen, in particular chlorine or bromine, acyloxy or sulfonyloxy, in particular methanesulfonyloxy or tolylsulfonyloxy.

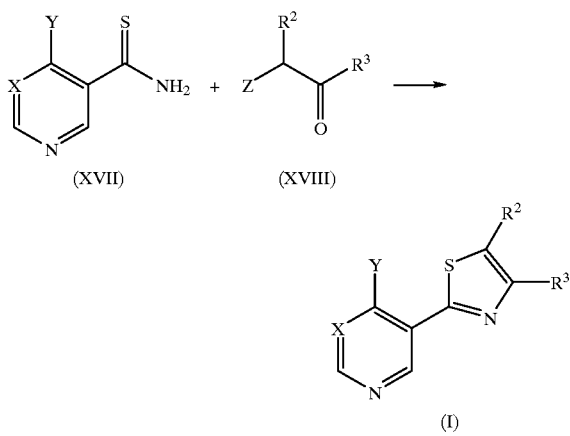

(XVII)    (XVIII)

↓

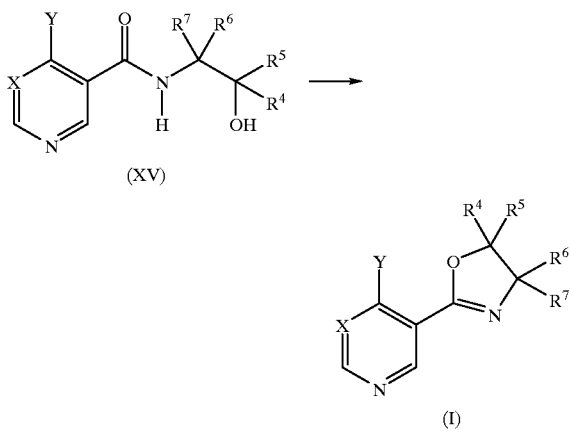

(I)

To prepare compounds of the formula (I) in which e) $X^1=V$, $X^2=CR^4R^5$, $X^3=CR^6R^7$ and $R^4$, $R^5$, $R^6$ and $R^7$ are as defined above and V is oxygen, compounds of the formula (XV) are reacted with cyclization reagents, such as Burgess' reagent (G. M. Atkins, E. M. Burgess, J. Am. Chem. Soc. 1968, 90, 4744.), in a solvent such as tetrahydrofuran and 1,4-dioxane, at a temperature which is in a range between room temperature and the reflux temperature of the solvent.

[structure XV]

↓

[structure I]

Compounds of the formual (XV) can be obtained by reacting activated derivatives of the acid in formula (II) with β-aminoalcohols of the formula (XVI), if appropriate in the presence of a base, such as, for example, triethylamine, in an inert solvent, such as, for example, dichlormethane.

(XVI)

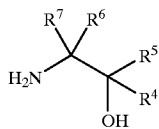

An acyl halide or an anhydride can be used as activated derivative of the acid. A number of β-aminoalcohols of the formula (XVI) are commercially available. For others, there is a large number of preparation procedures in the literature, for example a reduction of a-amino acids (B. M. Trost "Comprehensive Organic Synthesis, Reduction", Volume 8, Pergamon Press, Oxford, 1991). In the abovementioned case e) where V is sulfur, the compounds of the formula (I) can be prepared by reaction of thioamides of the formula (XVII) with compounds of the formula (XIX), the two substituents Z being as defined above and either identical or different (A. R. Katritzky "Comprehensive Heterocyclic Chemistry", Volume 6, pages 306–312, Pergamon Press, Oxford).

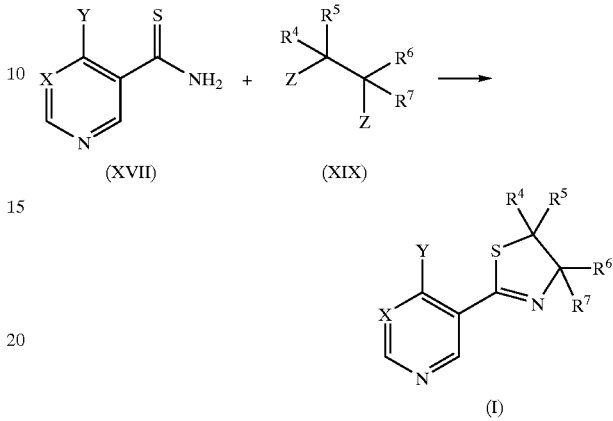

(XVII)    (XIX)

↓

[structure I]

Thioamides of the formula (XVII) are either commercially available or can be obtained by addition of hydrogen sulfide to the corresponding carbonitriles in the presence of a base (A. E. S. Fairfull, J. L. Lowe, D. A. Peak, J. Chem. Soc. 1952, 742).

For preparing compounds of the formula (I) in which f) $X^1=NR^a$, $X^2=CR^bR^1$, $X^3=NR^8$ and $R^a$, $R^b$, $R^1$ and $R^8$ are as defined above, hydrazides of the formula (XX)

(XX)

[structure XX]

are reacted with a compound of the formula (XXI) or with thioamides of the formula (XXII) (Houben-Weyl, Methoden der organischen Chemie, Volume E8d, pages 510–512).

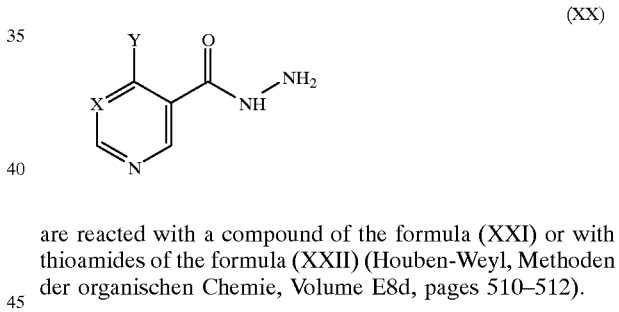

(XXI)

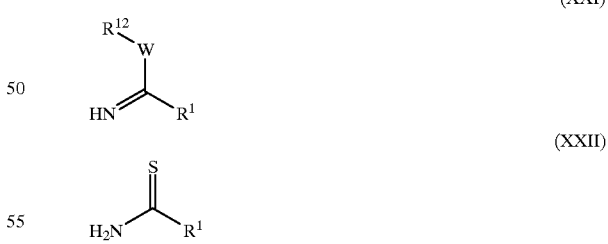

(XXII)

This reaction can be carried out with or without using a solvent, suitable solvents being alcohols, such as ethanol and propanol, or aromatic hydrocarbons, such as toluene and xylene. If the reaction is carried out in a solvent, the reaction temperature to be chosen is advantageously the reflux temperature of the solvent. If, on the other hand, the reaction is carried out without a solvent, it is possible to heat up to 200° C., if appropriate.

Once the group Q has been assembled, for example by condensation, cyclization or cycloaddition reactions, the radicals $R^1$ to $R^9$ may be derivatized further, if desired, employing the extensive arsenal of methods of organochemical synthesis.

To assemble compounds of the formula (I), in which m is 1, compounds of the formula (I) in which m is 0 can be treated with an oxidizing agent, such as, for example, meta-chloroperbenzoic acid.

The compounds of the formula (I) (also referred to as "active compounds" hereinbelow) have good plant tolerance, favorable homotherm toxicity and advantageous properties with respect to aquatic organisms and are suitable for controlling animal pests, in particular insects, arachnids (Acarina), helminths and molluscs, especially preferably for controlling insects and arachnids which are encountered in agriculture, in animal husbandry, in forests, in the preservation of stored products and materials and in the hygiene sector. They are active against normally sensitive and resistant species and all or individual stages of development. It has to be emphasized that the control of animal pests may be the result both of a toxic action of the compounds according to the invention and of a deterrant (repellant) action. The abovementioned pests include: From the order of the Acarina, for example, Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Eotetranychus spp., Oligonychus spp. and Eutetranychus spp.

From the order of the Isopoda, for example, Oniscus asselus, Armadium vulgar and Porcellio scaber.

From the order of the Diplopoda, for example, Blaniulus guttulatus.

From the order of the Chilopoda, for example, Geophilus carpophagus and Scutigera spp.

From the order of the Symphyla, for example, Scutigerella immaculate.

From the order of the Thysanura, for example, Lepisma saccharina.

From the order of the Collembola, for example, Onychiurus armatus.

From the order of the Orthoptera, for example, Blatta orientalis, Periplaneta americana, Leucophaea madeirae, Blatella germanica, Acheta domesticus, Gryllotalpa spp., Locusta migratoria migratorioides, Melanoplus differentialis and Schistocerca gregaria.

From the order of the Isoptera, for example, Reticulitermes spp. From the order of the Anoplura, for example, Phylloera vastatrix, Pemphigus spp., Pediculus humanus corporis, Haematopinus spp. and Linognathus spp.

From the order of the Mallophaga, for example, Trichodectes spp. and Damalinea spp.

From the order of the Thysanoptera, for example, Hercinothrips femoralis, Thrips tabaci and Frankliniella spp.

From the order of the Heteroptera, for example, Eurygaster spp., Dysdercus intermedius, Piesma quadrata, Cimex lectularius, Rhodnius prolixus and Triatoma spp.

From the order of the Homoptera, for example, Aleurodes brassicae, Bemisia tabaci, Trialeurodes vaporariorum, Aphis spp., Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelus bilobatus, Nephotettix cincticeps, Lecanium comi, Saissetia oleae, Laodelphax striatellus, Nilaparvata lugens, Aonidiella aurantii, Aspidiotus hederae, Pseudococcus spp. and Psylla spp.

From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanimna, Tortrix viridana, Cuaphalocrocis spp. and Manduca spp.

From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylloides chrysocephala, Epilachna varivestis, Atomaria spp., Oryzaephilus surinamensis, Anthonumus spp., Sitophilus spp., Otiorrhynchus sulcatus, Cosmopolites sordidus, Ceuthorrynchus assimilis, Hypera postica, Dermestes spp., Trogoderma, Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis, Costelytra zealandica and Lissorhoptus spp.

From the order of the Hymenoptera, for example, Diprion spp., Hoplocampa spp., Lasius spp., Monomorium pharaonis and Vespa spp.

From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hypobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa.

From the order of the Siphonaptera, for example, Xenopsylla cheopsis and Ceratophyllus spp.

From the order of the Arachnida, for example, Scorpio maurus and Latrodectus mactans.

From the class of helminths, for example, Haemonchus, Trichostrongulus, Ostertagia, Cooperia, Chabertia, Strongyloides, Oesophagostomum, Hyostrongulus, Ancylostoma, Ascaris and Heterakis, as well as Fasciola.

From the class of Gastropoda, for example, Deroceras spp., Arion spp., Lymnaea spp., Galba spp., Succinea spp., Biomphalaria spp., Bulinus spp. and Oncomelania spp.

From the class of Bivalva, for example, Dreissena spp.

The phytoparasitic nematodes which can be controlled according to the invention include, for example, the root-parasitic soil nematodes, such as, for example, those of the genera Meloidogyne (root gall nematodes, such as Meloidogyne incognita, Meloidogyne hapla and Meloidogyne javanica), Heterodera and Globodera (cyst-forming nematodes, such as Globodera rostochiensis, Globodera pallida and Heterodera trifolii) and of the genera Radopholus (such as Radopholus similis), Pratylenchus (such as Pratylenchus neglectus, Pratylenchus penetrans and Pratylenchus curvitatus), Tylenchulus (such as Tylenchulus semipenetrans), Tylenchorhynchus (such as Tylenchorhynchus dubius and Tylenchorhynchus claytoni), Rotylenchus (such as Rotylencus robustus), Heliocotylenchus (such as Heliocotylenchus multicinctus), Belonoaimus (such as Belonoaimus longicaudatus), Longidorus (such as Longidorus elongatus), Trichodorus (such as Trichodorus primitivus) and Xiphinema (such as Xiphinema index).

The nematode genera Ditylenchus (stem parasites, such as Ditylenchus dipsaci and Ditylenchus destructor), Aphelenchoides (leaf nematodes, such as Aphelenchoides ritzemabosi) and Anguina (blossom nematodes, such as Anguina tritici) can furthermore be controlled with the compounds according to the invention.

The invention also relates to compositions, in particular insecticidal and acaricidal compositions, which comprise the compounds of the formula (I) in addition to suitable formulation auxiliaries.

The compositions according to the invention in general comprise the active compounds of the formula (1) to the extent of 1 to 95% by weight. They can be formulated in various ways, depending on how this is determined by the biological and/or chemico-physical parameters. Suitable formulation possibilities are therefore:

Wettable powders (WP), emulsifiable concentrates (EC), aqueous solutions (SL), emulsions, sprayable solutions, oil- or water-based dispersions, suspension concentrates (SC), suspoemulsions (SE), dusting powders (DP), seed dressings, granules in the form of microgranules, sprayed granules, absorption granules and adsorption granules, water-dispersible granules (WG), ULV formulations, microcapsules, waxes or baits.

These individual types of formulation are known in principle and are described, for example, in: Winnacker-Kuchler, "Chemische Technologie" [Chemical Technology], Volume 7, C. Hauser Verlag Munich, 4th Edition 1986; van Falkenberg, "Pesticides Formulations", Marcel Dekker N.Y., 2nd Edition 1972–73; K. Martens, "Spray Drying Handbook", 3rd Edition 1979, G. Goodwin Ltd. London.

The necessary formulation auxiliaries, i.e. carrier substances and surface-acting substances, such as inert materials, surfactants, solvents and further additives, are likewise known and are described, for example, in: Watkins, "Handbook of Insecticide Dust Diluents and Carriers", 2nd Edition, Darland Books, Caldwell N.J.; H. v. Olphen, "Introduction to Clay Colloid Chemistry", 2nd Edition, J. Wiley & Sons, N.Y.; Marsden, "Solvents Guide", 2nd Edition, Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflachenaktive Athylenoxidaddukte" [Surface-active ethylene oxide adducts], Wiss. Verlagsgesell., Stuttgart 1967; Winnacker-Küchler, "Chemische Technologie" [Chemical Technology], Volume 7, C. Hauser Verlag Munich, 4th Edition 1986.

Combinations with other substances having a pesticidal action, fertilizers and/or growth regulators can be prepared on the basis of these formulations, for example in the form of a ready-to-use formulation or as a tank mix. Wettable powders are preparations which are uniformly dispersible in water and which, alongside the active compound, and in addition to a diluent or inert substance, also comprise wetting agents, for example polyethoxylated alkylphenols, polyethoxylated fatty alcohols or alkyl- or alkylphenolsulfonates, and dispersing agents, for example sodium ligninsulfonate or sodium 2,2'-dinaphthylmethane6,6'-disulfonate. Emulsifiable concentrates are prepared by dissolving the active compound in an organic solvent, for example butanol, cyclohexanone, dimethylformamide, xylene or also higher-boiling aromatics or hydrocarbons, with the addition of one or more emulsifiers. Emulsifiers which can be used are, for example: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting powders are obtained by grinding the active compound with finely divided solid substances, for example talc, naturally occurring clays, such as kaolin, bentonite and pyrophillite, or diatomaceous earth. Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the preparation of fertilizer granules—if desired as a mixture with fertilizers.

In wettable powders, the active compound concentration is generally about 10 to 90% by weight, the remainder to make up 100% by weight comprising customary formulation constituents. In emulsifiable concentrates, the active compound concentration can be about 5 to 80% by weight. Dust-like formulations usually comprise 5 to 20% by weight of active compound, and sprayable solutions about 2 to 20% by weight. In granules, the content of active compound partly depends on whether the active compound is present in liquid or solid form and what granulating auxiliaries, fillers and the like are used.

In addition, the active compound formulations mentioned comprise, if appropriate, the particular customary tackifiers, wetting agents, dispersing agents, emulsifiers, penetration agents, solvents, fillers or carriers.

For use, the concentrates in the commercially available form are diluted in the customary manner, if appropriate, for example by means of water in the case of wettable powders, emulsifiable concentrates, dispersions and in some cases also microgranules. Dust-like and granular formulations as well as sprayable solutions are usually not diluted further with additional inert substances before use.

The required amount applied varies with external conditions, such as temperature, humidity and the like. It can vary within wide limits, for example between 0.0005 and 10.0 kg/ha or more of active substance, but is preferably between 0.001 and 5 kg/ha.

The active compounds according to the invention can be present in their commercially available formulations and in the use forms prepared from these formulations as mixtures with other active compounds, such as insecticides, attractants, sterilizing agents, acaricides, nematicides, fungicides, growth-regulating substances or herbicides.

The pest control agents include, for example, phosphoric acid esters, carbamates, carboxylic acid esters, formamidines, tin compounds, substances produced by microorganisms and the like.

Preferred partners for the mixtures are 1. from the group of phosphorus compounds acephate, azamethiphos, azinphos-ethyl-, azinphosmethyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, O,O-1,2,2,2-tetrachloroethyl phosphorthioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos, primiphos-ethyl, pirimiphos-methyl, profenofos, propaphos, proetamphos, prothiofos, pyraclofos, pyridapenthion, quinalphos, suiprofos, temephos, terbufos, tetrachlorvinphos, thiometon, triazophos, trichlorphon, vamidothion;

2. from the group of carbamates aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenyl butyryl(methyl)carbamate, oxamyl, pirimicarb, propoxur, thiodicarb, thiofanox, ethyl 4,6,9-triaza-4-benzyl-6,10-dimethyl8-oxa-7-oxo-5, 11-dithia-9-dodecenoate (OK 135), 1-methylthio(ethylideneamino) N-methyl-N-(morpholinothio)carbamate (UC 51717);

3. from the group of carboxylic acid esters allethrin, alphametrin, 5-benzyl-3-furylmethyl (E)-(1 R)-cis, 2,2-dimethyl-3-(2-oxothiolan-3-ylidenemethyl) cyclopropanecarboxylate, bioallethrin, bioallethrin ((S)-cyclopentyl isomer), bioresmethrin, biphenate, (RS)-1-cyano-1-(6-phenoxy-2-pyridyl)methyl (1RS)-trans-3-(4-tert-butylphenyl)-2,2-dimethylcyclopropanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, pheothrin ((R) isomer), d-pralethrin, pyrethrins (naturally occurring products), resmethrin, tefluthrin, tetramethrin and tralomethrin;

4. from the group of amidines amitraz, chlordimeform;

5. from the group of tin compounds cyhexatin, fenbutatin oxide;

6. others abamectin, Bacillus thuringiensis, bensultap, binapacryl, bromopropylate, buprofezin, camphechlor, cartap, chlorbenzilate, chlorfluazuron, 2-(4-chlorophenyl)-4,5-diphenylthiophene (UBI-T 930), chlorfentezine, 2-naphthylmethyl cyclopropanecarboxylate (Ro 12-0470), cyromazin, N-(3,5-dichloro4-(1,1,2,3,3,3-hexafluoro-1-propyloxy)phenyl)carbamoyl)-2-chlorobenzocarboximide acid ethyl ester, dicofol, N-(N-(3,5-i-chloro4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2,4-xylidene, dinobuton, dinocap, endosulfan, ethofenprox, (4-ethoxyphenyl)(dimethyl)(3-(3-phenoxyphenyl)propyl) silane, (4-ethoxyphenyl)(3-(4-fluoro-3-phenoxyphenyl) propyl)dimethylsilane, fenoxycarb, 2-fluoro-5-(4-(4-ethoxyphenyl)4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramethyinon (AC 217300), ivermectin, 2-nitromethyl4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron, imidacloprid.

The abovementioned combination partners are known active compounds, and most of them are described in Ch. R. Worthing, S. B. Walker, The Pesticide Manual, 7th Edition (1983), British Crop Protection Council.

The active compound content of the use forms prepared from the commercially available formulations can be from 0.00000001 to 95% by weight of active compound, preferably between 0.00001 and 1 % by weight.

The active compounds are used in a customary manner appropriate for the use forms.

The active compounds according to the invention are also suitable for controlling endo- and ectoparasites in the veterinary medicine field and in the field of animal husbandry. The active compounds according to the invention are used here in a known manner, such as by oral use in the form of, for example, tablets, capsules, potions or granules, by means of dermal use in the form of, for example, dipping, spraying, pouring-on, spotting-on and dusting, and by parenteral use in the form of, for example, injection.

The novel compounds of the formula (I) can accordingly also particularly advantageously be used in livestock husbandry (for example cattle, sheep, pigs and poultry, such as chickens, geese and the like). In a preferred embodiment of the invention, the compounds are administered orally to the animals, if appropriate in suitable formulations (cf. above) and if appropriate with the drinking water or feed. Since excretion in the faeces takes place in an active manner, the development of insects in the faeces of the animals can be prevented very easily in this way. The dosages and formulations suitable in each case depend in particular on the species and the development stage of the stock animals and also on the pressure of infestation, and can easily be determined and specified by the customary methods. The novel compounds can be employed in cattle, for example, in dosages of 0.01 to 1 mg/kg of body weight.

In addition to the application methods mentioned hereinabove, the active compounds of the formula I according to the invention also have excellent systemic action. The active compounds can therefore also be introduced into the plants via below-ground and above-ground parts of plants (root, stem, leaf), when the active compounds are applied in liquid or solid form to the immediate surroundings of the plants (for example granules in soil application, application in flooded rice fields).

Furthermore, the active compounds according to the invention are particularly useful for treating vegetative and generatative propagation stock, such as, for example, seed of, for example, cereals, vegetables, cotton, rice, sugar beet and other crops and ornamentals, of bulbs, cuttings and tubers of other vegetatively propagated crops and ornamentals. To this end, treatment can be carried out prior to sowing or planting (for example by special seed coating techniques, by seed dressings in liquid or solid form or by seed box treatment), during sowing or planting or after sowing or planting by special application techniques (for example seed row treatment). Depending on the application, the amount of active compound applied can vary within a relatively wide range. In general, the application rates are between 1 g and 10 kg of active compound per hectare of soil area.

The examples below serve to illustrate the invention.

A. Formulation examples a) A dusting powder is obtained by mixing 10 parts by weight of active compound and 90 parts by weight of talc, as the inert substance, and comminuting the mixture in an impact mill.

b) A wettable powder which is readily dispersible in water is obtained by mixing 25 parts by weight of acitve compound, 65 parts by weight of kaolin-containing quartz, as the inert substance, 10 parts by weight of potassium ligninsulfonate and 1 part by weight of sodium oleoylmethyltauride, as wetting and dispersing agent and grinding the mixture in a pinned disk mill.

c) A dispersion concentrate which is readily dispersible in water is prepared by mixing 40 parts by weight of active compound with 7 parts by weight of a sulfosuccinic monoester, 2 parts by weight of a sodium ligninsulfonate and 51 parts by weight of water and grinding the mixture to a fineness of below 5 microns in a grinding bead mill.

d) An emulsifiable concentrate can be prepared from 15 parts by weight of active compound, 75 parts by weight of cyclohexane, as the solvent, and 10 parts by weight of ethoxylated nonylphenol (10 EO), as the emulsifier.

e) Granules can be prepared from 2 to 15 parts by weight of active compound and an inert granule carrier material, such as attapulgite, pumice granules and/or quartz sand. A suspension of the wettable powder from Example b) having a solids content of 30% is expediently used, and this is sprayed onto the surface of attapulgite granules and the components are dried and mixed intimately. The weight content of the wettable powder is approximately 5% and that of the inert carrier material is approximately 95% of the finished granules.

B. Chemical examples

Example No. 1

3-Isopropyl-5-(4-trifluoromethyl-3-pyridyl)-1,2,4oxadiazole (Table 1, No. 81)

2 g of methyl 4-trifluoromethylnicotinate and 1.56 g of isobutyramide oxime were initially charged in 15 ml of ethanol and cooled to 0° C. 10 ml of a 1.2 molar sodium ethoxide solution were added dropwise to this solution. The mixture was allowed to warm to room temperature over a period of two hours and stirring was then continued at this temperature until the reaction, according to TLC, had ended. The reaction mixture was concentrated and the residue was taken up in saturated ammonium chloride solution and extracted with diethyl ether. Chromatographic purification of the crude product gave the desired compound as a yellowish oil. $^1$H-NMR (CDCl$_3$, 300 MHz): d =1.41 (d, J=6.9 Hz, 6H), 3.22 (m, 1H), 7.78 (d, J=5 Hz, 1H), 9.02 (d, J=5 Hz, 1H), 9.34 (s, 1H) ppm.

Example No. 2

3-lsopropyl-5-(4-tifluoromethyl-5pydmidyl)-1,2,4-oxadiazole (Table 1, No. 189)

2 g of ethyl 4-trifluoromethylpyrimidine-5-carboxylate and 1.56 g of isobutyramide oxime were intiially charged in 15 ml of ethanol and cooled to 0° C. 10 ml of a 1.2 molar sodium ethoxide solution were added dropwise to this solution. The mixture was allowed to warm to room temperature over a period of one hour and then heated under reflux until the reaction, according to TLC, had ended. The reaction mixture was concentrated and the residue was taken up in saturated ammonium chloride solution and extracted with diethyl ether. Chromatographic purification of the crude product gave the desired compound as a yellowish oil. $^1$H-NMR (CDCl$_3$, 300 MHz): d =1.43 (d, J=7 Hz, 6H), 3.22 (hept., J=7 Hz, 1H), 9.52 (s, 1H), 9.58 (s, 1H) ppm.

Example No. 3

2-Methyl-5-(4-trfluoromethyl-3-pyridyl)-1,3,4-oxadiazole (Table 3, No. 549)

500 mg of 4-trifluoromethyinicotinic hydrazide were heated under reflux in 3.5 ml of triethyl orthoacetate for 2 hours. The reaction mixture was subsequently concentrated and the residue was carefully admixed with 2 ml of phosphorus oxychloride. The mixture was stirred at room temperature for 1 hour and then poured on ice and extracted with ethyl acetate. Chromatographic purification of the crude product obtained after drying and concentrating gave the desired compound as a yellowish oil.

$^1$H-NMR (CDCl$_3$, 300 MHz): d =2.67 (s, 3H), 7.75 (d, J=5 Hz, 1H), 8.99 (d, J=5 Hz, 1H), 9.34 (s, 1H) ppm.

Example No. 4

4-(Ethoxycarbonylmethyl)-2-(4-tifluoromethyl-3-pyridyl)thiazole (Table 4, No. 688)

500 mg of 4-trifluoromethylpyridine-3-thiocarboxamide and 440 mg of ethyl 4-chloroacetate were dissolved in 5 ml of dimethylformamide and heated at 100° C. for 4 hours. After cooling, the reaction mixture was poured onto ice-water and extracted with diethyl ether. The diethyl ether phase was dried (MgSO$_4$), filtered and concentrated and the residue was purified by chromatography. This gave the desired product in pure form as a colorless oil.

$^1$H-NMR (CDCl$_3$, 300 MHz): d =1.28 (t, J=7.5 Hz, 3H), 3.92 (s, 2H), 4.22 (q, J=7.5 Hz, 2H), 7.43 (s, 1H), 7.68 (d, J=5 Hz, 1H), 8.86 (d, J=5 Hz, 1H), 8.97 (s, 1H) ppm.

Example No. 5:

4-Ethyl-2-(4-tnfluoromethyl-3-pyndyl)oxazole (Table 4, No. 762)

2.6 g of 4-trifluoromethylnicotinic acid were admixed with 20 ml of thionyl chloride and heated at reflux temperature for 1 hour. After cooling, excess thionyl chloride was distilled off and the acyl chloride which remained as a pale yellow oil was taken up in 30 ml of dichloromethane. This solution was subsequently added dropwise to a solution of 2.4 9 of 2-amino-i-butanol and 2.75 g of triethylamine in 30 ml of dichloromethane cooled in an ice bath. After the addition had ended, stirring was continued at room temperature for approximately 2 hours. The mixture was poured into ammonium chloride solution and extracted with ethyl acetate. The crude N-(1-hydroxy-2-butyl)-4-trifluoromethyinicotinamide (2.3 g) obtained after drying and concentrating the ethyl acetate phase was dissolved at room temperature in 100 ml dichloromethane and mixed with 4.6 g of periodinan (Dess-Martin reagent). After the reaction had ended, according to TLC, the reaction mixture was concentrated and purified by column chromatography. The resulting 2-(trifluoromethylpyridin-3-amido)butanal (1.5 g) was dissolved in 30 ml of dimethylformamide, admixed with 2.72 g of phosphorus oxychloride and heated at 90° C. for 15 minutes. The solution was then poured onto ice and extracted with diethyl ether. Drying and concentration of the diethyl ether phase and chromatographic purification of the residue gave the product as a brownish oil.

$^1$H-NMR (CDCl$_3$, 300 MHz): d =1.3 (t, J=7.4 Hz, 3H), 2.66 (qd, J=7.4 Hz, J<1 Hz, 2H), 7.58 (t, J<1 Hz, 1H), 7.65 (d, J 5 Hz, 1H), 8.83 (d, J=5 Hz, 1H), 9.33 (d, J=5 Hz, 1H) ppm.

Example No. 6

4-Ethyl-2-(4-trifiuoromethyl-3-pyridyl)-4,5 dihydrooxazole (Table 5, No 876)

1 g of 4-trifluoromethylnicotinic acid was admixed with 8 ml of thionyl chloride and heated at reflux temperature for 1 hour. After cooling, excess thionyl chloride was distilled off and the acyl chloride which remained as a pale yellow oil was taken up in 10 ml of dichloromethane. This solution was subsequently added dropwise to a solution of 930 mg of 2-amino-1-butanol and 1.06 9 of triethylamine in 10 ml of dichloromethane cooled in an ice bath. After the addition had ended, stirring was continued for approximately 2 hours at room temperature. The mixture was poured into an ammonium chloride solution and extracted with ethyl acetate. The crude N-(1-hydroxy-2-butyl)-4-trifluoromethyinicotinamide (1.03 g) obtained after drying and concentration of the ethyl acetate phase was dissolved at room temperature in 6 ml of tetrahydrofuran and admixed with 1.09 g of N-[(triethylammonio)sulfonyl]-methylcarbamate (Burgess' reagent). The mixture was stirred at 60° C. for 3 hours. After cooling, the batch was concentrated and the residue was taken up in water and extracted with ethyl acetate. Chromatographic purification of the crude product gave the product as a colorless oil.

$^1$H-NMR (CDCl$_3$, 200 MHz): d =1.03 (t, J=7.6 Hz, 3H), 1.72 (m, 2H), 4.15 (t, J=7.5 Hz, 1H), 4.32 (m, 1H), 4.58 (t,

J=7.5 Hz, 1H), 7.6 (d, J=5 Hz, 1H), 8.87 (d, J=5 Hz, 1H), 9.06 (s, 1H) ppm.

Example No. 7

2-(3-Thienylmethyl)-5(4-tifluoromethyl-3-pyidyl)-1,3,4-oxadiazole (Table 3, No. 572)

880 mg of thiophene-3-acetic hydrazide were added to a solution of 960 mg of 4-trifluoromethylpyridine-3-carboxylic acid in 5 ml of phosphorus oxychloride, and the mixture was heated at reflux for 2 hours. The reaction mixture was subsequently added dropwise to ice-water, made neutral using concentrated ammonia solution and extracted with ethyl acetate. Drying ($Na_2SO_4$), concentration and chromatographic purification gave 624 mg of the desired product as a slightly brown oil.

$^1$H-NMR ($CDCl_3$, 200 MHz): d =4.38 (s, 2H), 7.1 (d, J=5 Hz, 1H), 7.23 (s, 1H), 7.37 (dd, J=5 Hz, J=3 Hz, 1H), 7.75 (d, J=6 Hz,$_1$H), 8.98 (d, J=6 Hz, 1H), 9.36 (s, 1H) ppm.

Example No. 8

5Methyl-3-(4-trifluoromethyl-3-pyridyl)-1H-1,2,4-triazole (Table 6, No. 947)

A mixture of 290 mg of ethylacetimidate hydrochloride and 100 mg of sodium hydroxide in 2 ml of ethanol was filtered and added to 500 mg of 4-trifluoromethyl-3-pyridinecarbohydrazide, and the mixture was heated under reflux for 3 hours. The reaction mixture was concentrated and the residue was suspended in xylene and refluxed for 4 hours. For work-up, the batch was diluted with ethyl acetate and washed with water. Chromatographic purification gave the pure product as a colorless solid.

$^1$H-NMR ($CDCl_3$, 300 MHz): d =2.58 (s, 3H), 7.64 (d, J=5 Hz,1H), 8.85 (d, J=5 Hz, 1H), 9.19 (s, 1H) ppm.

Example 9

3-(N-Isopropylcarbamoylmethyl)-5-(4-trfluoromethyl-3-pyridyl)-1,2,4-oxadiazole

Step 1: Tert-butyl 3-amino-3-(4-trifluoromethyl-3-pyridinecarbonyloxy-imino)propionate 30 g of 4-trifluoromethyl-3-pyridinecarboxylic acid is initially charged in 150 ml of dry THF and, a little at a time, admixed with 25.3 9 of carbonyl-diimidazole. The mixture is stirred at room temperature for 30 min. 27.2 g of tert-butoxycarbonylacetamide oxime dissolved in 150 ml of THF are then added dropwise. The mixture is stirred overnight, the solvent is evaporated and the residue is taken up in ethyl acetate, washed three times with 1 M sulfuric acid and once with saturated sodium bicarbonate solution. Concentration of the ethyl acetate phase gives 28 g of the product as a pale yellow solid.

$^1$H-NMR ($CDCl_3$, 300MHz): d =1.5 (s, 9H), 3.3 (s, 2H), 5.55 (br.s, 2H), 7.83 (d, J=5 Hz, 1H), 8.97 (d, J=5 Hz, 1H), 9.13 (s, 1H) ppm.

Step 2: 3-(Tert-butoxycarbonylmethyl)-5-(4-trifluoromethyl-3-pyridyl)-1,2,4-oxadiazole 28 g of tert-butyl 3-amino-3-(4-trifluoromethyl-3-pyridinecarbonyloxy-imino)propionate are dissolved in 380 ml of toluene and heated under reflux for 17 hours. Concentration and chromatographic purification of the residue over silica gel gives 14.4 g of the product as a pale brown oil.

$^1$H-NMR ($CDCl_3$, 300MHz): d =1.5 (s, 9H), 3.88 (s, 2H), 7.79 (d, J=5 Hz, 1H), 9.02 (d, J=5 Hz, 1H), 9.33 (s, 1H) ppm.

Step 3: 3-(Hydroxycarbonylmethyl)-5-(4-trifluoromethyl-3-pyridyl)-1,2,4-oxadiazole 12.4 g of 3-(tert-butoxycarbonylmethyl)-5-(4-trifluoromethyl-3-pyridyl)-1,2,4-oxadiazole are dissolved in 110 ml of dichloromethane and admixed with 57 ml of trifluoroacetic acid. The reaction mixture is stirred at room temperature for 1.5 hours and subsequently concentrated under reduced pressure. The residue is repeatedly taken up in dichloromethane and reconcentrated to remove any remaining trifluoroacetic acid. The mixture is finally triturated with diethyl ether, giving 8.1 g of the product as a white solid.

Step 4: 3-(N-Isopropylcarbamoylmethyl)-5-(4-trifluoromethyl-3-pyridyl)-1,2,4-oxadiazole 1 g of the product of the previous step are dissolved in 10 ml of THF and is mixed with 0.59 g of carbonyldiimidazole. The mixture is stirred at room temperature for 10 minutes, 0.22 g of isopropylamine are added dropwise and the mixture is allowed to react for a further 1.5 hours at room temperature with stirring. The reaction mixture is subsequently concentrated and the residue is taken up in ethyl acetate and washed three times with 1 M sulfuric acid and once with saturated sodium bicarbonate solution. The solid residue obtained after drying and concentrating the ethyl acetate phase is recrystallized from tert-butyl methyl ether, giving 0.46 g of the pure product as a pale yellow solid.

$^1$H-NMR ($CDCl_3$, 300 MHz): d =1.20 (d, J=7.6 Hz, 6H), 3.82 (s, 2H), 4.12 (m, 1H), 6.50 (br.s, 1H), 7.81 (d, J=5 Hz, 1H), 9.02 (d, J=5 Hz, 1H), 9.37 (s, 1H) ppm.

Example No. 10

3-(N,N-Dimethylaminocarbamoyl)-5-(4-tiifluoromethyl-3-pyridyl)-1,2,4-oxadiazole (Table 1, No. 502)

Step 1: Ethyl 2-amino-2-(4-trifluoromethyl-3-pyridinecarbonyloxyimino)acetate 17.3 g of carbonyidiimidazole are initially charged in 200 ml of 1,4-dioxane and, a little at a time, admixed with 20 g of 4-trifluoromethyl-3-pyridinecarboxylic acid. The mixture is stirred at room temperature for 1 h and subsequently heated to 45° C. for 2 h. After cooling to 30° C., 14.5 g of ethoxycarbonylformamide oxime are added and the mixture is stirred at 45° C. for 3 h. The precipitated solid is filtered off with suction and the filtrate is concentrated to 50 ml and, together with the solid, added to 250 ml of ice-water. The solid is filtered off with suction and dried at 50° C. under reduced pressure. This gives 28.7 9 of the product as a white solid of mp. 172–174° C.

Step 2: 3-Ethoxycarbonyl-5-(4-trifluoromethyl-3-pyridyl)-1,2,4-oxadiazole 20 g of ethyl 2-amino-2-(4-trifluormethyl-3-pyridinecarbonyloxyimino)-acetate are dissolved in 200 ml of a mixture of xylene and toluene and admixed with 5 g of Amberlyst 15. The mixture is boiled at 125–130° C. for 6 h using a Dean-Stark apparatus. After the reaction has ended, the mixture is cooled and admixed with a small amount of diethyl ether. The mixture is filtered with suction through a glass filter frit, and the solution is then concentrated. This gives 15.8 g of the product as a yellow oil.

Step 3: 5-(4-Trifluoromethyl-3-pyridyl)-1,2,4-oxadiazole-3-carboxylic acid 15.8 g of 3-ethoxycarbonyl-5-(4-trifluoromethyl-3-pyridyl)-1,2,4-oxadiazole are initially charged in 13 ml of methanol, and, with ice-cooling at 0° C., a solution of 2.8 g of lithium hydroxide in 50 ml of water is added dropwise. The mixture is stirred at room temperature for 2 h, 20 ml of ice-water are added and the mixture is extracted with 200 ml of diethyl ether. The aqueous phase is adjusted to pH=2 using dil. HCl, and the precipitated product is filtered off with suction. After drying, 13.8 g of 5-(4-trifluoromethyl-3-pyridyl)-1,2,4-oxadiazole-3-carboxylic acid are obtained as a white solid of mp. 157–159° C.

Step 4: N,N-Dimethyl-5-(4-trifluoromethyl-3-pyridyl)-1,2,4-oxadiazole-3-carboxamide 5.8 g of carbonyldiimidazole are initially charged in 90 ml of tetrahydrofuran and, a little at a time, admixed with 9 g of 5-(4-trifluoromethyl-3-pyridyl)-1,2,4-oxadiazole-3-carboxylic acid. The mixture is stirred at room temperature for 15 min and then heated at 50° C. for 2 h. After cooling to room temperature, 2.3 g of dimethylamine are introduced in a very gentle gas stream over a period of 2 h. After a reaction time of 12 h, the mixture is concentrated and taken up in 200 ml of diethyl ether. The mixture is washed with ice-cold half conc. hydrochloric acid solution, washed neutral with sat. sodium bicarbonate sol., dried over magnesium sulfate and concentrated under reduced pressure. This gives a slightly yellow oil which solidifies after a number of days to a solid of mp. 52–54° C.

In a similar manner, it is possible to prepare the compounds shown in Tables 1 to 6 below.

The abbreviations used denote

Ph: phenyl THP: 2-tetrahydropyranyl

TABLE 1

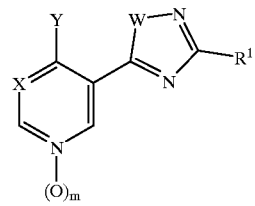

| No. | X  | Y            | m | W | R$^1$                    | m.p. [° C.] |
|-----|----|--------------|---|---|--------------------------|-------------|
| 1   | N  | CCl$_3$      | 0 | O | CH$_3$                   |             |
| 2   | N  | CCl$_3$      | 0 | O | CH$_2$CH$_3$             |             |
| 3   | N  | CCl$_3$      | 0 | O | COOCH$_2$CH$_3$          |             |
| 4   | CH | CCl$_3$      | 0 | O | CH$_3$                   |             |
| 5   | CH | CCl$_3$      | 0 | O | COOCH$_2$CH$_3$          |             |
| 6   | N  | (CF$_2$)$_3$CHCF$_2$ | 0 | O | CH$_3$            |             |
| 7   | N  | (CF$_2$)$_3$CHCF$_2$ | 0 | O | COOCH$_2$CH$_3$   |             |
| 8   | CH | (CF$_2$)$_3$CHCF$_2$ | 0 | O | CH$_3$            |             |
| 9   | CH | (CF$_2$)$_3$CHCF$_2$ | 0 | O | COOCH$_2$CH$_3$   |             |
| 10  | N  | (CF$_2$)$_3$CHCF$_2$ | 0 | S | CH$_2$COOC(CH$_3$)$_3$ |          |
| 11  | N  | (CF$_2$)$_3$CHCF$_2$ | 0 | S | CH$_2$CONHCH$_3$  |             |
| 12  | CH | (CF$_2$)$_3$CHCF$_2$ | 0 | S | (CH$_2$)$_2$CH$_3$ |            |
| 13  | CH | (CF$_2$)$_3$CHCF$_2$ | 0 | S | COOCH$_2$CH$_3$   |             |
| 14  | N  | (CF$_2$)$_2$CHCF$_2$ | 0 | O | CH$_2$CH$_3$      |             |
| 15  | N  | (CF$_2$)$_2$CHCF$_2$ | 0 | O | COOCH$_2$CH$_3$   |             |
| 16  | N  | (CF$_2$)$_2$CHCF$_2$ | 0 | O | OH                |             |
| 17  | N  | (CF$_2$)$_2$CHCF$_2$ | 0 | O | OCH$_3$           |             |
| 18  | CH | (CF$_2$)$_2$CHCF$_2$ | 0 | O | CH$_3$            |             |
| 19  | CH | (CF$_2$)$_2$CHCF$_2$ | 0 | O | COOCH$_2$CH$_3$   |             |
| 20  | CH | (CF$_2$)$_2$CHCF$_2$ | 0 | O | OH                |             |
| 21  | CH | (CF$_2$)$_2$CHCF$_2$ | 0 | O | NHCH$_3$          |             |
| 22  | N  | CF$_2$CF$_3$ | 0 | O | CH$_3$                   |             |
| 23  | N  | CF$_2$CF$_3$ | 0 | O | CH$_2$CH$_3$             |             |
| 24  | N  | CF$_2$CF$_3$ | 0 | O | (CH$_2$)$_2$CH$_3$       |             |
| 25  | N  | CF$_2$CF$_3$ | 0 | O | CH(CH$_3$)$_2$           |             |
| 26  | N  | CF$_2$CF$_3$ | 0 | O | Cyclo-C$_6$H$_{11}$      |             |
| 27  | N  | CF$_2$CF$_3$ | 0 | O | CH$_2$C=CH$_2$           |             |
| 28  | N  | CF$_2$CF$_3$ | 0 | O | CH$_2$C≡CH               |             |
| 29  | N  | CF$_2$CF$_3$ | 0 | O | CH$_2$CH$_2$C≡CH         |             |
| 30  | N  | CF$_2$CF$_3$ | 0 | O | CH$_2$C≡CCH$_2$CH$_3$    |             |
| 31  | N  | CF$_2$CF$_3$ | 0 | O | (CH$_2$)$_4$C≡CH         |             |
| 32  | N  | CF$_2$CF$_3$ | 0 | O | CHFCF$_3$                |             |
| 33  | N  | CF$_2$CF$_3$ | 0 | O | COOCH$_2$CH$_3$          |             |
| 34  | N  | CF$_2$CF$_3$ | 0 | O | CH$_2$COOC(CH$_3$)$_3$   |             |
| 35  | N  | CF$_2$CF$_3$ | 0 | O | CH$_2$CONHCH$_3$         |             |
| 36  | N  | CF$_2$CF$_3$ | 0 | O | NH$_2$                   |             |
| 37  | N  | CF$_2$CF$_3$ | 0 | O | NHCH$_2$CH$_3$           |             |
| 38  | CH | CF$_2$CF$_3$ | 0 | O | CH$_3$                   |             |
| 39  | CH | CF$_2$CF$_3$ | 0 | O | CH$_2$CH$_3$             |             |
| 40  | CH | CF$_2$CF$_3$ | 0 | O | (CH$_2$)$_2$CH$_3$       |             |
| 41  | CH | CF$_2$CF$_3$ | 0 | O | CH(CH$_3$)$_2$           |             |
| 42  | CH | CF$_2$CF$_3$ | 0 | O | Cyclo-C$_6$H$_{11}$      |             |
| 43  | CH | CF$_2$CF$_3$ | 0 | O | CH$_2$C=CH$_2$           |             |
| 44  | CH | CF$_2$CF$_3$ | 0 | O | CH$_2$COOC(CH$_3$)$_3$   |             |
| 45  | CH | CF$_2$CF$_3$ | 0 | O | NH$_2$                   |             |
| 46  | CH | CF$_2$CF$_3$ | 0 | O | NHCOCH$_3$               |             |
| 47  | CH | CF$_2$CF$_3$ | 0 | O | NHCOCH$_2$CH$_3$         |             |
| 48  | N  | CF$_2$CF$_3$ | 0 | S | CH$_3$                   |             |
| 49  | N  | CF$_2$CF$_3$ | 0 | S | CH$_2$CH$_3$             |             |
| 50  | N  | CF$_2$CF$_3$ | 0 | S | (CH$_2$)$_2$CH$_3$       |             |
| 51  | N  | CF$_2$Cl     | 0 | O | CH$_3$                   |             |
| 52  | N  | CF$_2$Cl     | 0 | O | CH$_2$CH$_3$             |             |
| 53  | N  | CF$_2$Cl     | 0 | O | (CH$_2$)$_2$CH$_3$       |             |
| 54  | N  | CF$_2$Cl     | 0 | O | CH(CH$_3$)$_2$           |             |
| 55  | N  | CF$_2$Cl     | 0 | O | CH$_2$COOC(CH$_3$)$_3$   |             |

TABLE 1-continued

| No. | X | Y | m | W | R¹ | m.p. [° C.] |
|---|---|---|---|---|---|---|
| 56 | N | $CF_2Cl$ | 0 | O | $CH_2CONHCH_3$ | |
| 57 | N | $CF_2Cl$ | 0 | O | OH | |
| 58 | N | $CF_2Cl$ | 0 | O | $OCH_3$ | |
| 59 | N | $CF_2Cl$ | 0 | O | $OCH_2CH_3$ | |
| 60 | N | $CF_2Cl$ | 0 | O | $NHCH_3$ | |
| 61 | CH | $CF_2Cl$ | 0 | O | $CH_3$ | |
| 62 | CH | $CF_2Cl$ | 0 | O | $CH_2CH_3$ | |
| 63 | CH | $CF_2Cl$ | 0 | O | $(CH_2)_2CH_3$ | |
| 64 | CH | $CF_2Cl$ | 0 | O | $CH(CH_3)_2$ | |
| 65 | CH | $CF_2Cl$ | 0 | O | $CH_2COOC(CH_3)_3$ | |
| 66 | CH | $CF_2Cl$ | 0 | O | $CH_2CONHCH_3$ | |
| 67 | CH | $CF_2Cl$ | 0 | O | OH | |
| 68 | CH | $CF_2Cl$ | 0 | O | $OCH_3$ | |
| 69 | CH | $CF_2Cl$ | 0 | O | $OCH_2CH_3$ | |
| 70 | CH | $CF_2Cl$ | 0 | O | $NHCH_3$ | |
| 71 | CH | $CF_2Cl$ | 0 | O | Cyclo-$C_6H_{11}$ | |
| 72 | CH | $CF_2Cl$ | 0 | O | $CH_2C=CH_2$ | |
| 73 | CH | $CF_2Cl$ | 0 | O | $COOCH_2CH_3$ | |
| 74 | CH | $CF_2Cl$ | 0 | O | $CH_2COOC(CH_3)_3$ | |
| 75 | CH | $CF_2Cl$ | 0 | O | $CH_2CONHCH_3$ | |
| 76 | CH | $CF_2Cl$ | 0 | O | $OCH_3$ | |
| 77 | CH | $CF_2Cl$ | 0 | O | $NHCH_3$ | |
| 78 | CH | $CF_3$ | 0 | O | $CH_3$ | oil |
| 79 | CH | $CF_3$ | 0 | O | $CH_2CH_3$ | oil |
| 80 | CH | $CF_3$ | 0 | O | $(CH_2)_2CH_3$ | oil |
| 81 | CH | $CF_3$ | 0 | O | $CH(CH_3)_2$ | oil |
| 82 | CH | $CF_3$ | 0 | O | Cyclo-$C_3H_5$ | oil |
| 83 | CH | $CF_3$ | 0 | O | $(CH_2)_3CH_3$ | oil |
| 84 | CH | $CF_3$ | 0 | O | $CH(CH_3)CH_2CH_3$ | oil |
| 85 | CH | $CF_3$ | 0 | O | $CH_2CH(CH_3)_2$ | oil |
| 86 | CH | $CF_3$ | 0 | O | $C(CH_3)_3$ | oil |
| 87 | CH | $CF_3$ | 0 | O | Cyclo-$C_4H_7$ | |
| 88 | CH | $CF_3$ | 0 | O | $(CH_2)_4CH_3$ | oil |
| 89 | CH | $CF_3$ | 0 | O | $CH(CH_3)(CH_2)_2CH_3$ | |
| 90 | CH | $CF_3$ | 0 | O | $(CH_2)_2CH(CH_3)_2$ | |
| 91 | CH | $CF_3$ | 0 | O | $CH_2C(CH_3)_3$ | |
| 92 | CH | $CF_3$ | 0 | O | Cyclo-$C_5H_9$ | oil |
| 93 | CH | $CF_3$ | 0 | O | $(CH_2)_5CH_3$ | |
| 94 | CH | $CF_3$ | 0 | O | $O(CH_2CH_3)_2CH_3$ | |
| 95 | CH | $CF_3$ | 0 | O | Cyclo-$C_6H_{11}$ | |
| 96 | CH | $CF_3$ | 0 | O | $(CH_2)_6CH_3$ | |
| 97 | CH | $CF_3$ | 0 | O | $CH(CH_3)(CH_2)_4CH_3$ | |
| 98 | CH | $CF_3$ | 0 | O | Cyclo-$C_7H_{13}$ | |
| 99 | CH | $CF_3$ | 0 | O | $CH_2$-cyclo-$C_6H_{11}$ | |
| 100 | CH | $CF_3$ | 0 | O | 2-Norbornyl | |
| 101 | CH | $CF_3$ | 0 | O | $(CH_2)_7CH_3$ | |
| 102 | CH | $CF_3$ | 0 | O | $CH(CH_2CH_3)(CH_2)_5CH_3$ | |
| 103 | CH | $CF_3$ | 0 | O | $(CH_2)_8CH_3$ | |
| 104 | CH | $CF_3$ | 0 | O | $(CH_2)_3$-cyclo-$C_6H_{11}$ | |
| 105 | CH | $CF_3$ | 0 | O | $(CH_2)_9CH_3$ | |
| 106 | CH | $CF_3$ | 0 | O | 1-Adamantyl | |
| 107 | CH | $CF_3$ | 0 | O | $(CH_2)_{10}CH_3$ | |
| 108 | CH | $CF_3$ | 0 | O | $(CH_2)_{11}CH_3$ | |
| 109 | CH | $CF_3$ | 0 | O | $CH(CH_3)(CH_2)_9CH_3$ | |
| 110 | CH | $CF_3$ | 0 | O | $(CH_2)_{12}CH_3$ | |
| 111 | CH | $CF_3$ | 0 | O | $(CH_2)_{13}CH_3$ | |
| 112 | CH | $CF_3$ | 0 | O | $(CH_2)_{14}CH_3$ | |
| 113 | CH | $CF_3$ | 0 | O | $(CH_2)_{15}CH_3$ | |
| 114 | CH | $CF_3$ | 0 | O | $(CH_2)_{17}CH_3$ | |
| 115 | CH | $CF_3$ | 0 | O | $(CH_2)_{19}CH_3$ | |
| 116 | CH | $CF_3$ | 0 | O | CHO | |
| 117 | CH | $CF_3$ | 0 | O | $CH=CH_2$ | oil |
| 118 | CH | $CF_3$ | 0 | O | $CH_2C=C(CH_3)_2$ | |
| 119 | CH | $CF_3$ | 0 | O | $CH_2CH_2C=CH_2$ | |
| 120 | CH | $CF_3$ | 0 | O | $CH_2C=CH_2$ | |
| 121 | CH | $CF_3$ | 0 | O | $C(CH_3)=CH_2$ | |

TABLE 1-continued

| No. | X | Y | m | W | R$^1$ | m.p. [° C.] |
|---|---|---|---|---|---|---|
| 122 | CH | CF$_3$ | 0 | O | (E)-CH$_2$CH=CHCH$_2$CH$_3$ | |
| 123 | CH | CF$_3$ | 0 | O | (Z)-CH$_2$CH=CHCH$_2$CH$_3$ | |
| 124 | CH | CF$_3$ | 0 | O | (CH$_2$)$_5$C=CH$_2$ | |
| 125 | CH | CF$_3$ | 0 | O | C(=CHCH$_3$)CH$_3$ | 62–64 |
| 126 | CH | CF$_3$ | 0 | O | Geranyl | |
| 127 | CH | CF$_3$ | 0 | O | 3-Menthyl | |
| 128 | CH | CF$_3$ | 0 | O | C≡CH | |
| 129 | CH | CF$_3$ | 0 | O | CH$_2$C≡CH | |
| 130 | CH | CF$_3$ | 0 | O | CH$_2$CH$_2$C≡CH | |
| 131 | CH | CF$_3$ | 0 | O | CH$_2$CH$_2$C≡CH | |
| 132 | CH | CF$_3$ | 0 | O | (CH$_2$)$_4$C≡CH | |
| 133 | CH | CF$_3$ | 0 | O | CHFCF$_3$ | oil |
| 134 | CH | CF$_3$ | 0 | O | COOCH$_2$CH$_3$ | oil |
| 135 | CH | CF$_3$ | 0 | O | CH$_2$CH$_2$OH | oil |
| 136 | CH | CF$_3$ | 0 | O | CH$_2$CH$_2$OCH$_3$ | oil |
| 137 | CH | CF$_3$ | 0 | O | CH$_2$COOC(CH$_3$)$_3$ | oil |
| 138 | CH | CF$_3$ | 0 | O | CH$_2$SC$_6$H$_5$ | oil |
| 139 | CH | CF$_3$ | 0 | O | CH$_2$CONHCH$_3$ | 109–111 |
| 140 | CH | CF$_3$ | 0 | O | CH$_2$CH(CH)CH$_2$OH | |
| 141 | CH | CF$_3$ | 0 | O | CH$_2$COCH$_3$ | |
| 142 | CH | CF$_3$ | 0 | O | COCH$_3$ | |
| 143 | CH | CF$_3$ | 0 | O | CH$_2$OC$_6$H$_5$ | |
| 144 | CH | CF$_3$ | 0 | O | COC$_6$H$_5$ | |
| 145 | CH | CF$_3$ | 0 | O | CO(4-Cl)-C$_6$H$_4$ | |
| 146 | CH | CF$_3$ | 0 | O | CF$_2$CH$_3$ | |
| 147 | CH | CF$_3$ | 0 | O | CH$_2$CN | |
| 148 | CH | CF$_3$ | 0 | O | CH$_2$CH$_2$CN | |
| 149 | CH | CF$_3$ | 0 | O | CH$_2$CH(—O—)CH$_2$ | |
| 150 | CH | CF$_3$ | 0 | O | CH$_2$(4-OCH$_3$)C$_6$H$_5$ | |
| 151 | CH | CF$_3$ | 0 | O | CH$_2$-cyclo-(4-Oxo)-C$_6$H$_8$ | |
| 152 | CH | CF$_3$ | 0 | O | CH$_2$CH(CH)CH$_2$SC$_6$H$_5$ | |
| 153 | CH | CF$_3$ | 0 | O | CH$_2$CH$_2$Si(CH$_3$)$_3$ | |
| 154 | CH | CF$_3$ | 0 | O | CH=CF$_2$ | |
| 155 | CH | CF$_3$ | 0 | O | CCl=CHCl | |
| 156 | CH | CF$_3$ | 0 | O | 2-Pyridyl | 99–101 |
| 157 | CH | CF$_3$ | 0 | O | 2-Furyl | |
| 158 | CH | CF$_3$ | 0 | O | 2-Thienyl | 106–108 |
| 159 | CH | CF$_3$ | 0 | O | CH$_2$C≡CCH$_2$CH$_2$OTHP | |
| 160 | CH | CF$_3$ | 0 | O | CH$_2$CH$_2$Cl | oil |
| 161 | CH | CF$_3$ | 0 | O | Si(CH$_3$)$_3$ | |
| 162 | CH | CF$_3$ | 0 | O | OC$_6$H$_5$ | |
| 163 | CH | CF$_3$ | 0 | O | OH | |
| 164 | CH | CF$_3$ | 0 | O | OCH$_3$ | |
| 165 | CH | CF$_3$ | 0 | O | OCH$_2$CH$_3$ | |
| 166 | CH | CF$_3$ | 0 | O | OCHF$_2$ | |
| 167 | CH | CF$_3$ | 0 | O | OCH$_2$C$_6$H$_5$ | |
| 168 | CH | CF$_3$ | 0 | O | CH$_2$SCH$_3$ | 48–49 |
| 169 | CH | CF$_3$ | 0 | O | SC$_6$H$_5$ | |
| 170 | CH | CF$_3$ | 0 | O | SeC$_6$H$_5$ | |
| 171 | CH | CF$_3$ | 0 | O | NH$_2$ | 116–118 |
| 172 | CH | CF$_3$ | 0 | O | NHCH$_3$ | |
| 173 | CH | CF$_3$ | 0 | O | NHCH$_2$CH$_3$ | |
| 174 | CH | CF$_3$ | 0 | O | N(CH$_2$CH$_3$)$_2$ | |
| 175 | CH | CF$_3$ | 0 | O | CONHCH$_2$C=CH$_2$ | 105–107 |
| 176 | CH | CF$_3$ | 0 | O | Cl | |
| 177 | CH | CF$_3$ | 0 | O | Br | |
| 178 | CH | CF$_3$ | 0 | O | CONH$_2$ | 206–208 |
| 179 | CH | CF$_3$ | 0 | O | NHCOCH$_3$ | 129–131 |
| 180 | CH | CF$_3$ | 0 | O | NHCOCH$_2$CH$_3$ | |
| 181 | CH | CF$_3$ | 0 | O | OSO$_2$CH$_3$ | |
| 182 | CH | CF$_3$ | 0 | O | SOCH$_2$(4-Br)—C$_6$H$_4$ | |
| 183 | CH | CF$_3$ | 0 | O | N(CH$_3$)COOCH$_2$C$_6$H$_5$ | |
| 184 | CH | CF$_3$ | 0 | O | NHNH$_2$ | |
| 185 | CH | CF$_3$ | 0 | O | NHN(CH$_3$)$_2$ | |
| 186 | N | CF$_3$ | 0 | O | CH$_3$ | |
| 187 | N | CF$_3$ | 0 | O | CH$_2$CH$_3$ | oil |

TABLE 1-continued

| No. | X | Y | m | W | R¹ | m.p. [° C.] |
|---|---|---|---|---|---|---|
| 188 | N | $CF_3$ | 0 | O | $(CH_2)_2CH_3$ | oil |
| 189 | N | $CF_3$ | 0 | O | $CH(CH_3)_2$ | oil |
| 190 | N | $CF_3$ | 0 | O | $(CH_2)_3CH_3$ | oil |
| 191 | N | $CF_3$ | 0 | O | $CH_2CH(CH_3)_2$ | oil |
| 192 | N | $CF_3$ | 0 | O | $C(CH_3)_3$ | |
| 193 | N | $CF_3$ | 0 | O | $(CH_2)_4CH_3$ | oil |
| 194 | N | $CF_3$ | 0 | O | $CH(CH_3)(CH_2)_2CH_3$ | |
| 195 | N | $CF_3$ | 0 | O | $CH_2C(CH_3)_3$ | |
| 196 | N | $CF_3$ | 0 | O | Cyclo-$C_5H_9$ | |
| 197 | N | $CF_3$ | 0 | O | $(CH_2)_5CH_3$ | |
| 198 | N | $CF_3$ | 0 | O | Cyclo-$C_6H_{11}$ | |
| 199 | N | $CF_3$ | 0 | O | $CH(CH_3)(CH_2)_4CH_3$ | |
| 200 | N | $CF_3$ | 0 | O | $CH_2$-cyclo-$C_6H_{11}$ | |
| 201 | N | $CF_3$ | 0 | O | $(CH_2)_7CH_3$ | |
| 202 | N | $CF_3$ | 0 | O | $(CH_2)_8CH_3$ | |
| 203 | N | $CF_3$ | 0 | O | $(CH_2)_9CH_3$ | |
| 204 | N | $CF_3$ | 0 | O | $CH(CH_3)(CH_2)_9CH_3$ | |
| 205 | N | $CF_3$ | 0 | O | $(CH_2)_{15}CH_3$ | |
| 206 | N | $CF_3$ | 0 | O | $(CH_2)_{17}CH_3$ | |
| 207 | N | $CF_3$ | 0 | O | $(CH_2)_{19}CH_3$ | |
| 208 | N | $CF_3$ | 0 | O | $CH_2CH=C(CH_3)_2$ | |
| 209 | N | $CF_3$ | 0 | O | $CH_2CH_2CH=CH_2$ | |
| 210 | N | $CF_3$ | 0 | O | $CH_2CH=CH_2$ | |
| 211 | N | $CF_3$ | 0 | O | (Z)-$CH_2CH=CHCH_2CH_3$ | |
| 212 | N | $CF_3$ | 0 | O | $(CH_2)_5CH=CH_2$ | |
| 213 | N | $CF_3$ | 0 | O | $CH_2C\equiv CH$ | |
| 214 | N | $CF_3$ | 0 | O | $CH_2C\equiv CCH_2CH_3$ | |
| 215 | N | $CF_3$ | 0 | O | $CHFCF_3$ | |
| 216 | N | $CF_3$ | 0 | O | $COOCH_2CH_3$ | |
| 217 | N | $CF_3$ | 0 | O | $CH_2CH_2OH$ | |
| 218 | N | $CF_3$ | 0 | O | $CH_2CH_2OCH_3$ | |
| 219 | N | $CF_3$ | 0 | O | $CH_2COOC(CH_3)_3$ | |
| 220 | N | $CF_3$ | 0 | O | $CH_2SC_6H_5$ | |
| 221 | N | $CF_3$ | 0 | O | $CH_2CONHCH_3$ | |
| 222 | N | $CF_3$ | 0 | O | $CH_2CH(CH)CH_2OH$ | |
| 223 | N | $CF_3$ | 0 | O | CHO | |
| 224 | N | $CF_3$ | 0 | O | $COCH_3$ | |
| 225 | N | $CF_3$ | 0 | O | $CH_2OC_6H_5$ | |
| 226 | N | $CF_3$ | 0 | O | $COC_6H_5$ | |
| 227 | N | $CF_3$ | 0 | O | $CF_2CH_3$ | |
| 228 | N | $CF_3$ | 0 | O | $CH_2CN$ | |
| 229 | N | $CF_3$ | 0 | O | $CH_2CH_2CN$ | |
| 230 | N | $CF_3$ | 0 | O | $CH=CF_2$ | |
| 231 | N | $CF_3$ | 0 | O | 2-Furyl | |
| 232 | N | $CF_3$ | 0 | O | $CH_2C\equiv C-I$ | |
| 233 | N | $CF_3$ | 0 | O | OH | |
| 234 | N | $CF_3$ | 0 | O | $OCH_3$ | |
| 235 | N | $CF_3$ | 0 | O | $OCH_2CH_3$ | |
| 236 | N | $CF_3$ | 0 | O | $OCHF_2$ | |
| 237 | N | $CF_3$ | 0 | O | $OCH_2C_6H_5$ | |
| 238 | N | $CF_3$ | 0 | O | $SC_6H_5$ | |
| 239 | N | $CF_3$ | 0 | O | $NH_2$ | |
| 240 | N | $CF_3$ | 0 | O | $NHCH_3$ | |
| 241 | N | $CF_3$ | 0 | O | $NHCH_2CH_3$ | |
| 242 | N | $CF_3$ | 0 | O | $N(CH_2CH_3)_2$ | |
| 243 | N | $CF_3$ | 0 | O | $N(CH_2CN)_2$ | |
| 244 | N | $CF_3$ | 0 | O | $N(CH_3)_2$ | |
| 245 | N | $CF_3$ | 0 | O | $NHCOCH_3$ | |
| 246 | N | $CF_3$ | 0 | O | $NHCOCH_2CH_3$ | |
| 247 | N | $CF_3$ | 0 | O | $OSO_2CH_3$ | |
| 248 | N | $CF_3$ | 0 | O | $NHNH_2$ | |
| 249 | CH | $CF_3$ | 0 | S | $CH_3$ | |
| 250 | CH | $CF_3$ | 0 | S | $CH_2CH_3$ | |
| 251 | CH | $CF_3$ | 0 | S | $(CH_2)_2CH_3$ | |
| 252 | CH | $CF_3$ | 0 | S | CHO | |
| 253 | CH | $CF_3$ | 0 | S | $CHFCF_3$ | |

TABLE 1-continued

| No. | X | Y | m | W | R¹ | m.p. [° C.] |
|---|---|---|---|---|---|---|
| 254 | CH | CF$_3$ | 0 | S | CH$_2$C≡CH | |
| 255 | CH | CF$_3$ | 0 | S | COOCH$_2$CH$_3$ | |
| 256 | CH | CF$_3$ | 0 | S | CH$_2$COOC(CH$_3$)$_3$ | |
| 257 | CH | CF$_3$ | 0 | S | CH$_2$CN | |
| 258 | CH | CF$_3$ | 0 | S | SeC$_6$H$_5$ | |
| 259 | N | CF$_3$ | 0 | S | CH$_3$ | |
| 260 | N | CF$_3$ | 0 | S | CH$_2$CH$_3$ | |
| 261 | N | CF$_3$ | 0 | S | (CH$_2$)$_2$CH$_3$ | |
| 262 | N | CF$_3$ | 0 | S | CHFCF$_3$ | |
| 263 | N | CF$_3$ | 0 | S | CH$_2$CH$_2$OH | |
| 264 | N | CF$_3$ | 0 | S | CH$_2$COOC(CH$_3$)$_3$ | |
| 265 | CH | CH$_2$CH$_2$Cl | 0 | O | CH$_3$ | |
| 266 | CH | CH$_2$CH$_2$Cl | 0 | O | CH$_2$CH$_3$ | |
| 267 | CH | CH$_2$CH$_2$Cl | 0 | O | (CH$_2$)$_2$CH$_3$ | |
| 268 | CH | CH$_2$CH$_2$Cl | 0 | O | CH(CH$_3$)$_2$ | |
| 269 | CH | CH$_2$CH$_2$Cl | 0 | O | CH$_2$SC$_6$H$_5$ | |
| 270 | CH | CH$_2$CH$_2$Cl | 0 | O | CH$_2$CONHCH$_3$ | |
| 271 | CH | CH$_2$CH$_2$Cl | 0 | O | NH$_2$ | |
| 272 | CH | CH$_2$CH$_2$Cl | 0 | O | NHCH$_2$CH$_3$ | |
| 273 | N | CH$_2$CH$_2$Cl | 0 | O | CH$_2$CH$_3$ | |
| 274 | N | CH$_2$CH$_2$Cl | 0 | O | NH$_2$ | |
| 275 | N | CH$_2$Cl | 0 | O | CH$_3$ | |
| 276 | CH | CH$_2$Cl | 0 | O | CH$_3$ | |
| 277 | CH | CHF$_2$ | 0 | O | CH$_3$ | |
| 278 | CH | CHF$_2$ | 0 | O | CH$_2$CH$_3$ | |
| 279 | CH | CHF$_2$ | 0 | O | (CH$_2$)$_2$CH$_3$ | |
| 280 | CH | CHF$_2$ | 0 | O | CH$_2$CH=CH$_2$ | |
| 281 | CH | CHF$_2$ | 0 | O | C(CH$_3$)=CH$_2$ | |
| 282 | CH | CHF$_2$ | 0 | O | COOCH$_2$CH$_3$ | |
| 283 | CH | CHF$_2$ | 0 | O | CH$_2$CONHCH$_3$ | |
| 284 | CH | CHF$_2$ | 0 | O | CF$_2$CH$_3$ | |
| 285 | CH | CHF$_2$ | 0 | O | CHO | |
| 286 | CH | CHF$_2$ | 0 | O | NH$_2$ | |
| 287 | CH | CHF$_2$ | 0 | O | Cl | |
| 288 | CH | CHF$_2$ | 0 | O | NHCOCH$_3$ | |
| 289 | CH | CHF$_2$ | 0 | O | NHNH$_2$ | |
| 290 | N | CHF$_2$ | 0 | O | CH$_3$ | |
| 291 | N | CHF$_2$ | 0 | O | CH$_2$CH$_3$ | |
| 292 | N | CHF$_2$ | 0 | O | CH(CH$_3$)(CH$_2$)$_4$CH$_3$ | |
| 293 | N | CHF$_2$ | 0 | O | CH$_2$CH=CH$_2$ | |
| 294 | N | CHF$_2$ | 0 | O | COOCH$_2$CH$_3$ | |
| 295 | N | CHF$_2$ | 0 | O | NH$_2$ | |
| 296 | CH | CF$_3$ | 1 | O | CH$_3$ | |
| 297 | CH | CF$_3$ | 1 | O | COOCH$_2$CH$_3$ | |
| 298 | CH | CF$_3$ | 1 | O | CH$_2$COOC(CH$_3$)$_3$ | |
| 299 | CH | CF$_3$ | 1 | O | CHFCF$_3$ | |
| 300 | N | CF$_3$ | 0 | O | CH$_2$NHSO$_2$CH$_3$ | |
| 301 | N | CF$_3$ | 0 | O | (CH$_2$)$_2$NHSO$_2$CH$_3$ | |
| 302 | N | CF$_3$ | 0 | O | CH$_2$NHSO$_2$CH$_2$CH$_3$ | |
| 303 | N | CF$_3$ | 0 | O | CH$_2$NHSO$_2$CH$_2$C$_6$H$_5$ | |
| 304 | CH | CF$_3$ | 0 | O | (CH$_2$)$_4$NHSO$_2$CF$_3$ | |
| 305 | CH | CF$_3$ | 0 | O | (CH$_2$)$_2$S(CH$_2$)$_2$CH$_3$ | |
| 306 | CH | CF$_3$ | 0 | O | (CH$_2$)$_2$S(CH$_2$)$_4$OCH$_3$ | |
| 307 | CH | CF$_3$ | 0 | S | (CH$_2$)$_2$S(CH$_2$)$_2$CN | |
| 308 | CH | CF$_3$ | 0 | S | CH$_2$NHSO$_2$CH$_2$CH$_3$ | |
| 309 | CH | CF$_3$ | 0 | S | CH$_2$NHSO$_2$CH$_2$C$_6$H$_5$ | |
| 310 | CH | CF$_3$ | 0 | S | (CH$_2$)$_2$NHSO$_2$CH$_3$ | |
| 311 | CH | CF$_3$ | 0 | S | CH$_2$NHSO$_2$CH$_3$ | |
| 312 | CH | CF$_3$ | 0 | S | OH(CH$_3$)CH$_2$NHC$_6$H$_5$ | |
| 313 | CH | CF$_3$ | 0 | S | (CH$_2$)$_2$S(2-F)—C$_6$H$_4$ | |
| 314 | CH | CF$_3$ | 0 | S | (CH$_2$)$_6$NHCH$_2$OCH$_3$ | |
| 315 | CH | CF$_3$ | 0 | S | (CH$_2$)$_2$NH-(2-F)—C$_6$H$_4$ | |
| 316 | CH | CF$_3$ | 0 | S | (CH$_2$)$_3$NHCH$_2$CN | |
| 317 | CH | CF$_3$ | 0 | S | (CH$_2$)$_2$O(3-Cl)—C$_6$H$_4$ | |
| 318 | CH | CF$_3$ | 0 | S | (CH$_2$)$_6$NHCH$_2$CF$_3$ | |
| 319 | CH | CF$_3$ | 0 | S | (CH$_2$)$_2$O(3-CH$_3$)—C$_6$H$_4$ | |

TABLE 1-continued

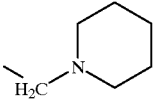

| No. | X | Y | m | W | R¹ | m.p. [° C.] |
|---|---|---|---|---|---|---|
| 320 | CH | $CF_3$ | 0 | O | $CH_2NHC_6H_5$ | |
| 321 | CH | $CF_3$ | 0 | O | $(CH_2)_4S(2\text{-}Br)\text{—}C_6H_4$ | |
| 322 | CH | $CF_3$ | 0 | O | $(CH_2)_6NH(CH_2)_2OCH_3$ | |
| 323 | CH | $CF_3$ | 0 | O | $(CH_2)_2NH(CH_2)_4OCH_3$ | |
| 324 | CH | $CF_3$ | 0 | O | $(CH_2)_3NH\text{-}(4\text{-}CN)\text{—}C_6H_4$ | |
| 325 | CH | $CF_3$ | 0 | O | $(CH_2)_2O(3\text{-}CH_3)\text{—}C_6H_4$ | |
| 326 | CH | $CF_3$ | 0 | O | $(CH_2)_4NHCH_2CF_3$ | |
| 327 | CH | $CF_3$ | 0 | O | $(CH_2)_4NHCH_2CN$ | |
| 328 | CH | $CF_3$ | 0 | O | $(CH_2)_3O(4\text{-}OCH_3)\text{—}C_6H_4$ | |
| 329 | CH | $CF_3$ | 0 | O | $CH_2SO_2\text{-}tert\text{-}C_4H_9$ | oil |
| 330 | CH | $CF_3$ | 0 | O | $CH_2SO_2\text{-}(4\text{-}F)\text{—}C_6H_4$ | oil |
| 331 | CH | $CF_3$ | 0 | O | $CH_2SO_2\text{—}C_6H_5$ | oil |
| 332 | CH | $CF_3$ | 0 | O | $CH_2SOCH_3$ | 63 |
| 333 | CH | $CF_3$ | 0 | O | $CH_2SO\text{—}C_6H_5$ | oil |
| 334 | CH | $CF_3$ | 0 | O | $CH_2CONH(CH_2)_2CH_3$ | 80–82 |
| 335 | CH | $CF_3$ | 0 | O | $(4\text{-}OCF_3)\text{—}C_6H_4$ | 57–59 |
| 336 | CH | $CF_3$ | 0 | O | $CH_2OCH_3$ | oil |
| 337 | CH | $CF_3$ | 0 | O | 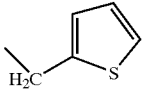 | 53–54 |
| 338 | CH | $CF_3$ | 0 | O | 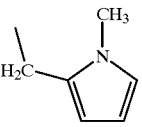 | oil |
| 339 | CH | $CF_3$ | 0 | O | $CH_2CH_2OCH_2CH_3$ | oil |
| 340 | CH | $CF_3$ | 0 | O | $CH_2CH_2NC_6H_5$ | 80–83 |
| 341 | CH | $CF_3$ | 0 | O | 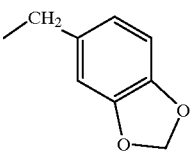 | 80–81 |
| 342 | CH | $CF_3$ | 0 | O | 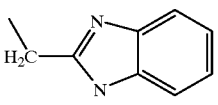 | 110–111 |
| 343 | CH | $CF_3$ | 0 | O | $CH_2CH_2O(CO)\text{-}(4\text{-}Cl)\text{—}C_6H_4$ | 80–82 |
| 344 | CH | $CF_3$ | 0 | O | $CH_2\text{-}(4\text{-}OCH_3)\text{—}C_6H_4$ | 54–55 |
| 345 | CH | $CF_3$ | 0 | O | $CH_2\text{-}(3\text{-}Cl)\text{—}C_6H_4$ | 51–52 |
| 346 | CH | $CF_3$ | 0 | O | $CH_2\text{-}cyclo\text{-}C_3H_5$ | oil |
| 347 | CH | $CF_3$ | 0 | O | $CH_2\text{-}(4\text{-}C_6H_5)\text{—}C_6H_4$ | oil |
| 348 | CH | $CF_3$ | 0 | O | benzimidazol-2-ylmethyl | 143–144 |
| 349 | CH | $CF_3$ | 0 | O | $CH_2CH_2O(CO)\text{-}(2,6\text{-}F2)\text{-}C_6H_3$ | 57–58 |
| 350 | CH | $CF_3$ | 0 | O | $CH_2CH_2O(CO)\text{-}(4\text{-}NO_2)\text{—}C_6H_4$ | 80–81 |
| 351 | CH | $CF_3$ | 0 | O | $CH_2\text{-}(2,6\text{-}Cl_2)\text{-}C_6H_3$ | 91–92 |
| 352 | CH | $CF_3$ | 0 | O | $CH_2CH_2OSO_2CH_3$ | oil |
| 353 | CH | $CF_3$ | 0 | O | $CH_2CH_2O(CO)\text{-}tert\text{-}C_4H_9$ | oil |

TABLE 1-continued

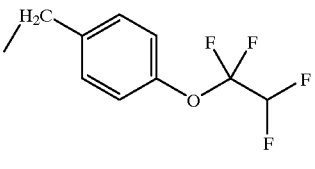

| No. | X | Y | m | W | R¹ | m.p. [° C.] |
|---|---|---|---|---|---|---|
| 354 | CH | CF$_3$ | 0 | O | CH$_2$-(3-F)—C$_6$H$_4$ | 50–51 |
| 355 | CH | CF$_3$ | 0 | O | CH$_2$CONCH$_2$C≡CH | 129–131 |
| 356 | CH | CF$_3$ | 0 | O | CH$_2$CH$_2$O(CO)-cyclo-C$_3$H$_7$ | oil |
| 357 | CH | CF$_3$ | 0 | O | CH$_2$CH$_2$O(CO)CH$_3$ | oil |
| 358 | CH | CF$_3$ | 0 | O | CH$_2$-[2,4-(CH$_3$)$_2$]—C$_6$H$_3$ | 85–86 |
| 359 | CH | CF$_3$ | 0 | O | CH$_2$CONCH$_2$CH=CH$_2$ | 210–212 |
| 360 | CH | CF$_3$ | 0 | O | CH$_2$CON(CH$_2$CH$_3$)$_2$ | oil |
| 361 | CH | CF$_3$ | 0 | O | CH$_2$CON(CH$_2$)$_3$CH$_3$ | 77–79 |
| 362 | CH | CF$_3$ | 0 | O | CH$_2$CONCH$_2$-(2-furyl) | 139–141 |
| 363 | CH | CF$_3$ | 0 | O | CH$_2$CONCH(CH$_3$)$_2$ | 112–114 |
| 364 | CH | CF$_3$ | 0 | O | CH$_2$CONCH(CH$_3$)[(CH$_2$)$_4$CH$_3$] | 73–75 |
| 365 | CH | CF$_3$ | 0 | O | CH$_2$CONCH$_2$CH$_2$C$_6$H$_5$ | 120–122 |
| 366 | CH | CF$_3$ | 0 | O | CH$_2$CONCH$_2$CH$_2$OCH$_2$CH$_3$ | 78 |
| 367 | CH | CF$_3$ | 0 | O | CH$_2$CONCH$_2$CF$_3$ | 176–178 |
| 368 | CH | CF$_3$ | 0 | O | CH$_2$CONCH(CH$_3$)[(CH$_2$)$_5$CH$_3$] | 85–86 |
| 369 | CH | CF$_3$ | 0 | O | 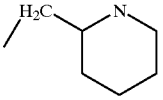 | oil |
| 370 | CH | CF$_3$ | 0 | O | 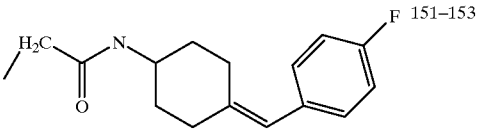 | oil |
| 371 | CH | CF$_3$ | 0 | O | CH$_2$CH2-(1-pyrryl) | oil |
| 372 | CH | CF$_3$ | 0 | O | CH$_2$CH$_2$C$_6$H$_5$ | oil |
| 373 | CH | CF$_3$ | 0 | O | CH$_2$Cl | 53–54 |
| 374 | CH | CF$_3$ | 0 | O | (CH$_2$)$_3$OH | 38–39 |
| 375 | CH | CF$_3$ | 0 | O | CH$_2$CONCH(CH$_3$)[(CH$_2$)$_2$]CH$_3$ | 68–69 |
| 376 | CH | CF$_3$ | 0 | O | CH$_2$CH(OCH$_3$)$_2$ | oil |
| 377 | CH | CF$_3$ | 0 | O | CH$_2$CONCH$_2$C(CH$_3$)$_3$ | oil |
| 378 | CH | CF$_3$ | 0 | O | CH$_2$CONC(CH$_3$)$_2$(CH$_2$CH$_3$) | oil |
| 379 | CH | CF$_3$ | 0 | O | CH$_2$CONCH$_2$CH$_2$-cyclo-C$_6$H$_{11}$ | 82–85 |
| 380 | CH | CF$_3$ | 0 | O | CH$_2$CONCH(CH$_3$)(1-naphthyl) | 142–146 |
| 381 | CH | CF$_3$ | 0 | O | (CH$_2$)$_3$Cl | oil |
| 382 | CH | CF$_3$ | 0 | O | CH$_2$CON-tert-C$_4$H$_9$ | oil |
| 383 | CH | CF$_3$ | 0 | O | CH$_2$CON(iso-C$_3$H$_7$)$_2$ | 70–72 |
| 384 | CH | CF$_3$ | 0 | O | CH$_2$CONCH(CH$_2$)$_7$CH$_3$ | 79–81 |
| 385 | CH | CF$_3$ | 0 | O | CH$_2$CON-cyclo-C$_6$H$_{11}$ | 119–121 |
| 386 | CH | CF$_3$ | 0 | O | CH$_2$CONCH$_2$CH$_2$-(4-Cl)—C$_6$H$_4$ | 120–121 |
| 387 | CH | CF$_3$ | 0 | O | CH$_2$CONCH$_2$-(2-thienyl) | 137–139 |
| 388 | CH | CF$_3$ | 0 | O |  | 151–153 |
| 389 | CH | CF$_3$ | 0 | O | CH$_2$CONHCH(CH$_3$)(CH$_2$CH$_3$) | 87–89 |
| 390 | CH | CF$_3$ | 0 | O | (CH$_2$)$_3$SCH$_3$ | oil |
| 391 | CH | CF$_3$ | 0 | O | (CH$_2$)$_3$SOCH$_3$ | oil |
| 392 | CH | CF$_3$ | 0 | O | CH$_2$CONC(CH$_3$)$_2$(C≡CH) | 111–113 |
| 393 | CH | CF$_3$ | 0 | O | CH$_2$CONCH(CH$_3$)CH$_2$CH$_2$CH(CH$_3$)$_2$ | 72–74 |

TABLE 1-continued

| No. | X | Y | m | W | R¹ | m.p. [° C.] |
|-----|---|---|---|---|----|----|
| 394 | CH | CF$_3$ | 0 | O | (propanoyl-NH-cyclohexyl-C(CH$_3$)$_2$CH$_2$CH$_3$) | oil |
| 395 | CH | CF$_3$ | 0 | O | CH$_2$CON-cyclo-C$_5$H$_9$ | 110–112 |
| 396 | CH | CF$_3$ | 0 | O | CH$_2$CON(CH$_2$)$_4$CH$_3$ | 75–77 |
| 397 | CH | CF$_3$ | 0 | O | (propanoyl-NH-benzothiazol-2-yl) | 190–192 |
| 398 | CH | CF$_3$ | 0 | O | CH$_2$CON(3-CF$_3$)C$_6$H$_4$ | 136–138 |
| 399 | CH | CF$_3$ | 0 | O | CH$_2$CON-cyclo-C$_8$H$_{17}$ | 115–117 |
| 400 | CH | CF$_3$ | 0 | O | (propanoyl-NH-pinanyl) | oil |
| 401 | CH | CF$_3$ | 0 | O | CH$_2$CON-Adamantyl | oil |
| 402 | CH | CF$_3$ | 0 | O | CH$_2$CON(CH$_2$CH$_2$CH$_3$)$_2$ | oil |
| 403 | CH | CF$_3$ | 0 | O | CH$_2$CONCH(CH$_3$)[(4-F)-C$_6$H$_4$] | 111–113 |
| 404 | CH | CF$_3$ | 0 | O | CH$_2$CONCH$_2$CH(CH$_3$)$_2$ | 91–93 |
| 405 | CH | CF$_3$ | 0 | O | (propanoyl-NH-CH(CH$_3$)-CH$_2$-indol-3-yl) | Oil |
| 406 | CH | CF$_3$ | 0 | O | CH$_2$CONCH$_2$CH$_2$OC$_6$H$_5$ | 99–101 |
| 407 | CH | CF$_3$ | 0 | O | CH$_2$CH=NOCH$_3$ | oil |
| 408 | CH | CF$_3$ | 0 | O | CH$_2$CONCH$_2$CH$_2$-[3,4-(OCH$_3$)$_2$]C$_6$H$_3$ | 123–125 |
| 409 | CH | CF$_3$ | 0 | O | CH$_2$CON-(2-Cl)C$_6$H$_4$ | 138–140 |
| 410 | CH | CF$_3$ | 0 | O | CH$_2$CON-(2-SCH$_3$)C$_6$H$_4$ | 136–138 |
| 411 | CH | CF$_3$ | 0 | O | (propanoyl-NH-6-methoxybenzothiazol-2-yl) | 222–225 |
| 412 | CH | CF$_3$ | 0 | O | (propanoyl-NH-5-methylisoxazol-3-yl) | 207–209 |
| 413 | CH | CF$_3$ | 0 | O | CH$_2$CON-(3-Br)C$_6$H$_4$ | 129–131 |
| 414 | CH | CF$_3$ | 0 | O | CH$_2$CON—N-(2,4,6-Cl$_3$)C$_6$H$_2$ | 153–155 |

TABLE 1-continued

| No. | X | Y | m | W | R¹ | m.p. [° C.] |
|---|---|---|---|---|---|---|
| 415 | CH | CF$_3$ | 0 | O | CH$_2$CON-(4-I)C$_6$H$_4$ | 143–145 |
| 416 | CH | CF$_3$ | 0 | O | CH$_2$CON—NCOCH$_2$(3-Thienyl) | 185–187 |
| 417 | CH | CF$_3$ | 0 | O | CH$_2$CH$_2$CHO | oil |
| 418 | CH | CF$_3$ | 0 | O | CH$_2$CON(CH$_3$)[(CH$_2$)$_3$CH$_3$] | oil |
| 419 | CH | CF$_3$ | 0 | O | CH$_2$CON-(3,5-Cl$_2$-2,4-F$_2$)C$_6$H | 166–167 |
| 420 | CH | CF$_3$ | 0 | O | CH$_2$CON—C$_6$H$_5$ | 215–217 |
| 421 | CH | CF$_3$ | 0 | O | CH$_2$CON(CH$_3$)(C$_6$H$_{11}$) | oil |
| 422 | CH | CF$_3$ | 0 | O | CH$_2$CON(CH$_2$CH$_3$)(CH$_2$CH=CH$_2$) | oil |
| 423 | CH | CF$_3$ | 0 | O | CH$_2$CON(CH$_2$CH$_3$)[CH(CH$_3$)$_2$] | oil |
| 424 | CH | CF$_3$ | 0 | O | CH$_2$CONCH(CH$_3$)[(CH$_3$)$_2$] | 108–110 |
| 425 | CH | CF$_3$ | 0 | O | CH$_2$CON(CH$_2$CH$_3$)[CH$_2$C(=CH$_2$)(CH$_3$)] | oil |
| 426 | CH | CF$_3$ | 0 | O | CH$_2$CONCH$_2$(4-tert-C$_4$H$_9$)C$_6$H$_4$ | oil |
| 427 | CH | CF$_3$ | 0 | O | CH$_2$CONCH(CH$_3$)(tert-C$_4$H$_9$) | oil |
| 428 | CH | CF$_3$ | 0 | O | CH$_2$CONCH(CH$_3$[CH$_2$CH(CH$_3$)(CH$_2$CH$_3$)] | oil |
| 429 | CH | CF$_3$ | 0 | O | CH$_2$CONCH$_2$COOCH$_2$CH$_3$ | 103–105 |
| 430 | CH | CF$_3$ | 0 | O | CH$_2$CON[(CH$_2$)$_2$CH$_3$](CH$_2$-cyclo-C$_3$H$_7$) | oil |
| 431 | CH | CF$_3$ | 0 | O | CH$_2$CONCH(CH$_3$)CH$_2$CH$_2$CH(CH$_3$)$_2$ | 80–82 |
| 432 | CH | CF$_3$ | 0 | O | CH$_2$CONCH(CH$_2$CH$_3$)[CH$_2$CH(CH$_3$)$_2$] | oil |
| 433 | CH | CF$_3$ | 0 | O | CH$_2$C=O-(1-Piperidinyl) | oil |
| 434 | CH | CF$_3$ | 0 | O | (2-chloroethyl-ethyl-oxazolinium chloride) | 180–182 |
| 435 | CH | CF$_3$ | 0 | O | CH$_2$CONCH$_2$C(=CH2)(CH$_3$) | 86–87 |
| 436 | CH | CF$_3$ | 0 | O | CH$_2$CONCH[CH(CH$_3$)$_2$](COOCH$_3$) | oil |
| 437 | CH | CF$_3$ | 0 | O | CH$_2$CONCH$_2$-cyclo-C$_3$H$_7$ | oil |
| 438 | CH | CF$_3$ | 0 | O | CH$_2$CON(CH$_2$)$_5$OH | oil |
| 439 | CH | CF$_3$ | 0 | O | CH$_2$CON(CH$_3$)(CH$_2$CO$_2$CH$_3$) | oil |
| 440 | CH | CF$_3$ | 0 | O | CH$_2$CON(CH$_3$)(CH$_2$CN) | oil |
| 441 | CH | CF$_3$ | 0 | O | CH$_2$CONCH[CH$_2$CH(CH$_3$)$_2$](CO$_2$CH$_3$) | oil |
| 442 | CH | CF$_3$ | 0 | O | CH$_2$CON-(1-Piperidinyl) | oil |
| 443 | CH | CF$_3$ | 0 | O | CH$_2$CONCH$_2$CH$_2$OCH$_3$ | 97–99 |
| 444 | CH | CF$_3$ | 0 | O | CH$_2$CH$_2$SC$_6$H$_5$ | oil |
| 445 | CH | CF$_3$ | 0 | O | CH$_2$CH$_2$SCH$_3$ | oil |
| 446 | CH | CF$_3$ | 0 | O | CH$_2$CH$_2$SCH$_2$C$_6$H$_5$ | oil |
| 447 | CH | CF$_3$ | 0 | O | (1-propyl-2-pyrrolidinone) | oil |
| 448 | CH | CF$_3$ | 0 | O | CH$_2$CON-(2-OH)C$_6$H$_4$ | 162–164 |
| 449 | CH | CF$_3$ | 0 | O | CH$_2$CON-(3-OH)C$_6$H$_4$ | oil |
| 450 | CH | CF$_3$ | 0 | O | CH$_2$CON-(2-CH$_3$)C$_6$H$_4$ | 163–164 |
| 451 | CH | CF$_3$ | 0 | O | CH$_2$CON-(3-NO$_2$)C$_6$H$_4$ | 176–178 |
| 452 | CH | CF$_3$ | 0 | O | CH$_2$CON-(3-OCF$_2$CHFCl)C$_6$H$_4$ | 120–121 |
| 453 | CH | CF$_3$ | 0 | O | CH$_2$CON-(3-CF$_3$-4-F)C$_6$H$_3$ | 168–170 |
| 454 | CH | CF$_3$ | 0 | O | CH$_2$CON-(2,4-Cl$_2$)C$_6$H$_3$ | 120–122 |
| 455 | CH | CF$_3$ | 0 | O | CH$_2$CON-(2-F-4.Cl)C$_6$H$_3$ | 148–151 |
| 456 | CH | CF$_3$ | 0 | O | CH$_2$CON-[2,4-(CH$_3$)$_2$]C$_6$H$_3$ | 123–125 |

TABLE 1-continued

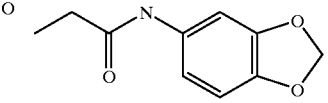

| No. | X | Y | m | W | R¹ | m.p. [° C.] |
|---|---|---|---|---|---|---|
| 457 | CH | CF₃ | 0 | O | CH₂CON-[2,3-(CH₃)₂]C₆H₃ | waxy |
| 458 | CH | CF₃ | 0 | O | 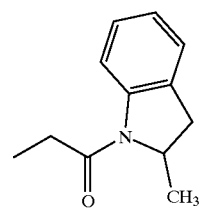 | waxy |
| 459 | CH | CF₃ | 0 | O | CH₂CON-(2-CH₃-3-Cl)C₆H₃ | 160–162 |
| 460 | CH | CF₃ | 0 | O | CH₂CON(CH₂CH₃)(C₆H₅) | oil |
| 461 | CH | CF₃ | 0 | O | 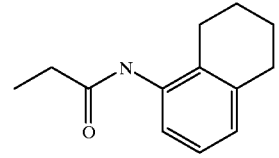 | 124–126 |
| 462 | CH | CF₃ | 0 | O | CH₂CON(2-OCH₃-5-Ph)C₆H₃ | 167–169 |
| 463 | CH | CF₃ | 0 | O | 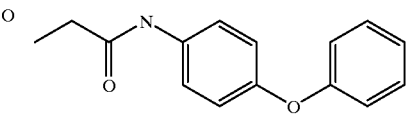 | 157–158 |
| 464 | CH | CF₃ | 0 | O | CH₂CON-(3-NO₂-4-Cl)C₆H₃ | oil |
| 465 | CH | CF₃ | 0 | O | CH₂CON-(2-Cl-4-CH₃)C₆H₃ | 106–108 |
| 466 | CH | CF₃ | 0 | O | CH₂CON-(3-OCH₂CH₃)C₆H₄ | waxy |
| 467 | CH | CF₃ | 0 | O |  | 169–171 |
| 468 | CH | CF₃ | 0 | O | CH₂CON-(4-CH₃)C₆H₄ | 139–141 |
| 469 | CH | CF₃ | 0 | O | CH₂CON-(1-Naphthyl) | 155–157 |
| 470 | CH | CF₃ | 0 | O | CH₂CON-(3-I)C₆H₄ | 135–137 |
| 471 | CH | CF₃ | 0 | O | CH₂CON-(2-OCH₂CH₃)C₆H₄ | 138 |
| 472 | CH | CF₃ | 0 | O | CH₂CON-(2-OCH₃)C₆H₄ | 130–132 |
| 473 | CH | CF₃ | 0 | O | CH₂CON-[3,5-(OCH₃)₂]C₆H₃ | 130–132 |
| 474 | CH | CF₃ | 0 | O | CH₂CON-(4-Cl)C₆H₄ | 139–141 |
| 475 | CH | CF₃ | 0 | O | CH₂CON-(3-CH₃)C₆H₄ | oil |
| 476 | CH | CF₃ | 0 | O | CH₂CON-(3-OCH₃)C₆H₄ | oil |
| 477 | CH | CF₃ | 0 | O | CH₂CON-(4-CH₂CH₃)C₆H₄ | 122–123 |
| 478 | CH | CF₃ | 0 | O | CH₂CON-(4-CF₃)C₆H₄ | 151–152 |
| 479 | CH | CF₃ | 0 | O | CH₂CON-(2-CH₃-4-Cl)C₆H₃ | 165–167 |
| 480 | CH | CF₃ | 0 | O | CH₂CH₂NCH₂C₆H₅ | oil |
| 481 | CH | CF₃ | 0 | O | CH₂CH₂NCH₂-(3-Pyridyl) | oil |
| 482 | CH | CF₃ | 0 | O | CH₂CH=NOCH₂CH₃ | oil |
| 483 | CH | CF₃ | 0 | O | CH₂CH=NOC₆H₅ | oil |
| 484 | CH | CF₃ | 0 | O | CH₂CON-(4-NO₂)C₆H₄ | 181–183 |
| 485 | CH | CF₃ | 0 | O | CH₂CON-(2-CH₃-4-NO2)C₆H₃ | 129–131 |
| 486 | CH | CF₃ | 0 | O | CH₂CON-(2-Cl-3-CF₃)C₆H₃ | 136 |
| 487 | CH | CF₃ | 0 | O | CH₂CON-(2-CN-4-Cl)C₆H₃ | 157–159 |
| 488 | CH | CF₃ | 0 | O | CH₂CON-(3,5-Cl₂)C₆H₃ | 167–169 |
| 489 | CH | CF₃ | 0 | O | CH₂CON-(3,5-Cl₂-4- | 132–134 |

TABLE 1-continued
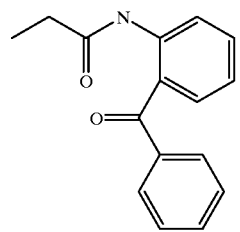
| No. | X | Y | m | W | R¹ | m.p. [° C.] |
|---|---|---|---|---|---|---|
| | | | | | $OCF_2CHF_2)C_6H_2$ | |
| 490 | CH | $CF_3$ | 0 | O | $CH_2CON$-(2,4,5-$Cl_3$)$C_6H_2$ | 146 |
| 491 | CH | $CF_3$ | 0 | O | $CH_2CON$-(3,5-$Cl_2$-4-$OCF_2CHFCF_3$)$C_6H_2$ | 124–126 |
| 492 | CH | $CF_3$ | 0 | O | $CH_2CON$-(2-$CF_3$-4-Cl)$C_6H_3$ | 136 |
| 493 | CH | $CF_3$ | 0 | O | 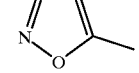 | oil |
| 494 | CH | $CF_3$ | 0 | O | 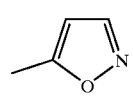 | 91–93 |
| 495 | CH | $CF_3$ | 0 | O | | 123–125 |
| 496 | CH | $CF_3$ | 0 | O | | 81–83 |
| 497 | CH | $CF_3$ | 0 | O | 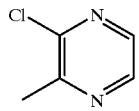 | 113–115 |
| 498 | CH | $CF_3$ | 0 | O | COOH | 155–157 |
| 499 | CH | $CF_3$ | 0 | O | 4-F-$C_6H_4$ | 104–106 |
| 500 | CH | $CF_3$ | 0 | O | $CON(C_2H_5)_2$ | oil |
| 501 | CH | $CF_3$ | 0 | O | $CONCH(CH_3)_2$ | oil |
| 502 | CH | $CF_3$ | 0 | O | $CON(CH_3)_2$ | 52–54 |
| 503 | CH | $CF_3$ | 0 | O | $CONHCH_2CCH$ | 105–107 |
| 504 | CH | $CF_3$ | 0 | O | CONH-cyclo-$C_3H_5$ | 101–103 |
| 505 | CH | $CF_3$ | 0 | O | $CONH_2$ | 206–208 |
| 506 | CH | $CF_3$ | 0 | O | 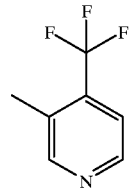 | 72–74 |

TABLE 1-continued

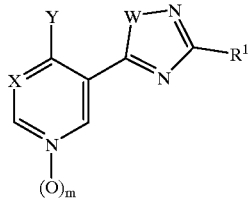

| No. | X | Y | m | W | R¹ | m.p. [° C.] |
|---|---|---|---|---|---|---|
| 507 | CH | CF$_3$ | 0 | O | 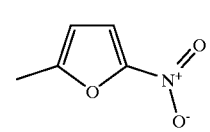 | 98–100 |
| 508 | CH | CF$_3$ | 0 | O | 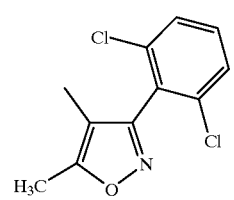 | 108–110 |
| 509 | CH | CF$_3$ | 0 | O | 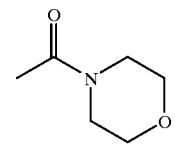 | 140–142 |
| 510 | CH | CF$_3$ | 0 | O | CONHCH$_3$ | 127–129 |
| 511 | CH | CF$_3$ | 0 | O | CONHCH$_2$CH=CH$_2$ | oil |
| 512 | CH | CF$_3$ | 0 | O | CON(CH$_2$CN)$_2$ | 90–92 |
| 513 | CH | CF$_3$ | 0 | O | 4-(t-C$_4$H$_9$)-C$_6$H$_4$ | 64–66 |
| 514 | CH | CF$_3$ | 0 | O | 4-CF$_3$-C$_6$H$_4$ | 89–91 |
| 515 | CH | CF$_3$ | 0 | O | 4-CH$_3$-3-F-C$_6$H$_3$ | 104–106 |
| 516 | CH | CF$_3$ | 0 | O | 2,4-di-Cl—C$_6$H$_3$ | 70–72 |
| 517 | CH | CF$_3$ | 0 | O | 4-(NHSO$_2$CH$_3$)—C$_6$H$_4$ | 204–206 |
| 518 | CH | CF$_3$ | 0 | O | 2,6-di-Cl-C$_6$H$_3$ | 139–141 |
| 519 | CH | CF$_3$ | 0 | O | COOCH$_2$C$_6$H$_5$ | 83–85 |
| 520 | CH | CF$_3$ | 0 | O | CONHC$_3$H$_7$ | oil |
| 521 | CH | CF$_3$ | 0 | O | 3,5-di-Br-4-(OCH$_3$)—C$_6$H$_2$ | 132–134 |
| 522 | CH | CF$_3$ | 0 | O | CHCl$_2$ | oil |
| 523 | CH | CF$_3$ | 0 | O | CCl$_3$ | oil |
| 524 | CH | CF$_3$ | 0 | O | CH(OCH3)$_2$ | oil |
| 525 | CH | CF$_3$ | 0 | O | 3-CF$_3$—C$_6$H$_4$ | 57–59 |
| 526 | CH | CF$_3$ | 0 | O | CON(CH$_2$)$_5$ | oil |
| 527 | CH | CF$_3$ | 0 | O | CON(CH$_3$)CH$_2$C$_6$H$_5$ | oil |
| 528 | CH | CF$_3$ | 0 | O | CONHCH$_2$C$_6$H$_5$ | 96–98 |
| 529 | CH | CF$_3$ | 0 | O | 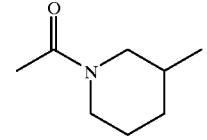 | oil |
| 530 | CH | CF$_3$ | 0 | O | CONH-n-C$_6$H$_{13}$ | oil |
| 531 | CH | CF$_3$ | 0 | O | CON(CH$_2$CH$_3$)CH$_2$C$_6$H$_5$ | oil |
| 532 | CH | CF$_3$ | 0 | O | CONH-c-C$_6$H$_{11}$ | 115–117 |
| 533 | CH | CF$_3$ | 0 | O | CON(n-C$_4$H$_9$)$_2$ | oil |
| 534 | CH | CF$_3$ | 0 | O |  | oil |

TABLE 1-continued

[Structure: pyridine/pyridine N-oxide ring with X, Y substituents, connected to triazole ring with W, R¹ substituents, and (O)ₘ on the N]

| No. | X | Y | m | W | R¹ | m.p. [° C.] |
|-----|-----|-----|---|---|----|----|
| 535 | CH | CF₃ | 0 | O | CONH-i-C₄H₉ | oil |
| 536 | CH | CF₃ | 0 | O | [N-acyl-2,6-dimethylmorpholine] | oil |
| 537 | CH | CF₃ | 0 | O | CON(CH₂)₄ | 68–70 |
| 538 | CH | CF₃ | 0 | O | CON(CH₃)-n-C₆H₁₃ | oil |
| 539 | CH | CF₃ | 0 | O | [N-acyl-4-ethoxycarbonylpiperazine] | oil |
| 540 | CH | CF₃ | 0 | O | CON(CH₃)CH₂CH₃ | oil |
| 541 | CH | CF₃ | 0 | O | CONHOCH₃ | oil |
| 542 | CH | CF₃ | 0 | O | [N-(4-tert-butylcyclohexyl)carboxamide] | oil |
| 543 | CH | CF₃ | 0 | O | CON(CH₃)CH₂CH₂CH₃ | oil |
| 544 | CH | CF₃ | 0 | O | CONHCH₂CH(OCH₃)₂ | oil |
| 545 | CH | CF₃ | 0 | O | CONH-t-C₄H₉ | 113–115 |
| 546 | CH | CF₃ | 0 | O | CONHCH₂-4-Cl-C₆H₄ | oil |
| 547 | CH | CF₃ | 0 | O | CONHCH(CH₃)C₆H₅ | oil |
| 548 | CH | CF₃ | 0 | O | CONHCH₂CH₂OCH₃ | 92–94 |
| 549 | CH | CF₃ | 0 | O | [N-(4H-1,2,4-triazol-4-yl)carboxamide] | 190–192 |
| 550 | CH | CF₃ | 0 | O | CONHC(CH₃)₂CCH | 90–92 |
| 551 | CH | CF₃ | 0 | O | CONHCH₂-2-Furyl | 93–95 |
| 552 | CH | CF₃ | 0 | O | CON(CH₂)₃ | 91–93 |
| 553 | CH | CF₃ | 0 | O | CONHCH₂-c-C₃H₅ | oil |
| 554 | CH | CF₃ | 0 | O | CONHC(CH₃)₂CH₂CH₃ | oil |
| 555 | CH | CF₃ | 0 | O | CONH(CH₂)₃C₆H₅ | oil |
| 556 | CH | CF₃ | 0 | O | CONHCH₂-3-Pyridyl | 132–134 |
| 557 | CH | CF₃ | 0 | O | CON(CH₃)-n-C₄H₉ | oil |
| 558 | CH | CF₃ | 0 | O | CON(CH₂CH3)-i-C₃H₇ | oil |

TABLE 1-continued

| No. | X | Y | m | W | R¹ | m.p. [° C.] |
|---|---|---|---|---|---|---|
| 559 | CH | CF₃ | 0 | O | (1-acetyl-4-methylpiperazinyl) | oil |
| 560 | CH | CF₃ | 0 | O | CONHCH₂CH₂Cl | oil |
| 561 | CH | CF₃ | 0 | O | CONHCH₂CN | 152–157 |
| 562 | CH | CF₃ | 0 | O | CON(CH₃)OCH₃ | oil |
| 563 | CH | CF₃ | 0 | O | CON(CH₃)CH₂CH=CH₂ | oil |
| 564 | CH | CF₃ | 0 | O | CONHCH₂COOCH₃ | oil |
| 565 | CH | CF₃ | 0 | O | CON(CH₃)-i-C₃H₇ | oil |
| 566 | CH | CF₃ | 0 | O | CON(CH₃)CH₂CH₂CN | oil |
| 567 | CH | CF₃ | 0 | O | CON(CH₃)CH₂CH(OCH₃)₂ | oil |
| 568 | CH | CF₃ | 0 | O | CON(CH₃)CH₂CH(—CH₂CH₂O—) | oil |
| 569 | CH | CF₃ | 0 | O | CONHCH₂C(=CH₂)CHH₃ | oil |
| 570 | CH | CF₃ | 0 | O | CON(CH₂CH₃)CH₂CH=CH₂ | oil |
| 571 | CH | CF₃ | 0 | O | CONHC₆H₅ | 83–85 |
| 572 | CH | CF₃ | 0 | O | CON(CH₃)CH₂CCH | oil |
| 573 | CH | CF₃ | 0 | O | CON(CH₃)CH₂CN | oil |
| 574 | CH | CF₃ | 0 | O | CON(CH₃)CH₂CH₂N(CH₃)₂ | oil |
| 575 | CH | CF₃ | 0 | O | CONHOCH₂CH₃ | 114–116 |
| 576 | CH | CF₃ | 0 | O | CONHCH₂CF₃ | 74–76 |
| 577 | CH | CF₃ | 0 | O | CON(CH₂CH₂Cl)₂ | oil |
| 578 | CH | CF₃ | 0 | O | CONH-c-C₄H₇ | oil |
| 579 | CH | CF₃ | 0 | O | CON(CH₂CH₂CH₃)CH₂-c-C₃H₅ | oil |
| 580 | CH | CF₃ | 0 | O | CON(CH₃)-c-C₆H₁₁ | oil |
| 581 | CH | CF₃ | 0 | O | CON(CH₂CH₃)CH₂C(=CH₂)CH₃ | oil |
| 582 | CH | CF₃ | 0 | O | CONHOCH₂CH=CH₂ | 90–92 |
| 583 | CH | CF₃ | 0 | O | CONHOCH₂C₆H₅ | 126–128 |
| 584 | CH | CF₃ | 0 | O | CON(CH₃)CH₂COOCH₃ | oil |
| 585 | CH | CF₃ | 0 | O | COONHCH₃ | 230–232 |
| 586 | CH | CF₃ | 0 | O | CONHCH₂CH₃ | 83–85 |
| 587 | CH | CF₃ | 0 | O | CONHCH(CH₃)COOCH₃ | 104–106 |
| 588 | CH | CF₃ | 0 | O | CONHCH(i-C₃H₇)COOCH₃ | oil |
| 589 | CH | CF₃ | 0 | O | CON(CH₃)CH₂CON(CH₃)₂ | oil |
| 590 | CH | CF₃ | 0 | O | CON(CH₃)-t-C₄H₉ | oil |
| 591 | CH | CF₃ | 0 | O | CONHO-t-C₄H₉ | 103–105 |
| 592 | CH | CF₃ | 0 | O | CON(CH₃)CH(i-C₃H₇)COOCH₃ | oil |
| 593 | CH | CF₃ | 0 | O | CH(OCH₂CH₃)₂ | oil |
| 594 | CH | CF₃ | 0 | O | (1-acetyl-4-methylpiperidinyl) | oil |
| 595 | CH | CF₃ | 0 | O | (1-acetyl-2-ethylpiperidinyl) | oil |

TABLE 1-continued
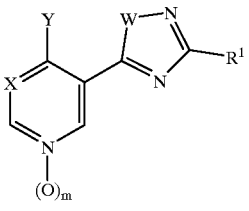
| No. | X | Y | m | W | R¹ | m.p. [° C.] |
|---|---|---|---|---|---|---|
| 596 | CH | CF$_3$ | 0 | O | 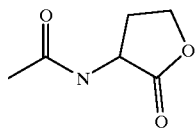 | oil |
| 597 | CH | CF$_3$ | 0 | O | 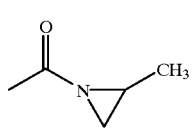 | oil |
| 598 | CH | CF$_3$ | 0 | O | 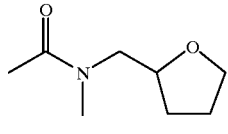 | oil |
| 599 | CH | CF$_3$ | 0 | O | CONHCH$_2$CONHCH$_3$ | 101–103 |
| 600 | CH | CF$_3$ | 0 | O | CON(CH$_2$)$_7$ | oil |
| 601 | CH | CF$_3$ | 0 | O | CON(CH$_2$)$_6$ | oil |
| 602 | CH | CF$_3$ | 0 | O | CON(CH$_2$CH$_3$)CH$_2$CH$_2$OCH$_3$ | oil |
| 603 | CH | CF$_3$ | 0 | O | 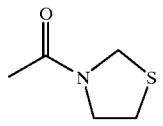 | oil |
| 604 | CH | CF$_3$ | 0 | O | 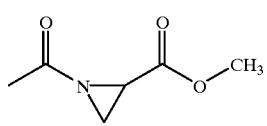 | oil |
| 605 | CH | CF$_3$ | 0 | O | 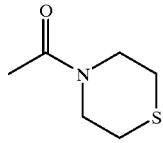 | oil |
| 606 | CH | CF$_3$ | 0 | O | CON(CH$_2$CH$_3$)CH$_2$CH$_2$CN | oil |
| 607 | CH | CF$_3$ | 0 | O |  | oil |
| 608 | CH | CF$_3$ | 0 | O | CON(CH$_2$CH$_3$)-n-C$_4$H$_9$ | oil |

TABLE 1-continued

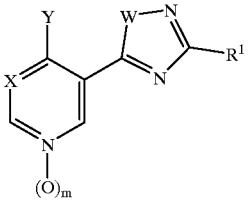

| No. | X | Y | m | W | R¹ | m.p. [° C.] |
|---|---|---|---|---|---|---|
| 609 | CH | CF₃ | 0 | O | 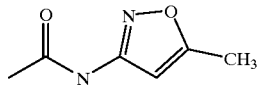 | 179–181 |
| 610 | CH | CF₃ | 0 | O | CONHCH(CH₃)CONHCH₃ | 136–138 |
| 611 | CH | CF₃ | 0 | O | COON(CH₂)₄ | 64–66 |
| 612 | CH | CF₃ | 0 | O | CONHCH₂CON(CH₃)₂ | 107–109 |
| 613 | CH | CF₃ | 0 | O | CON(CH₂COOCH₂CH₃)₂ | oil |
| 614 | CH | CF₃ | 0 | O | 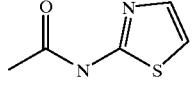 | 180–182 |
| 615 | CH | CF₃ | 0 | O | 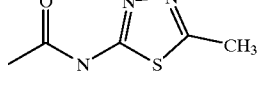 | 221–223 |
| 616 | CH | CF₃ | 0 | O | 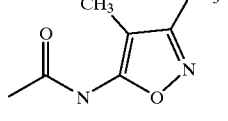 | 234–236 |
| 617 | CH | CF₃ | 0 | O | 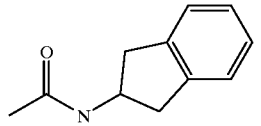 | oil |
| 618 | CH | CF₃ | 0 | O | CON(CH₃)CH₂-6-Cl-3-pyridyl | oil |
| 619 | CH | CF₃ | 0 | O | 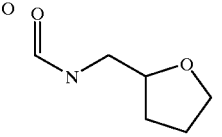 | 105–107 |
| 620 | CH | CF₃ | 0 | O | CONHCH(CH₃)CH(OCH₃)₂ | oil |
| 621 | CH | CF₃ | 0 | O | CONHCH₂CH₂SCH₃ | oil |
| 622 | CH | CF₃ | 0 | O | CONHCH(CH₃)CH₂OCH₃ | 70–72 |
| 623 | CH | CF₃ | 0 | O | CONHCH₂CH₂NHCOCH₃ | 124–126 |
| 624 | CH | CF₃ | 0 | O | CONH(CH₂)₃OCH₂CH₃ | oil |
| 625 | CH | CF₃ | 0 | O | CON(CH₂CH₃)CH₂CH₂CH₃ | oil |
| 626 | CH | CF₃ | 0 | O | CON(CH₂CH₃)CH₂OCH₃ | oil |
| 627 | CH | CF₃ | 0 | O | CONHCH₂CH₂SCH₂CH₃ | oil |
| 628 | CH | CF₃ | 0 | O | CONHCH₂CH₂OCH₂CH₃ | 59–61 |
| 629 | CH | CF₃ | 0 | O |  | Oil |

TABLE 1-continued

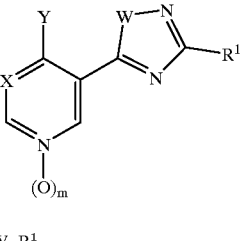

| No. | X | Y | m | W | R¹ | m.p. [° C.] |
|---|---|---|---|---|---|---|
| 630 | CH | CF$_3$ | 0 | O | 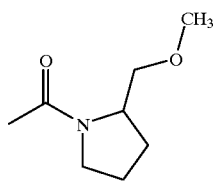 | 174–176 |
| 631 | CH | CF$_3$ | 0 | O | CONHCH(CH$_3$)CH(OCH$_3$)$_2$ | oil |
| 632 | CH | CF$_3$ | 0 | O | CONHCH$_2$CH$_2$SCH$_3$ | oil |
| 633 | CH | CF$_3$ | 0 | O | CONHCH(CH$_3$)CH$_2$OCH$_3$ | 70–72 |
| 634 | CH | CF$_3$ | 0 | O | CONHCH$_2$CH$_2$NHCOCH$_3$ | 124–126 |
| 635 | CH | CF$_3$ | 0 | O | CONH(CH$_2$)$_3$OCH$_2$CH$_3$ | oil |
| 636 | CH | CF$_3$ | 0 | O | CON(CH$_2$CH$_3$)CH2CH$_2$CH$_3$ | oil |
| 637 | CH | CF$_3$ | 0 | O | CON(CH$_2$CH$_3$)CH$_2$OCH$_3$ | oil |
| 638 | CH | CF$_3$ | 0 | O | CONHCH$_2$CH$_2$SCH$_2$CH$_3$ | oil |
| 639 | CH | CF$_3$ | 0 | O | CONHCH(CH$_3$)CH$_2$COOCH$_2$CH$_3$ | oil |
| 640 | CH | CF$_3$ | 0 | O | CONH-4-COOCH$_3$—C$_6$H$_4$ | 189–191 |
| 641 | CH | CF$_3$ | 0 | O | CONH-4-CONH$_2$—C$_6$H$_4$ | 265–267 |
| 642 | CH | CF$_3$ | 0 | O | CONHCH$_2$CH$_2$Br | oil |
| 643 | CH | CF$_3$ | 0 | O | CONHCH$_2$CH=CHCH$_2$Cl | oil |
| 644 | CH | CF$_3$ | 0 | O | CONH-4-CONHCH$_3$—C$_6$H$_4$ | 219–221 |
| 645 | CH | CF$_3$ | 0 | O | CONHCH$_2$CH$_2$Br | oil |
| 646 | CH | CF$_3$ | 0 | O | CONHCH$_2$CH$_2$OCH$_3$ | oil |
| 647 | CH | CF$_3$ | 0 | O | CONH-4-CH$_2$CH$_3$—C$_6$H$_4$ | 97–99 |
| 648 | CH | CF$_3$ | 0 | O | CONHCH$_2$CH$_2$OCH(CH$_3$)$_2$ | oil |
| 649 | CH | CF$_3$ | 0 | O | CONHCH$_2$CH$_2$CH$_2$OCH$_2$CH$_3$ | oil |
| 650 | CH | CF$_3$ | 0 | O | 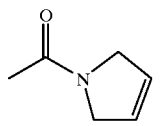 | oil |
| 651 | CH | CF$_3$ | 0 | O | 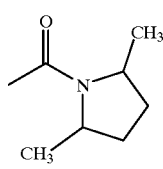 | 64–66 |
| 652 | CH | CF$_3$ | 0 | O | 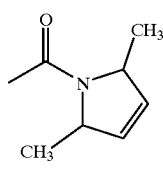 | oil |
| 653 | CH | CF$_3$ | 0 | O |  | oil |
| 654 | CH | CF$_3$ | 0 | O | CH$_2$CON(CH$_3$)CH$_2$CH$_3$ | oil |
| 655 | CH | CF$_3$ | 0 | O | CH$_2$CON(CH$_3$)$_2$ | 58–60 |
| 656 | CH | CF$_3$ | 0 | O | CH$_2$CON(CH$_2$)$_4$ | 101–103 |

TABLE 1-continued

[Structure: pyrimidine ring with Y, X, and (O)$_m$ on N; connected to 1,2,4-triazole ring with W and R$^1$]

| No. | X | Y | m | W | R$^1$ | m.p. [° C.] |
|---|---|---|---|---|---|---|
| 657 | CH | CF$_3$ | 0 | O | [1-propanoyl-thiomorpholine] | oil |
| 658 | CH | CF$_3$ | 0 | O | [1-propanoyl-thiazolidine] | 90–92 |
| 659 | CH | CF$_3$ | 0 | O | CH$_2$CONHCH$_2$CH$_3$ | 104–106 |
| 660 | CH | CF$_3$ | 0 | O | CH$_2$CON(CH$_3$)CH$_2$CH$_2$CH | oil |
| 661 | CH | CF$_3$ | 0 | O | CH$_2$CON(CH$_3$)CH$_2$CH$_2$CH$_3$ | oil |
| 662 | CH | CF$_3$ | 0 | O | CH$_2$CON(CH$_3$)CH$_2$CH (—OCH$_2$CH$_2$O—) | oil |
| 663 | CH | CF$_3$ | 0 | O | CH$_2$CONHCH$_2$CH$_3$ | 104–106 |
| 664 | CH | CF$_3$ | 0 | O | CH$_2$CON(CH$_3$)CH$_2$CH$_2$CH | oil |
| 665 | CH | CF$_3$ | 0 | O | CH$_2$CON(CH$_3$)CH$_2$CH$_2$CH$_3$ | oil |
| 667 | CH | CF$_3$ | 0 | O | CH$_2$CON(CH$_3$)CH$_2$CH (—OCH$_2$CH$_2$O—) | oil |
| 668 | CH | CF$_3$ | 0 | O | [1-propanoyl-2,5-dihydropyrrole] | 79–81 |
| 669 | CH | CF$_3$ | 0 | O | CH$_2$CONHCH$_2$CH$_2$SCH$_3$ | 65–67 |
| 670 | CH | CF$_3$ | 0 | O | CH$_2$CONHCH(CH$_3$)CH$_2$OCH$_3$ | 86–88 |
| 671 | CH | CF$_3$ | 0 | O | CON(CH$_3$)CH$_2$CH$_2$OCO-c-C$_4$H$_7$ | oil |
| 672 | CH | CF$_3$ | 0 | O | CH$_2$CONHCH$_2$CH$_2$Br | 87–89 |
| 673 | CH | CF$_3$ | 0 | O | CON(CH$_3$)CH$_2$CH$_2$OCOC$_6$H$_5$ | oil |
| 674 | CH | CF$_3$ | 0 | O | CON(CH$_3$)CH$_2$CH$_2$OCO-c-C$_3$H$_5$ | oil |
| 675 | CH | CF$_3$ | 0 | O | CONH-2-CH$_3$—C$_6$H$_4$ | 104–106 |
| 676 | CH | CF$_3$ | 0 | O | CH$_2$CON(i-C$_3$H$_7$)-4-F—C$_6$H$_4$ | 102–104 |
| 677 | CH | CF$_3$ | 0 | O | [1-acetyl-pyrrolidine-2-carbonyl-diazo] | oil |
| 678 | CH | CF$_3$ | 0 | O | [1-acetyl-pyrrolidine-2-carboxylic acid methyl ester] | oil |
| 679 | CH | CF$_3$ | 0 | O | CON(CH$_3$)CH$_2$CH$_2$OCONHC$_6$H$_5$ | 100–102 |
| 680 | CH | CF$_3$ | 0 | O | CON(CH$_3$)CH$_2$CH$_2$OCONHCH$_2$CH$_3$ | oil |
| 681 | CH | CF$_3$ | 0 | O | CON(CH$_3$)CH$_2$CH$_2$OSO$_2$CH$_3$ | oil |

TABLE 1-continued

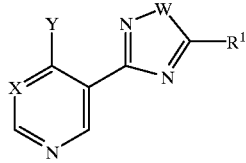

| No. | X | Y | m | W | R¹ | m.p. [° C.] |
|---|---|---|---|---|---|---|
| 682 | CH | CF$_3$ | 0 | O | CH$_2$CONH-c-C$_4$H$_7$ | 133–135 |
| 683 | CH | CF$_3$ | 0 | O | CH$_2$CONHCH$_2$CN | 158–160 |

TABLE 2

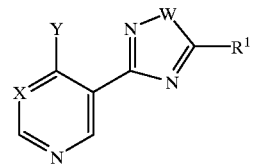

| No. | X | Y | W | R¹ | m.p. [° C.] |
|---|---|---|---|---|---|
| 684 | N | (CF$_2$)$_3$CHF$_2$ | O | CH$_3$ | |
| 685 | N | (CF$_2$)$_2$CF$_3$ | O | CH$_2$CH$_3$ | |
| 686 | N | (CF$_2$)$_2$CF$_3$ | O | COOCH$_2$CH$_3$ | |
| 687 | N | (CF$_2$)$_2$CF$_3$ | O | OH | |
| 688 | N | (CF$_2$)$_2$CF$_3$ | O | OCH$_3$ | |
| 689 | N | CF$_2$CF$_3$ | O | CH$_3$ | |
| 690 | N | CF$_2$CF$_3$ | O | CH$_2$CH$_3$ | |
| 691 | N | CF$_2$CF$_3$ | S | CH$_3$ | |
| 692 | N | CF2CF$_3$ | S | CH$_2$CH$_3$ | |
| 693 | N | CF$_2$CF$_3$ | S | (CH$_2$)$_2$CH$_3$ | |
| 694 | CH | CF$_3$ | O | CH$_3$ | oil |
| 695 | CH | CF$_3$ | O | CH$_2$CH$_3$ | |
| 696 | CH | CF$_3$ | O | (CH$_2$)$_2$CH$_3$ | |
| 697 | CH | CF$_3$ | O | CH(CH$_3$)$_2$ | |
| 698 | CH | CF$_3$ | O | (CH$_2$)$_3$CH$_3$ | |
| 699 | CH | CF$_3$ | O | CH(CH$_3$)CH$_2$CH$_3$ | |
| 700 | CH | CF$_3$ | O | CH$_2$CH(CH$_3$)$_2$ | |
| 701 | CH | CF$_3$ | O | C(CH$_3$)$_3$ | oil |
| 702 | CH | CF$_3$ | O | (CH$_2$)$_4$CH$_3$ | |
| 703 | CH | CF$_3$ | O | CH(CH$_3$)(CH$_2$)$_2$CH$_3$ | |
| 704 | CH | CF$_3$ | O | (CH$_2$)$_2$CH(CH$_3$)$_2$ | |
| 705 | CH | CF$_3$ | O | CH$_2$C(CH$_3$)$_3$ | |
| 706 | CH | CF$_3$ | O | Cyclo-C$_5$H$_9$ | |
| 707 | CH | CF$_3$ | O | Cyclo-C$_6$H$_{11}$ | |
| 708 | CH | CF$_3$ | O | CHO | |
| 709 | CH | CF$_3$ | O | CH=CH$_2$ | |
| 710 | CH | CF$_3$ | O | CH$_2$CH=C(CH$_3$)$_2$ | |
| 711 | CH | CF$_3$ | O | CH$_2$CH=CH$_2$ | |
| 712 | CH | CF$_3$ | O | C(CH$_3$)=CH$_2$ | |
| 713 | CH | CF$_3$ | O | (CH$_2$)$_5$C=CH$_2$ | |
| 714 | CH | CF$_3$ | O | C(=CHCH$_3$)CH$_3$ | |
| 715 | CH | CF$_3$ | O | CH$_2$C≡CH | |
| 716 | CH | CF$_3$ | O | CH$_2$CH$_2$C≡CH | |
| 717 | CH | CF$_3$ | O | CH$_2$C≡CCH$_2$CH$_3$ | |
| 718 | CH | CF$_3$ | O | (CH$_2$)$_4$C≡CH | |
| 719 | CH | CF$_3$ | O | CHFCF$_3$ | |
| 720 | CH | CF$_3$ | O | COOCH$_2$CH$_3$ | |
| 721 | CH | CF$_3$ | O | CH$_2$CH$_2$OH | |
| 722 | CH | CF$_3$ | O | CH$_2$CH$_2$OCH$_3$ | |
| 723 | CH | CF$_3$ | O | CH$_2$COOC(CH$_3$)$_3$ | |
| 724 | CH | CF$_3$ | O | CH$_2$SC$_6$H$_5$ | |
| 725 | CH | CF$_3$ | O | CH$_2$CONHCH$_3$ | |
| 726 | CH | CF$_3$ | O | CH$_2$CH(OH)CH$_2$CH | |
| 727 | CH | CF$_3$ | O | CH$_2$COCH$_3$ | |
| 728 | CH | CF$_3$ | O | COCH3 | |
| 729 | CH | CF$_3$ | O | CH$_2$OC$_6$H$_5$ | |
| 730 | CH | CF$_3$ | O | COC$_6$H$_5$ | |
| 731 | CH | CF$_3$ | O | CF$_2$CH$_3$ | |
| 732 | CH | CF$_3$ | O | CH$_2$CN | |
| 733 | CH | CF$_3$ | O | CH$_2$CH(—O—)CH$_2$ | |
| 734 | CH | CF$_3$ | O | CH$_2$(4-OCH$_3$)C$_6$H$_5$ | |
| 735 | CH | CF$_3$ | O | CH$_2$CH(OH)CH$_2$SC$_6$H$_5$ | |
| 736 | CH | CF$_3$ | O | CH=CF$_2$ | |
| 737 | CH | CF$_3$ | O | CCl=CHCl | |
| 738 | CH | CF$_3$ | O | 2-Pyridyl | |
| 739 | CH | CF$_3$ | O | OC$_6$H$_5$ | |
| 740 | CH | CF$_3$ | O | OH | |
| 741 | CH | CF$_3$ | O | OCH$_3$ | |
| 742 | CH | CF$_3$ | O | OCH$_2$CH$_3$ | |
| 743 | CH | CF$_3$ | O | OCHF$_2$ | |
| 744 | CH | CF$_3$ | O | OCH$_2$C$_6$H$_5$ | |
| 745 | CH | CF$_3$ | O | SCH$_3$ | |
| 746 | CH | CF$_3$ | O | SC$_6$H$_5$ | |
| 747 | CH | CF$_3$ | O | NH$_2$ | |
| 748 | CH | CF$_3$ | O | NHCH$_3$ | |
| 749 | CH | CF$_3$ | O | NHCH$_2$CH$_3$ | |
| 750 | CH | CF$_3$ | O | N(CH$_2$CH$_3$)$_2$ | |
| 751 | CH | CF$_3$ | O | N(CH$_2$CN)$_2$ | |
| 752 | CH | CF$_3$ | O | N(CH$_3$)$_2$ | |
| 753 | CH | CF$_3$ | O | NHCOCH$_3$ | |
| 754 | CH | CF$_3$ | O | NHCOCH$_2$CH$_3$ | |
| 755 | CH | CF$_3$ | O | OSO$_2$CH$_3$ | |
| 756 | CH | CF$_3$ | O | SOCH$_2$(4-Br)—C$_6$H$_4$ | |
| 757 | CH | CF$_3$ | O | N(CH$_3$)COOCH$_2$C$_6$H$_5$ | |
| 758 | N | CF$_3$ | O | CH$_3$ | |
| 759 | N | CF$_3$ | O | CH$_2$CH$_3$ | |
| 760 | N | CF$_3$ | O | (CH$_2$)$_2$CH$_3$ | |
| 761 | N | CF$_3$ | O | CH(CH$_3$)$_2$ | |
| 762 | N | CF$_3$ | O | (CH$_2$)$_3$CH$_3$ | |
| 763 | N | CF$_3$ | O | CH$_2$CH(CH$_3$)$_2$ | |
| 764 | N | CF$_3$ | O | C(CH$_3$)$_3$ | |
| 765 | N | CF$_3$ | O | CH$_2$C(CH$_3$)$_3$ | |
| 766 | N | CF$_3$ | O | Cyclo-C$_5$H$_9$ | |
| 767 | N | CF$_3$ | O | Cyclo-C$_6$H$_{11}$ | |
| 768 | N | CF$_3$ | O | CH$_2$C=C(CH$_3$)$_2$ | |
| 769 | N | CF$_3$ | O | CH$_2$CH$_2$C=CH$_2$ | |
| 770 | N | CF$_3$ | O | CH$_2$CH=CH$_2$ | |
| 771 | N | CF$_3$ | O | (CH$_2$)$_5$CH=CH$_2$ | |
| 772 | N | CF$_3$ | O | CH$_2$C≡CH | |
| 773 | N | CF$_3$ | O | CH$_2$C≡CCH$_2$CH$_3$ | |
| 774 | N | CF$_3$ | O | CHFCF$_3$ | |
| 775 | N | CF$_3$ | O | COOCH$_2$CH$_3$ | |

TABLE 2-continued

| No. | X | Y | W | R$^1$ | m.p. [° C.] |
|---|---|---|---|---|---|
| 776 | N | CF$_3$ | O | CH$_2$CH$_2$OH | |
| 777 | N | CF$_3$ | O | CH$_2$CH$_2$OCH$_3$ | |
| 778 | N | CF$_3$ | O | CH$_2$COOC(CH$_3$)$_3$ | |
| 779 | N | CF$_3$ | O | CH$_2$SC$_6$H$_5$ | |
| 780 | N | CF$_3$ | O | CH$_2$CONHCH$_3$ | |
| 781 | N | CF$_3$ | O | CH$_2$CH(OH)CH$_2$OH | |
| 782 | N | CF$_3$ | O | CHO | |
| 783 | N | CF$_3$ | O | COCH$_3$ | |
| 784 | N | CF$_3$ | O | CH$_2$OC$_6$H$_5$ | |
| 785 | N | CF$_3$ | O | COC$_6$H$_5$ | |
| 786 | N | CF$_3$ | O | CF$_2$CH$_3$ | |
| 787 | N | CF$_3$ | O | CH$_2$CN | |
| 788 | N | CF$_3$ | O | CH$_2$CH$_2$CN | |
| 789 | N | CF$_3$ | O | CH=CF$_2$ | |
| 790 | N | CF$_3$ | O | 2-Furyl | |
| 791 | N | CF$_3$ | O | OH | |
| 792 | N | CF$_3$ | O | OCH$_3$ | |
| 793 | N | CF$_3$ | O | OCH$_2$CH$_3$ | |
| 794 | N | CF$_3$ | O | OCHF$_2$ | |
| 795 | N | CF$_3$ | O | OCH$_2$C$_6$H$_5$ | |
| 796 | N | CF$_3$ | O | NH$_2$ | |
| 797 | N | CF$_3$ | O | NHCH$_3$ | |
| 798 | N | CF$_3$ | O | NHCH$_2$CH$_3$ | |
| 799 | N | CF$_3$ | O | N(CH$_2$CH$_3$)$_2$ | |
| 800 | N | CF$_3$ | O | N(CH$_2$CN)$_2$ | |
| 801 | N | CF$_3$ | O | N(CH$_3$)$_2$ | |
| 802 | N | CF$_3$ | O | NHCOCH$_3$ | |
| 803 | N | CF$_3$ | O | NHCOCH$_2$CH$_3$ | |
| 804 | N | CF$_3$ | O | OSO$_2$CH$_3$ | |
| 805 | CH | CF$_3$ | S | CH$_3$ | |
| 806 | CH | CF$_3$ | S | CH$_2$CH$_3$ | |
| 807 | CH | CF$_3$ | S | (CH$_2$)$_2$CH$_3$ | |
| 808 | CH | CF$_3$ | S | CHO | |
| 809 | CH | CF$_3$ | S | CHFCF$_3$ | |
| 810 | CH | CF$_3$ | S | CH$_2$C≡CH | |
| 811 | CH | CF$_3$ | S | COOCH$_2$CH$_3$ | |
| 812 | CH | CF$_3$ | S | CH$_2$COOC(CH$_3$)$_3$ | |
| 813 | CH | CF$_3$ | S | CH$_2$CN | |
| 814 | N | CF$_3$ | S | CH$_3$ | |
| 815 | N | CF$_3$ | S | CH$_2$CH$_3$ | |
| 816 | N | CF$_3$ | S | (CH$_2$)$_2$CH$_3$ | |
| 817 | N | CF$_3$ | S | CHFCF$_3$ | |
| 818 | N | CF$_3$ | S | CH$_2$CH$_2$OH | |
| 819 | N | CF$_3$ | S | CH$_2$COOC(CH$_3$)$_3$ | |
| 820 | N | CH$_2$CH$_2$Cl | O | CH$_2$CH$_3$ | |
| 821 | N | CH$_2$CH$_2$Cl | O | NH$_2$ | |
| 822 | N | CH$_2$Cl | O | CH$_3$ | |
| 823 | CH | CHF$_2$ | O | CH$_3$ | |
| 824 | CH | CHF$_2$ | O | CH$_2$CH$_3$ | |
| 825 | CH | CHF$_2$ | O | (CH$_2$)$_2$CH$_3$ | |
| 826 | CH | CHF$_2$ | O | CH$_2$C=CH$_2$ | |
| 827 | CH | CHF$_2$ | O | C(CH$_3$)=CH$_2$ | |
| 828 | CH | CHF$_2$ | O | COOCH$_2$CH$_3$ | |
| 829 | CH | CHF$_2$ | O | CH$_2$CONHCH$_3$ | |
| 830 | CH | CHF$_2$ | O | CF$_2$CH$_3$ | |
| 831 | CH | CHF$_2$ | O | CHO | |
| 832 | CH | CHF$_2$ | O | NH$_2$ | |
| 833 | CH | CHF$_2$ | O | NHCOCH$_3$ | |
| 834 | N | CHF$_2$ | O | CH$_3$ | |
| 835 | N | CHF$_2$ | O | CH$_2$CH$_3$ | |
| 836 | N | CHF$_2$ | O | CH(CH$_3$)(CH$_2$)$_4$CH$_3$ | |
| 837 | N | CHF$_2$ | O | CH$_2$CH=CH$_2$ | |
| 838 | N | CHF$_2$ | O | COOCH$_2$CH$_3$ | |
| 839 | N | CHF$_2$ | O | NH$_2$ | |

TABLE 3

| No. | X | Y | m | V | R$^1$ | m.p. [° C.] |
|---|---|---|---|---|---|---|
| 840 | N | (CF$_2$)$_3$CHF$_2$ | 0 | O | CH$_3$ | |
| 841 | N | (CF$_2$)$_2$CF$_3$ | 0 | O | CH$_2$CH$_3$ | |
| 842 | N | (CF$_2$)$_2$CF$_3$ | 0 | O | COOCH$_2$CH$_3$ | |
| 843 | N | (CF$_2$)$_2$CF$_3$ | 0 | O | SH | |
| 844 | N | (CF$_2$)$_2$CF$_3$ | 0 | O | SCH$_3$ | |
| 845 | N | (CF$_2$)$_2$CF$_3$ | 0 | O | SCH$_2$C≡CH | |
| 846 | N | CF$_2$CF$_3$ | 0 | O | CH$_3$ | |
| 847 | N | CF$_2$CF$_3$ | 0 | O | CH$_2$CH$_3$ | |
| 848 | N | CF$_3$ | 0 | O | CH$_3$ | |
| 849 | N | CF$_3$ | 0 | O | CH$_2$CH$_3$ | |
| 850 | N | CF$_3$ | 0 | O | (CH$_2$)$_2$CH$_3$ | |
| 851 | N | CF$_3$ | 0 | O | CH(CH$_3$)$_2$ | |
| 852 | N | CF$_3$ | 0 | O | (CH$_2$)$_3$CH$_3$ | |
| 853 | N | CF$_3$ | 0 | O | CH$_2$CH(CH$_3$)$_2$ | |
| 854 | N | CF$_3$ | 0 | O | C(CH$_3$)$_3$ | |

TABLE 3-continued

| No. | X | Y | m | V | R¹ | m.p. [° C.] |
|---|---|---|---|---|---|---|
| 855 | N | $CF_3$ | 0 | O | $CH_2C(CH_3)_3$ | |
| 856 | N | $CF_3$ | 0 | O | Cyclo-$C_5H_9$ | |
| 857 | N | $CF_3$ | 0 | O | Cyclo-$C_6H_{11}$ | |
| 858 | N | $CF_3$ | 0 | O | $CH_2CH{=}C(CH_3)_2$ | |
| 859 | N | $CF_3$ | 0 | O | $CH_2CH_2CH{=}CH_2$ | |
| 860 | N | $CF_3$ | 0 | O | $CH_2CH{=}CH_2$ | |
| 861 | N | $CF_3$ | 0 | O | $(CH_2)_5CH{=}CH_2$ | |
| 862 | N | $CF_3$ | 0 | O | $CH_2C{\equiv}CH$ | |
| 863 | N | $CF_3$ | 0 | O | $CH_2C{\equiv}CCH_2CH_3$ | |
| 864 | N | $CF_3$ | 0 | O | $CHFCF_3$ | |
| 865 | N | $CF_3$ | 0 | O | $COOCH_2CH_3$ | |
| 866 | N | $CF_3$ | 0 | O | $CH_2CH_2OH$ | |
| 867 | N | $CF_3$ | 0 | O | $CH_2CH_2OCH_3$ | |
| 868 | N | $CF_3$ | 0 | O | $CH_2COOC(CH_3)_3$ | |
| 869 | N | $CF_3$ | 0 | O | $CH_2SPh$ | |
| 870 | N | $CF_3$ | 0 | O | $CH_2CONHCH_3$ | |
| 871 | N | $CF_3$ | 0 | O | $CH_2CH(OH)CH_2O$ | |
| 872 | N | $CF_3$ | 0 | O | CHO | |
| 873 | N | $CF_3$ | 0 | O | $COCH_3$ | |
| 874 | N | $CF_3$ | 0 | O | $CH_2OC_6H_5$ | |
| 875 | N | $CF_3$ | 0 | O | COPh | |
| 876 | N | $CF_3$ | 0 | O | $CF_2CH_3$ | |
| 877 | N | $CF_3$ | 0 | O | $CH_2CN$ | |
| 878 | N | $CF_3$ | 0 | O | $CH_2CH_2CN$ | |
| 879 | N | $CF_3$ | 0 | O | $CH{=}CF_2$ | |
| 880 | N | $CF_3$ | 0 | O | 2-Furyl | |
| 881 | N | $CF_3$ | 0 | O | OH | |
| 882 | N | $CF_3$ | 0 | O | $OCH_3$ | |
| 883 | N | $CF_3$ | 0 | O | $OCH_2CH_3$ | |
| 884 | N | $CF_3$ | 0 | O | $OCHF_2$ | |
| 885 | N | $CF_3$ | 0 | O | $OCH_2Ph$ | |
| 886 | N | $CF_3$ | 0 | O | $NH_2$ | |
| 887 | N | $CF_3$ | 0 | O | $NHCH_3$ | |
| 888 | N | $CF_3$ | 0 | O | $NHCH_2CH_3$ | |
| 889 | N | $CF_3$ | 0 | O | $N(CH_2CH_3)_2$ | |
| 890 | N | $CF_3$ | 0 | O | $N(CH_2CN)_2$ | |
| 891 | N | $CF_3$ | 0 | O | $N(CH_3)_2$ | |
| 892 | N | $CF_3$ | 0 | O | $NHCOCH_3$ | |
| 893 | N | $CF_3$ | 0 | O | $NHCOCH_2CH_3$ | |
| 894 | N | $CF_3$ | 0 | O | $OSO_2CH_3$ | |
| 895 | N | $CH_2CH_2Cl$ | 0 | O | $CH_2CH_3$ | |
| 896 | N | $CH_2CH_2Cl$ | 0 | O | $NH_2$ | |
| 897 | N | $CH_2Cl$ | 0 | O | $CH_3$ | |
| 898 | N | $CHF_2$ | 0 | O | $CH_3$ | |
| 899 | N | $CHF_2$ | 0 | O | $CH_2CH_3$ | |
| 900 | N | $CHF_2$ | 0 | O | $CH(CH_3)(CH_2)_4CH_3$ | |
| 901 | N | $CHF_2$ | 0 | O | $CH_2CH{=}CH_2$ | |
| 902 | N | $CHF_2$ | 0 | O | $COOCH_2CH_3$ | |
| 903 | N | $CHF_2$ | 0 | O | $NH_2$ | |
| 904 | CH | $CF_3$ | 0 | O | $CH_3$ | 60–61 |
| 905 | CH | $CF_3$ | 1 | O | $CH_3$ | |
| 906 | CH | $CF_3$ | 0 | O | $CH_2CH_3$ | oil |
| 907 | CH | $CF_3$ | 1 | O | $CH_2CH_3$ | oil |
| 908 | CH | $CF_3$ | 0 | O | $(CH_2)_2CH_3$ | oil |
| 909 | CH | $CF_3$ | 1 | O | $(CH_2)_2CH_3$ | oil |
| 910 | CH | $CF_3$ | 0 | O | $CH(CH_3)_2$ | |
| 911 | CH | $CF_3$ | 1 | O | $CH(CH_3)_2$ | |
| 912 | CH | $CF_3$ | 0 | O | $(CH_2)_3CH_3$ | |
| 913 | CH | $CF_3$ | 1 | O | $(CH_2)_3CH_3$ | |
| 914 | CH | $CF_3$ | 0 | O | $CH(CH_3)CH_2CH_3$ | |
| 915 | CH | $CF_3$ | 1 | O | $CH(CH_3)CH_2CH_3$ | |
| 916 | CH | $CF_3$ | 0 | O | $CH_2CH(CH_3)_2$ | |
| 917 | CH | $CF_3$ | 1 | O | $CH_2CH(CH_3)_2$ | |
| 918 | CH | $CF_3$ | 0 | O | $C(CH_3)_3$ | |
| 919 | CH | $CF_3$ | 1 | O | $C(CH_3)_3$ | |

TABLE 3-continued

| No. | X | Y | m | V | R¹ | m.p. [° C.] |
|---|---|---|---|---|---|---|
| 920 | CH | CF₃ | 0 | O | (CH₂)₄CH₃ | |
| 921 | CH | CF₃ | 1 | O | (CH₂)₄CH₃ | |
| 922 | CH | CF₃ | 0 | O | CH(CH₃)(CH₂)₂CH₃ | |
| 923 | CH | CF₃ | 0 | O | (CH₂)₂CH(CH₃)₂ | |
| 924 | CH | CF₃ | 0 | O | CH₂C(CH₃)₃ | |
| 925 | CH | CF₃ | 0 | O | cyclo-C₅H₉ | |
| 926 | CH | CF₃ | 0 | O | cyclo-C₆H₁₁ | |
| 927 | CH | CF₃ | 0 | O | CH₂(3-Thienyl) | oil |
| 928 | CH | CF₃ | 0 | O | CHO | |
| 929 | CH | CF₃ | 0 | O | CH=CH₂ | |
| 930 | CH | CF₃ | 0 | O | CH₂Ph | 61–63 |
| 931 | CH | CF₃ | 0 | O | CH₂CH=C(CH₃)₂ | |
| 932 | CH | CF₃ | 0 | O | CH₂CH=CH₂ | |
| 933 | CH | CF₃ | 0 | O | C(CH₃)=CH₂ | |
| 934 | CH | CF₃ | 0 | O | (CH₂)₅C=CH₂ | |
| 935 | CH | CF₃ | 0 | O | C(=CHCH₃)CH₃ | |
| 936 | CH | CF₃ | 0 | O | CH₂C≡CH | |
| 937 | CH | CF₃ | 0 | O | CH₂CH₂C≡CH₂ | |
| 938 | CH | CF₃ | 0 | O | CH₂C≡CCH₂CH₃ | |
| 939 | CH | CF₃ | 0 | O | (CH₂)₄C≡CH | |
| 940 | CH | CF₃ | 0 | O | CHFCF₃ | |
| 941 | CH | CF₃ | 0 | O | COOCH₂CH₃ | |
| 942 | CH | CF₃ | 0 | O | CH₂CH₂OH | |
| 943 | CH | CF₃ | 0 | O | CH₂CH₂OCH₃ | |
| 944 | CH | CF₃ | 0 | O | CH₂COOC(CH₃)₃ | |
| 945 | CH | CF₃ | 0 | O | CH₂SPh | |
| 946 | CH | CF₃ | 0 | O | CH₂CONHCH₃ | |
| 947 | CH | CF₃ | 0 | O | CH₂CH(OH)CH₂OH | |
| 948 | CH | CF₃ | 0 | O | CH₂COCH₃ | |
| 949 | CH | CF₃ | 0 | O | COCH3 | |
| 950 | CH | CF₃ | 0 | O | CH₂Oph | |
| 951 | CH | CF₃ | 0 | O | COPh | |
| 952 | CH | CF₃ | 0 | O | CF₂CH₃ | |
| 953 | CH | CF₃ | 0 | O | CH₂CN | oil |
| 954 | CH | CF₃ | 0 | O | CH₂CH(—O—)CH₂ | |
| 955 | CH | CF₃ | 0 | O | CH₂(4-OCH₃)Ph | |
| 956 | CH | CF₃ | 0 | O | CH₂CH(OH)CH₂SPh | |
| 957 | CH | CF₃ | 0 | O | CH=CF₂ | |
| 958 | CH | CF₃ | 0 | O | CCl=CHCl | |
| 959 | CH | CF₃ | 0 | O | Ph | 120–121 |
| 960 | CH | CF₃ | 0 | O | 2-Thienyl | 87–89 |
| 961 | CH | CF₃ | 0 | O | OPh | |
| 962 | CH | CF₃ | 0 | O | OH | |
| 963 | CH | CF₃ | 0 | O | OCH₃ | |
| 964 | CH | CF₃ | 0 | O | OCH₂CH₃ | |
| 965 | CH | CF₃ | 0 | O | OCHF₂ | |
| 966 | CH | CF₃ | 0 | O | OCH₂Ph | |
| 967 | CH | CF₃ | 0 | O | SCH₃ | |
| 968 | CH | CF₃ | 0 | O | SPh | |
| 969 | CH | CF₃ | 0 | O | NH₂ | 190–191 |
| 970 | CH | CF₃ | 0 | O | NHCH₃ | |
| 971 | CH | CF₃ | 0 | O | NHCH₂CH₃ | |
| 972 | CH | CF₃ | 0 | O | N(CH₂CH₃)₂ | |
| 973 | CH | CF₃ | 0 | O | N(CH₂CN)₂ | |
| 974 | CH | CF₃ | 0 | O | N(CH₃)₂ | |
| 975 | CH | CF₃ | 0 | O | NHCOCH₃ | |
| 976 | CH | CF₃ | 0 | O | NHCOCH₂CH₃ | |
| 977 | CH | CF₃ | 0 | O | OSO₂CH₃ | |
| 978 | CH | CF₃ | 0 | O | SOCH₂(4-Br)—C₆H₄ | |
| 979 | CH | CF₃ | 0 | O | N(CH₃)COOCH₂Ph | |
| 980 | CH | CF₃ | 0 | NCH₃ | CH₃ | |
| 981 | CH | CF₃ | 0 | NCH₂CH₃ | CH₃ | |
| 982 | CH | CF₃ | 0 | NCH₂CH₃ | CH₂CH₃ | |
| 983 | CH | CF₃ | 0 | NCH₂CN | CH₂CH₃ | |
| 984 | CH | CF₃ | 0 | NCH₂OCH₃ | NHCH₃ | |

TABLE 3-continued

| No. | X | Y | m | V | R¹ | m.p. [° C.] |
|---|---|---|---|---|---|---|
| 985 | CH | CF₃ | 0 | NCH₂OCH₂CH₃ | CN | |
| 986 | CH | CF₃ | 0 | NCH₂CH=CH₂ | CH₃ | |
| 987 | CH | CF₃ | 0 | NCH₂CH=CF₂ | SCH₃ | |
| 988 | CH | CF₃ | 0 | NCH₂OCH₃ | SCH₂CH₃ | |
| 989 | CH | CF₃ | 0 | NCH₂OCH₃ | SCH₂Ph | |
| 990 | CH | CHF₂ | 0 | O | CH₃ | |
| 991 | CH | CHF₂ | 0 | O | CH₂CH₃ | |
| 992 | CH | CHF₂ | 0 | O | (CH₂)₂CH₃ | |
| 993 | CH | CHF₂ | 0 | O | CH₂CH=CH₂ | |
| 994 | CH | CHF₂ | 0 | O | C(CH₃)=CH₂ | |
| 995 | CH | CHF₂ | 0 | O | COOCH₂CH₃ | |
| 996 | CH | CHF₂ | 0 | O | CH₂CONHCH₃ | |
| 997 | CH | CHF₂ | 0 | O | CF₂CH₃ | |
| 998 | CH | CHF₂ | 0 | O | CHO | |
| 999 | CH | CHF₂ | 0 | O | NH₂ | |
| 1000 | CH | CHF₂ | 0 | O | NHCOCH₃ | |
| 1001 | N | CF₂CF₃ | 0 | S | CH₃ | |
| 1002 | N | CF₂CF₃ | 0 | S | CH₂CH₃ | |
| 1003 | N | CF₂CF₃ | 0 | S | (CH₂)₂CH₃ | |
| 1004 | N | CF₃ | 0 | S | CH₃ | |
| 1005 | N | CF₃ | 0 | S | CH₂CH₃ | |
| 1006 | N | CF₃ | 0 | S | (CH₂)₂CH₃ | |
| 1007 | N | CF₃ | 0 | S | CHFCF₃ | |
| 1008 | N | CF₃ | 0 | S | CH₂CH₂OH | |
| 1009 | N | CF₃ | 0 | S | CH₂COOC(CH₃)₃ | |
| 1010 | CH | CF₃ | 0 | S | CH₃ | |
| 1011 | CH | CF₃ | 0 | S | CH₂CH₃ | |
| 1012 | CH | CF₃ | 0 | S | (CH₂)₂CH₃ | |
| 1013 | CH | CF₃ | 0 | S | CHO | |
| 1014 | CH | CF₃ | 0 | S | CHFCF₃ | |
| 1015 | CH | CF₃ | 0 | S | CH₂C≡CH | |
| 1016 | CH | CF₃ | 0 | S | COOCH₂CH₃ | |
| 1017 | CH | CF₃ | 0 | S | CH₂COOC(CH₃)₃ | |
| 1018 | CH | CF₃ | 0 | S | CH₂CN | |

TABLE 4

| No. | X | Y | m | V | R² | R³ | m.p. |
|---|---|---|---|---|---|---|---|
| 1019 | N | (CF₂)₃CHF₂ | 0 | S | H | CH₂CH₃ | |
| 1020 | N | CF₂CF₂CF₃ | 0 | S | H | CH₂CH₃ | |
| 1021 | N | CF₂CF₃ | 0 | S | H | CH₂CH₃ | |
| 1022 | N | CH₂CH₂Cl | 0 | S | H | CH₂CH₃ | |
| 1023 | N | CH₂Cl | 0 | S | H | CH₂CH₃ | |
| 1024 | N | CF₃ | 0 | S | CH₂CH₃ | CH₂CH₃ | |
| 1025 | N | CF₃ | 0 | S | (CH₂)₂CH₃ | H | |
| 1026 | N | CF₃ | 0 | S | CH(CH₃)₂ | H | |
| 1027 | N | CF₃ | 0 | S | CH₂CH(CH₃)₂ | H | |
| 1028 | N | CF₃ | 0 | S | C(CH₃)₃ | H | |
| 1029 | CH | CF₃ | 0 | S | H | CH₃ | oil |

TABLE 4-continued

| No. | X | Y | m | V | R² | R³ | m.p. |
|---|---|---|---|---|---|---|---|
| 1030 | CH | CF₃ | 0 | S | H | CH₂CH₃ | oil |
| 1031 | CH | CF₃ | 0 | S | H | C(CH₃)₃ | oil |
| 1032 | CH | CF₃ | 0 | S | CH₂CH₃ | COOCH₂CH₃ | |
| 1033 | CH | CF₃ | 0 | S | (CH₂)₂CH₃ | COOCH₂CH₃ | |
| 1034 | CH | CF₃ | 0 | S | CH(CH₃)₂ | COOCH₂CH₃ | |
| 1035 | CH | CF₃ | 0 | S | CH(CH₃)₂ | CONHCH₂CH₃ | |
| 1036 | CH | CF₃ | 0 | S | CH(CH₃)₂ | CONHCH₂CH₃ | |
| 1037 | CH | CF₃ | 0 | S | CH(CH₃)₂ | CON(CH₂CH₃)₂ | |
| 1038 | CH | CF₃ | 0 | S | CH(CH₃)₂ | CONH-cyclo-C₃H₇ | |
| 1039 | CH | CF₃ | 0 | S | C(CH₃)₃ | COOCH₂CH₃ | |
| 1040 | CH | CF₃ | 0 | S | H | CONHCH₂CH₃ | |
| 1041 | CH | CF₃ | 0 | S | H | CON(CH₂CH₃)₂ | |
| 1042 | CH | CF₃ | 0 | S | H | COOCH₂CH₃ | oil |
| 1043 | CH | CF₃ | 0 | S | H | CH₂COOCH₂CH₃ | oil |
| 1044 | CH | CF₃ | 0 | S | H | CH₂CHO | |
| 1045 | CH | CF₃ | 0 | S | H | CH₂OCH₃ | |
| 1046 | CH | CF₃ | 0 | S | H | CH₂OCH₂Ph | |
| 1047 | CH | CF₃ | 0 | S | H | H | |
| 1048 | CH | CF₃ | 0 | S | Cyclo-C₅H₉ | H | |
| 1049 | CH | CF₃ | 0 | S | CON(CH₃)₂ | CH₃ | oil |
| 1050 | CH | CF₃ | 0 | S | CH₃ | CH₂CH₂OH | |
| 1051 | CH | CF₃ | 0 | S | CH₃ | CH₂CH₂OCH₃ | |
| 1052 | CH | CF₃ | 0 | S | CH₃ | CH₂CH₂OCH₂Ph | |
| 1053 | CH | CF₃ | 0 | S | CH₃ | CH₂CH₂SPh | |
| 1054 | CH | CF₃ | 0 | S | CH₃ | CH₃ | oil |
| 1055 | CH | CF₃ | 0 | S | CH₃ | CH₂CH₂CHO | |
| 1055 | CH | CF₃ | 0 | S | CH₃ | CH₂CH₂CHNPh | |
| 1057 | CH | CF₃ | 0 | S | CH₃ | CH₂CH₂CONH₂ | |
| 1058 | CH | CF₃ | 0 | S | H | (4-CF₃O)C₆H₄ | 120–121 |
| 1059 | CH | CF₃ | 0 | S | CH₂C≡CH | H | |
| 1060 | CH | CF₃ | 0 | S | CH₂CH₂C≡CH | H | |
| 1061 | CH | CF₃ | 0 | S | CH₂C≡CCH₂CH₃ | H | |
| 1062 | CH | CF₃ | 0 | S | CH₂CH=C(CH₃)₂ | H | |
| 1063 | CH | CF₃ | 0 | S | CH₂CH₂CH=CH₂ | H | |
| 1064 | CH | CF₃ | 0 | S | CH₂CH=CH₂ | H | |
| 1065 | CH | CF₃ | 0 | S | C(CH₃)=CH₂ | H | |
| 1066 | CH | CF₃ | 0 | S | CHFCF₃ | H | |
| 1067 | CH | CF₃ | 0 | S | COOCH₂CH₃ | H | |
| 1068 | CH | CF₃ | 0 | S | CH₂CH₂OH | H | |
| 1069 | CH | CF₃ | 0 | S | CH₂CH₂OCH₃ | H | |
| 1070 | CH | CF₃ | 0 | S | CH₂COOC(CH₃)₃ | H | |
| 1071 | CH | CF₃ | 0 | S | CH₂COCH₃ | H | |
| 1072 | CH | CF₃ | 0 | S | COCH3 | H | |
| 1073 | CH | CF₃ | 0 | S | CH₂OPh | H | |
| 1074 | CH | CF₃ | 0 | S | COPh | H | |
| 1075 | CH | CF₃ | 0 | S | CO(4-Cl)—C₆H₄ | H | |
| 1076 | CH | CF₃ | 0 | S | CF₂CH₃ | H | |
| 1077 | CH | CF₃ | 0 | S | CH₂CN | H | |
| 1078 | CH | CF₃ | 0 | S | CH₂CH₂CN | H | |
| 1079 | N | CF₃ | 0 | S | H | H | |
| 1080 | N | CF₃ | 0 | S | H | CH₂CH₂CN | |
| 1081 | N | CF₃ | 0 | S | H | CH₂CO₂C(CH₃)₃ | |
| 1082 | N | CF₃ | 0 | S | H | CH₂CHO | |
| 1083 | N | CF₃ | 0 | S | H | CH₂CH₂OH | |
| 1084 | N | CF₃ | 0 | S | H | CH₂CH₂OCH₃ | |
| 1085 | N | CF₃ | 0 | S | Cyclo-C₅H₉ | H | |
| 1086 | N | CF₃ | 0 | S | CH₃ | COOCH₂CH₃ | |
| 1087 | N | CF₃ | 0 | S | CH₃ | COOH | |
| 1088 | N | CF₃ | 0 | S | CH₃ | CONH₂ | |
| 1089 | N | CF₃ | 0 | S | CH₃ | CONHCH₂CH₃ | |
| 1090 | N | CF₃ | 0 | S | CH₃ | CON(CH₂CH₃)₂ | |
| 1091 | N | CF₃ | 0 | S | CH₃ | CONHCH₃ | |
| 1092 | N | CF₃ | 0 | S | CH₃ | CONHCH₂CN | |

TABLE 4-continued

| No. | X | Y | m | V | R² | R³ | m.p. |
|---|---|---|---|---|---|---|---|
| 1093 | N | CF₃ | 0 | S | CH₃ | CON(CH₂CN)₂ | |
| 1094 | N | CF₃ | 0 | S | CH₃ | CON(CH₃)₂ | |
| 1095 | N | CF₃ | 0 | S | CH₂C≡CH | OCH₂CH₃ | |
| 1096 | N | CF₃ | 0 | S | CH₂CH₂C≡CH | OCH₂CH₃ | |
| 1097 | N | CF₃ | 0 | S | CH₂C≡CCH₂CH₃ | OCH₂CH₃ | |
| 1098 | N | CF₃ | 0 | S | CH₂CH=C(CH₃)₂ | OCH₂CH₃ | |
| 1099 | N | CF₃ | 0 | S | CH₂CH₂CH=CH₂ | OCH₂CH₃ | |
| 1100 | N | CF₃ | 0 | S | CH₂CH=CH₂ | OCH₂CH₃ | |
| 1101 | N | CF₃ | 0 | S | C(CH₃)=CH₂ | OCH₂CH₃ | |
| 1102 | N | CF₃ | 0 | S | CHFCF₃ | OCH₂CH₃ | |
| 1103 | N | CF₃ | 0 | S | COOCH₂CH₃ | OCH₂CH₃ | |
| 1104 | N | CF₃ | 0 | S | CH₂CH₂OH | OCH₂CH₃ | |
| 1105 | N | CF₃ | 0 | S | CH₂CH₂OCH₃ | OCH₂CH₃ | |
| 1106 | N | CF₃ | 0 | S | CH₂COOC(CH₃)₃ | OCH₂CH₃ | |
| 1107 | N | CF₃ | 0 | S | CH₂COCH₃ | H | |
| 1108 | N | CF₃ | 0 | S | COCH3 | H | |
| 1109 | N | CF₃ | 0 | S | CH₂Oph | H | |
| 1110 | N | CF₃ | 0 | S | COPh | H | |
| 1111 | N | CF₃ | 0 | S | CO(4-Cl)—C₆H₄ | H | |
| 1112 | N | CF₃ | 0 | S | CF₂CH₃ | H | |
| 1113 | N | CF₃ | 0 | S | CH₂CN | H | |
| 1114 | N | CF₃ | 0 | S | CH₂CH₂CN | H | |
| 1115 | CH | CF₃ | 0 | O | CH₂CH₃ | CH₂CH₃ | |
| 1116 | CH | CF₃ | 0 | O | (CH₂)₂CH₃ | H | |
| 1117 | CH | CF₃ | 0 | O | H | CH₂CH₃ | oil |
| 1118 | CH | CF₃ | 0 | O | CH(CH₃)₂ | COOCH₂CH₃ | |
| 1119 | CH | CF₃ | 0 | O | CH(CH₃)₂ | COOH | |
| 1120 | CH | CF₃ | 0 | O | CH(CH₃)₂ | CONH₂ | |
| 1121 | CH | CF₃ | 0 | O | CH(CH₃)₂ | CH₃ | |
| 1122 | CH | CF₃ | 0 | O | C(CH₃)₃ | H | |
| 1123 | CH | CF₃ | 0 | O | H | CH₃ | |
| 1124 | CH | CF₃ | 0 | O | H | cyclo-C₅H₉ | |
| 1125 | CH | CF₃ | 0 | O | H | CH₂CH₂CH₃ | |
| 1126 | CH | CF₃ | 0 | O | H | Ph | 103–10 |
| 1127 | CH | CF₃ | 0 | O | H | 2-Pyridyl | |
| 1128 | CH | CF₃ | 0 | O | H | 2-Furyl | |
| 1129 | CH | CF₃ | 0 | O | Cyclo-C₅H₉ | H | |
| 1130 | CH | CF₃ | 0 | O | CH₃ | COOCH₂CH₃ | |
| 1131 | CH | CF₃ | 0 | O | CH₃ | COOH | |
| 1132 | CH | CF₃ | 0 | O | CH₃ | CONH₂ | |
| 1133 | CH | CF₃ | 0 | O | CH₃ | CONHCH₂CH₃ | |
| 1134 | CH | CF₃ | 0 | O | CH₃ | CON(CH₂CH₃)₂ | |
| 1135 | CH | CF₃ | 0 | O | CH₃ | CONHCH₃ | |
| 1136 | CH | CF₃ | 0 | O | CH₃ | CONHCH₂CN | |
| 1137 | CH | CF₃ | 0 | O | CH₃ | CON(CH₂CN)₂ | |
| 1138 | CH | CF₃ | 0 | O | CH₃ | CON(CH₃)₂ | |
| 1139 | CH | CF₃ | 0 | O | CH₂C≡CH | H | |
| 1140 | CH | CF₃ | 0 | O | CH₂CH₂C≡CH | H | |
| 1141 | CH | CF₃ | 0 | O | CH₂C≡CCH₂CH₃ | H | |
| 1142 | CH | CF₃ | 0 | O | CH₂CH=C(CH₃)₂ | H | |
| 1143 | CH | CF₃ | 0 | O | CH₂CH₂C≡CH | H | |
| 1144 | CH | CF₃ | 0 | O | CH₂CH=CH₂ | H | |
| 1145 | CH | CF₃ | 0 | O | C(CH₃)=CH₂ | H | |
| 1146 | CH | CF₃ | 0 | O | CHFCF₃ | H | |
| 1147 | CH | CF₃ | 0 | O | COOCH₂CH₃ | H | |
| 1148 | CH | CF₃ | 0 | O | CH₂CH₂OH | H | |
| 1149 | CH | CF₃ | 0 | O | CH₂CH₂OCH₃ | H | |
| 1150 | CH | CF₃ | 0 | O | CH₂COOC(CH₃)₃ | H | |
| 1151 | CH | CF₃ | 0 | O | CH₂COCH₃ | H | |
| 1152 | CH | CF₃ | 0 | O | COCH3 | H | |
| 1153 | CH | CF₃ | 0 | O | CH₂Oph | H | |
| 1154 | CH | CF₃ | 0 | O | COPh | H | |
| 1155 | CH | CF₃ | 0 | O | CO(4-Cl)—C₆H₄ | H | |

TABLE 4-continued

| No. | X | Y | m | V | R² | R³ | m.p. |
|---|---|---|---|---|---|---|---|
| 1156 | CH | CF₃ | 0 | O | CF₂CH₃ | H | |
| 1157 | CH | CF₃ | 0 | O | CH₂CN | H | |
| 1158 | CH | CF₃ | 0 | O | CH₂CH₂CN | H | |
| 1159 | N | CF₃ | 0 | O | CH₂CH₃ | CH₂CH₃ | |
| 1160 | N | CF₃ | 0 | O | (CH₂)₂CH₃ | H | |
| 1161 | N | CF₃ | 0 | O | CH(CH₃)₂ | CONH₂ | |
| 1162 | N | CF₃ | 0 | O | CH(CH₃)₂ | CH₃ | |
| 1163 | N | CF₃ | 0 | O | C(CH₃)₃ | H | |
| 1164 | N | CF₃ | 0 | O | H | CH₃ | |
| 1165 | N | CF₃ | 0 | O | H | CH₂CH₃ | |
| 1166 | N | CF₃ | 0 | O | H | CH₂CH₂CH₃ | |
| 1167 | N | CF₃ | 0 | O | H | Ph | |
| 1168 | N | CF₃ | 0 | O | H | 2-Pyridyl | |
| 1169 | N | CF₃ | 0 | O | H | 2-Furyl | |
| 1170 | N | CF₃ | 0 | O | Cyclo-C₅H₉ | H | |
| 1171 | N | CF₃ | 0 | O | CH₃ | COOCH₂CH₃ | |
| 1172 | N | CF₃ | 0 | O | CH₃ | COOH | |
| 1173 | N | CF₃ | 0 | O | CH₃ | CONH₂ | |
| 1174 | N | CF₃ | 0 | O | CH₃ | CONHCH₂CH₃ | |
| 1175 | N | CF₃ | 0 | O | CH₃ | CON(CH₂CH₃)₂ | |
| 1176 | N | CF₃ | 0 | O | CH₃ | CONHCH₃ | |
| 1177 | N | CF₃ | 0 | O | CH₃ | CONHCH₂CN | |
| 1178 | N | CF₃ | 0 | O | CH₃ | CON(CH₂CN)₂ | |
| 1179 | N | CF₃ | 0 | O | CH₃ | CON(CH₃)₂ | |
| 1180 | N | CF₃ | 0 | O | CH₂C≡CH | H | |
| 1181 | N | CF₃ | 0 | O | CH₂CH₂C≡CH | H | |
| 1182 | N | CF₃ | 0 | O | CH₂C≡CCH₂CH₃ | H | |
| 1183 | N | CF₃ | 0 | O | CH₂CH=C(CH₃)₂ | H | |
| 1184 | N | CF₃ | 0 | O | CH₂CH₂CH=CH₂ | H | |
| 1185 | N | CF₃ | 0 | O | CH₂CH=CH₂ | H | |
| 1186 | N | CF₃ | 0 | O | C(CH₃)=CH₂ | H | |
| 1187 | N | CF₃ | 0 | O | CHFCF₃ | H | |
| 1188 | N | CF₃ | 0 | O | COOCH₂CH₃ | H | |
| 1189 | N | CF₃ | 0 | O | CH₂CH₂OH | H | |
| 1190 | N | CF₃ | 0 | O | CH₂CH₂OCH₃ | H | |
| 1191 | N | CF₃ | 0 | O | CH₂COOC(CH₃)₃ | H | |
| 1192 | N | CF₃ | 0 | O | CH₂COCH₃ | H | |
| 1193 | N | CF₃ | 0 | O | COCH3 | H | |
| 1194 | N | CF₃ | 0 | O | CH₂Oph | H | |
| 1195 | N | CF₃ | 0 | O | COPh | H | |
| 1196 | N | CF₃ | 0 | O | CO(4-Cl)—C₆H₄ | H | |
| 1197 | N | CF₃ | 0 | O | CF₂CH₃ | H | |
| 1198 | N | CF₃ | 0 | O | CH₂CN | H | |
| 1199 | N | CF₃ | 0 | O | CH₂CH₂CN | H | |
| 1200 | N | CF₃ | 0 | O | CH₂NHSO₂CH₃ | CH₃ | |
| 1201 | N | CF₃ | 0 | O | (CH₂)₂NHSO₂CH₃ | CH₃ | |
| 1202 | N | CF₃ | 0 | O | CH₂NHSO₂CH₂CH₃ | CH₃ | |
| 1203 | N | CF₃ | 0 | O | H | CH₂NHSO₂CH₂Ph | |
| 1204 | CH | CF₃ | 0 | O | (CH₂)₄NHSO₂CF₃ | CH₃ | |
| 1205 | CH | CF₃ | 0 | O | (CH₂)₂S(CH₂)₂CH₃ | CH₂CH₂CH₃ | |
| 1206 | CH | CF₃ | 0 | O | (CH₂)₄S(CH₂)₄OCH₃ | CH₃ | |
| 1207 | CH | CF₃ | 0 | S | CH₃ | (CH₂)₂S(CH₂)₂CN | |
| 1208 | CH | CF₃ | 0 | S | CH₂NHSO₂CH₂CH₃ | CH₃ | |
| 1209 | CH | CF₃ | 0 | S | CH₂NHSO₂CH₂Ph | CH₂CH₂CH₃ | |
| 1210 | CH | CF₃ | 0 | S | (CH₂)₂NHSO₂CH₃ | CF₃ | |
| 1211 | CH | CF₃ | 0 | S | H | CH₂NHSO₂CH₃ | |
| 1212 | CH | CF₃ | 0 | S | CH(CH₃)CH₂NHPh | CF₃ | |
| 1213 | CH | CF₃ | 0 | S | (CH₂)₂S(2-F)—C₆H₄ | CH₂CH₂CH₃ | |
| 1214 | CH | CF₃ | 0 | S | (CH₂)₆NHCH₂)₆OCH₃ | CF₃ | |
| 1215 | CH | CF₃ | 0 | S | H | (CH₂)₂NH-(2-F)—C₆H₄ | |
| 1216 | CH | CF₃ | 0 | S | (CH₂)₃NHCH₂CN | H | |
| 1217 | CH | CF₃ | 0 | S | (CH₂)₂O(3-Cl)—C₆H₄ | CH₃ | |

TABLE 4-continued

| No. | X | Y | m | V | R² | R³ | m.p. |
|---|---|---|---|---|---|---|---|
| 1218 | CH | CF₃ | 0 | S | CF₃ | (CH₂)₆NHCH₂CF₃ | |
| 1219 | CH | CF₃ | 0 | S | CH₃ | (CH₂)₂O(3-CH₃)—C₆H₄ | |
| 1220 | CH | CF₃ | 0 | O | H | CH₂NHPh | |
| 1221 | CH | CF₃ | 0 | O | CH₃ | (CH₂)₄S(2-Br)—C₆H₄ | |
| 1222 | CH | CF₃ | 0 | O | (CH₂)₆NH(CH₂)₂OCH₃ | CH₃ | |
| 1223 | CH | CF₃ | 0 | O | (CH₂)₂NH(CH₂)₄OCH₃ | H | |
| 1224 | CH | CF₃ | 0 | O | CF₃ | (CH₂)₃NH-(4-CN)—C₆H₄ | |
| 1225 | CH | CF₃ | 0 | O | (CH₂)₄NHCH₂CF₃ | CH₃ | |
| 1226 | CH | CF₃ | 0 | O | C₂F₅ | (CH₂)₂O(3-CH₃)—C₆H₄ | |
| 1227 | CH | CF₃ | 0 | O | (CH₂)₄NHCH₂CN | H | |
| 1228 | CH | CF₃ | 0 | O | (CH₂)₃O(4-Cl)—C₆H₄ | C₂F₅ | |

TABLE 5

| No. | X | Y | V | R⁴ | R⁵ | R⁶ | R⁷ | m.p. [° C.] |
|---|---|---|---|---|---|---|---|---|
| 1229 | CH | CF₃ | O | H | H | H | H | oil |
| 1230 | CH | CF₃ | O | H | H | CH₃ | H | oil |
| 1231 | CH | CF₃ | O | H | H | CH₂CH₃ | H | oil |
| 1232 | CH | CF₃ | O | H | H | CH(CH₃)₂ | H | |
| 1233 | CH | CF₃ | O | H | H | CH₂CH(CH₃)₂ | H | |
| 1234 | CH | CF₃ | O | H | H | CH(CH₃)CH₂CH₃ | H | |
| 1235 | CH | CF₃ | O | H | H | CH₂OH | H | |
| 1236 | CH | CF₃ | O | H | H | CH(OH)CH₃ | H | |
| 1237 | CH | CF₃ | O | H | H | CH₂SH | H | |
| 1238 | CH | CF₃ | O | H | H | CH₂CH₂SCH₃ | H | |
| 1239 | CH | CF₃ | O | H | H | (CH₂)₃NH₂ | H | |
| 1240 | CH | CF₃ | O | H | H | (CH₂)₄NH₂ | H | |
| 1241 | CH | CF₃ | O | H | H | CH=CH₂ | H | |
| 1242 | CH | CF₃ | O | H | H | (CH₂)₂COOCH₃ | H | |
| 1243 | CH | CF₃ | O | H | H | (CH₂)₂COOH | H | |
| 1244 | CH | CF₃ | O | H | H | (CH₂)₂CONH₂ | H | |
| 1245 | CH | CF₃ | S | CH₃ | CH₃ | H | H | |
| 1246 | CH | CF₃ | O | H | H | CH₃ | CH₃ | oil |
| 1247 | CH | CF₃ | O | H | H | CH₂COOCH₃ | H | |
| 1248 | CH | CF₃ | O | H | H | CH₂COOH | H | |
| 1249 | CH | CF₃ | O | H | H | CH₂CONH₂ | H | |
| 1250 | CH | CF₃ | O | H | H | CH₂Ph | H | |
| 1251 | CH | CF₃ | O | H | H | CH₂-(4-OH)—C₆H₄ | H | |
| 1252 | CH | CF₃ | O | H | H | CH₂-(3-Indolyl) | H | |
| 1253 | CH | CF₃ | O | CH₃ | CH₃ | H | H | oil |
| 1254 | CH | CF₃ | O | CH₃ | H | H | H | oil |
| 1255 | CH | CF₃ | O | CH₃ | H | H | Ph | |
| 1256 | CH | CF₃ | O | H | | (CH₂)₄ | H | |
| 1257 | CH | CF₃ | NH | H | | (CH₂)₄ | H | |
| 1258 | CH | CF₃ | NCH₃ | H | | (CH₂)₄ | H | |
| 1259 | CH | CF₃ | NCH₂C₆H₄ | H | | (CH₂)₄ | H | |
| 1260 | CH | CF₃ | NCH(CH₃)₂ | H | | (CH₂)₄ | H | |
| 1261 | CH | CF₃ | O | Ph | H | Ph | H | |
| 1262 | CH | CF₃ | NH | Ph | H | Ph | H | |

TABLE 5-continued

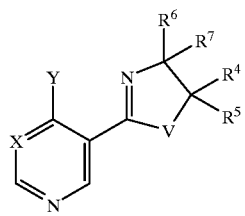

| No. | X | Y | V | R⁴ | R⁵ | R⁶ | R⁷ | m.p. [° C.] |
|---|---|---|---|---|---|---|---|---|
| 1263 | CH | CF₃ | NCH₃ | Ph | H | Ph | H | |
| 1264 | CH | CF₃ | NCH₂C₆H₄ | Ph | H | Ph | H | |
| 1265 | N | CF₃ | O | H | H | CH₂CH₃ | H | oil |
| 1266 | N | CF₃ | O | H | H | CH(CH₃)₂ | H | |
| 1267 | N | CF₃ | O | H | H | CH₂CH(CH₃)₂ | H | |
| 1268 | N | CF₃ | O | H | H | CH₂COOH | H | |
| 1269 | N | CF₃ | O | H | H | CH₂COOCH₃ | H | |
| 1270 | N | CF₃ | O | H | H | CH₂CONH₂ | H | |
| 1271 | N | CF₃ | O | CH₃ | CH₃ | H | H | |
| 1272 | N | CF₃ | O | H | (CH | | H | |
| 1273 | N | CF₃ | O | H | H | CH₂CH₂SCH₃ | H | |
| 1274 | CH | CF₃ | S | H | H | H | H | oil |

TABLE 6

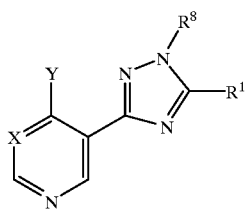

| No. | X | Y | R⁸ | R¹ | m.p. [° C.] |
|---|---|---|---|---|---|
| 1275 | CH | CF₃ | CH₃ | SH | 209–210 |
| 1276 | CH | CF₃ | CH₃ | SCH₃ | |
| 1277 | CH | CF₃ | CH₃ | SCH₂CH₃ | |
| 1278 | CH | CF₃ | CH₃ | S(CH₂)₂CH₃ | |
| 1279 | CH | CF₃ | CH₃ | SCH(CH₃)₂ | |
| 1280 | CH | CF₃ | CH₃ | SPh | |
| 1281 | CH | CF₃ | CH₃ | S(CH₂)₃CH₃ | |
| 1282 | CH | CF₃ | CH₃ | SCH(CH₃)CH₂CH₃ | |
| 1283 | CH | CF₃ | CH₃ | SCH₂CH(CH₃)₂ | |
| 1284 | CH | CF₃ | CH₃ | OH | 119–120 |
| 1285 | CH | CF₃ | CH₃ | OCH₃ | |
| 1286 | CH | CF₃ | CH₃ | OCH₂CH₃ | |
| 1287 | CH | CF₃ | CH₃ | OCHF₂ | |
| 1288 | CH | CF₃ | CH₃ | OCH₂Ph | |
| 1289 | CH | CF₃ | CH₃ | OCONHPh | |
| 1290 | CH | CF₃ | CH₃ | OCONH-(4-F)—C₆H₄ | |
| 1291 | CH | CF₃ | CH₃ | OCONH-(3,5-di-Cl)—C₆H₃ | |
| 1292 | CH | CF₃ | CH₂CN | OCH₃ | |
| 1293 | CH | CF₃ | CH₂CN | OCH₂CH₃ | |
| 1294 | CH | CF₃ | CH₂CN | OCHF₂ | |
| 1295 | CH | CF₃ | CH₂CN | OCH₂Ph | |
| 1296 | CH | CF₃ | CH₂CN | OCONHPh | |
| 1297 | CH | CF₃ | CH₂CN | OCONH-(4-F)—C₆H₄ | |
| 1298 | CH | CF₃ | CH₂OCH₂CH₃ | OCH₃ | |
| 1299 | CH | CF₃ | CH₂OCH₂CH₃ | OCH₂CH₃ | |
| 1300 | CH | CF₃ | CH₂OCH₂CH₃ | OCHF₂ | |
| 1301 | CH | CF₃ | CH₂OCH₂CH₃ | OCH₂Ph | |
| 1302 | CH | CF₃ | CH₂OCH₂CH₃ | OCONHPh | |
| 1303 | CH | CF₃ | H | CH₃ | 203–204 |
| 1304 | CH | CF₃ | H | CH₂CH₃ | 134–135 |
| 1305 | CH | CF₃ | H | (CH₂)₂CH₃ | |
| 1306 | CH | CF₃ | H | CH(CH₃)₂ | |
| 1307 | CH | CF₃ | H | Cyclo-C₃H₅ | |
| 1308 | CH | CF₃ | H | (CH₂)₃CH₃ | |
| 1309 | CH | CF₃ | H | CH(CH₃)CH₂CH₃ | |

TABLE 6-continued

[Structure: pyridine ring with X, Y substituents connected to a 1,2,4-triazole bearing R⁸ on N and R¹]

| No. | X | Y | R⁸ | R¹ | m.p. [° C.] |
|---|---|---|---|---|---|
| 1310 | CH | CF₃ | H | CH₂CH(CH₃)₂ | |
| 1311 | CH | CF₃ | H | CH=CH₂ | |
| 1312 | CH | CF₃ | H | CH₂CH=C(CH₃)₂ | |
| 1313 | CH | CF₃ | H | CH₂CH₂CH=CH₂ | |
| 1314 | CH | CF₃ | H | CH₂CH=CH₂ | |
| 1315 | CH | CF₃ | H | C(CH₃)=CH₂ | |
| 1316 | CH | CF₃ | H | CHFCF₃ | |
| 1317 | CH | CF₃ | H | COOCH₂CH₃ | |
| 1318 | CH | CF₃ | H | CH₂CH₂OH | |
| 1319 | CH | CF₃ | H | CH₂CH₂OCH₃ | |
| 1320 | CH | CF₃ | H | CH₂COOC(CH₃)₃ | |
| 1321 | CH | CF₃ | CH₃ | CH₂COOC(CH₃)₃ | |
| 1322 | CH | CF₃ | CH₂CN | CH₂COOC(CH₃)₃ | |
| 1323 | CH | CF₃ | CH₂OCH₂CH₃ | CH₂COOC(CH₃)₃ | |
| 1324 | CH | CF₃ | H | CH₂SPh | |
| 1325 | CH | CF₃ | H | CH₂CONHCH₃ | |
| 1326 | CH | CF₃ | H | CH₂COCH₃ | |
| 1327 | CH | CF₃ | H | COCH3 | |
| 1328 | CH | CF₃ | H | CH₂Oph | |
| 1329 | CH | CF₃ | H | COPh | |
| 1330 | CH | CF₃ | H | CO(3-Cl)—C₆H₄ | |
| 1331 | CH | CF₃ | H | CF₂CH₃ | |
| 1332 | CH | CF₃ | H | CH₂CN | |
| 1333 | CH | CF₃ | H | CH₂CH₂CN | |
| 1334 | CH | CF₃ | H | CH₂CH(—O—)CH₂ | |
| 1336 | CH | CF₃ | H | CH₂(4-OCH₃)Ph | |
| 1337 | N | CF₃ | CH₃ | SH | |
| 1338 | N | CF₃ | CH₃ | SCH₃ | |
| 1339 | N | CF₃ | CH₃ | SCH₂CH₃ | |
| 1340 | N | CF₃ | CH₃ | SPh | |
| 1341 | N | CF₃ | CH₃ | SCH₂CH(CH₃)₂ | |
| 1342 | N | CF₃ | CH₃ | OH | |
| 1343 | N | CF₃ | CH₃ | OCH₃ | |
| 1344 | N | CF₃ | CH₃ | OCH₂CH₃ | |
| 1345 | N | CF₃ | CH₃ | OCH₂Ph | |
| 1346 | N | CF₃ | CH₃ | OCONHPh | |
| 1347 | N | CF₃ | CH₂CN | OCH₃ | |
| 1348 | N | CF₃ | CH₂CN | OCH₂CH₃ | |
| 1349 | N | CF₃ | CH₂CN | OCH₂Ph | |
| 1350 | N | CF₃ | CH₂CN | OCONHPh | |
| 1351 | N | CF₃ | CH₂OCH₂CH₃ | OCH₃ | |
| 1352 | N | CF₃ | CH₂OCH₂CH₃ | OCH₂Ph | |
| 1353 | N | CF₃ | CH₂OCH₂CH₃ | OCONHPh | |
| 1354 | N | CF₃ | H | CH₃ | |
| 1355 | N | CF₃ | H | CH₂CH₃ | |
| 1356 | N | CF₃ | H | (CH₂)₂CH₃ | |
| 1357 | N | CF₃ | H | CH(CH₃)₂ | |
| 1358 | N | CF₃ | H | (CH₂)₃CH₃ | |
| 1359 | N | CF₃ | H | CH(CH₃)CH₂CH₃ | |
| 1360 | N | CF₃ | H | CH₂CH(CH₃)₂ | |
| 1361 | N | CF₃ | H | CH₂C=C(CH₃)₂ | |
| 1362 | N | CF₃ | H | CH₂CH=CH₂ | |
| 1363 | N | CF₃ | H | C(CH₃)H=CH₂ | |
| 1364 | N | CF₃ | H | COOCH₂CH₃ | |
| 1365 | N | CF₃ | H | CH₂CH₂OH | |
| 1366 | N | CF₃ | H | CH₂CH₂OCH₃ | |
| 1367 | N | CF₃ | H | CH₂COOC(CH₃)₃ | |
| 1368 | N | CF₃ | H | CH₂SPh | |
| 1369 | N | CF₃ | H | CH₂CONHCH₃ | |
| 1370 | N | CF₃ | H | CH₂COCH₃ | |
| 1371 | N | CF₃ | H | COCH3 | |
| 1372 | N | CF₃ | H | CH₂Oph | |
| 1373 | N | CF₃ | H | COPh | |

TABLE 6-continued

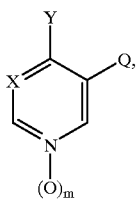

| No. | X | Y | R⁸ | R¹ | m.p. [° C.] |
|---|---|---|---|---|---|
| 1374 | N | CF₃ | H | CH₂CN | |
| 1375 | N | CF₃ | H | CH₂CH₂CN | |
| 1376 | CH | CF₃ | CH₃ | CH₂CH₃ | oil |

C. Biological examples

Example 1

A Petri dish whose bottom is covered with filter paper and which contains about 5 ml of culture medium is prepared. Pieces of filter paper with about 30, 24-hour-old eggs of the American tobacco budworm (Heliothis virescens) are dipped into an aqueous solution of the formulated preparation to be examined for 5 seconds and subsequently placed in the Petri dish. A further 200 µl of the aqueous solution are spread over the culture medium. The Petri dish is closed and then kept at about 25° C. in a climatized chamber. After 6 days' storage, the effect of the preparation on the eggs and the larvae which may have hatched from these is determined. At a concentration of 300 ppm (based on the content of active compound), the preparations of Example Nos. 79 and 88 effect a mortality of 90–100%.

Example 2

Germinated broad bean seeds (Vicia faba) with radicles are transferred into brown glass bottles filled with tap water and subsequently populated with approximately 100 black bean aphids (Aphis fabae) belegt. Plants and aphids are then dipped for 5 seconds into an aqueous solution of the formulated preparation to be examined. After the solution has dripped off, plant and animals are kept in a climatized chamber (16 hours of light/day, 25° C., 40–60% relative atmospheric humidity. After 3 and 6 days' storage, the effect of the preparation on the aphids is determined. At a concentration of 300 ppm (based on the content of active compound), the preparations of Example Nos. 79, 78, 80, 81, 83, 84, 88, 133, 135, 136, 137, 138, 139, 1117, 1229, 1230, 1231, 1246 and 1254 effect a mortality of 90–100% among the aphids.

Example 3

The leaves of 12 rice plants having a stem length of 8 cm are dipped for 5 seconds into an aqueous solution of the formulated preparation to be examined. After the solution has dripped off, the rice plants treated in this manner are placed in a Petri dish and populated with approximately 20 larvae (L3 stage) of the rice leaf hopper species Nilaparvata lugens. The Petri dish is closed and stored in a climatized chamber (16 hours of light/day, 25° C., 4060% relative atmospheric humidity). After 6 days' storage, the mortality among the leaf hopper larvae is determined. At a concentration of 300 ppm (based on the content of active compound), the preparations of Example Nos. 88 139 and 927 effect a mortality of 90–100%.

Example 4

Germinated broad bean seeds (Vicia faba) with radicles are transferred into brown glass bottles filled with tap water. Four milliliters of an aqueous solution of the formulated preparation to be examined are pipetted into the brown glass bottle. The broad bean is subsequently heavily populated with approximately 100 black bean aphids (Aphis fabae). Plant and animals are then stored in a climatized chamber (16 hours of light/day, 25° C., 40–60% relative atmospheric humidity). After 3 and 6 days' storage, the root-systemic activity of the preparation on the aphids is determined. At a concentration of of 30 ppm (based on the content of active compound), the Preparations of Example Nos. 78, 79, 80, 81, 83, 84, 88,133, 135, 136, 137, 138, 139,187, 1117, 1229,1230, 1231,1246 and 1254 effect a mortality of 90–100% among the aphids by root-systemic action.

What is claimed is:

1. A 4-haloalkyl-3-heterocyclylpyridine or 4-haloalkyl-5-heterocyclyl-pyrimidine of the formula I if desired in the form of its salt (I)

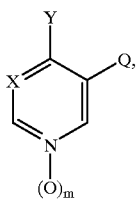

wherein

Y is halo-$C_1$–$C_6$alkyl;

x is CH or N;

m is 0 or 1;

Q is a 5-membered heterocyclic group

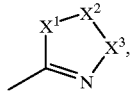

in which

| a) $X^1$ = W, | $X^2$ = $NR^a$, | $X^3$ = $CR^bR^1$ | or |
| b) $X^1$ = $NR^a$, | $X^2$ = $CR^bR^1$, | $X^3$ = W | or |
| c) $X^1$ = V, | $X^2$ = $CR^aR^1$, | $X^3$ = $NR^b$ | or |
| d) $X^1$ = V, | $X^2$ = $CR^aR^2$, | $X^3$ = $CR^bR^3$ | or |

-continued

| e) $X^1$ = V, | $X^2$ = $CR^4R^5$, | $X^3$ = $CR^6R^7$ | or |
| f) $X^1$ = $NR^a$, | $X^2$ = $CR^bR^1$, | $X^3$ = $NR^8$; | |

$R^a$ and $R^b$ together are a bond

V is oxygen, sulfur or $NR^9$;

W is oxygen or sulfur;

$R^1$ is hydrogen, $(C_1–C_{20})$-alkyl, $(C_2–C_{20})$-alkenyl, $(C_2–C_{20})$-alkynyl, $(C_3–C_8)$-cycloalkyl, $(C_4–C_8)$-cycloalkenyl, $(C_6–C_8)$-cycloalkynyl, where the six last-mentioned radicals are optionally substituted by one or more radicals from the group halogen, cyano, nitro, hydroxyl, $—C(=W)R^{10}$, $—C(=NOR^{10})R^{10}$, $—C(=NNR^{10}_2)R^{10}$, $—C(=W)OR^{10}$, $—C(=W)NR^{10}_2$, $—OC(=W)R^{10}$, $—OC(=W)OR^{10}$, $—NR^{10}C(=W)R^{10}$, $—N[C(=W)R^{10}]_2$, $—NR^{10}C(=W)OR^{10}$, $—C(=W)NR^{10}—NR^{10}_2$, $—C(=W)NR^{10}—NR^{10}[C(=W)R^{10}]$, $—NR^{10}—C(=W)NR^{10}_2$, $—NR^{10}—NR^{10}C(=W)R^{10}$, $—NR^{10}—N[C(=W)R^{10}]_2$, $—N[(C=W)R^{10}]$, $—NR^{10}_2$, $—NR^{10}—NR^{10}[(C=W)R^{10}]_2$, $—NR^{10}—NR^{10}[(C=W)WR^{10}]$, $—NR^{10}—R^{10}[(C=W)NR^{10}]_2$, $—NR^{10}(C=NR^{10})R^{10}$, $—NR^{10}(C=NR^{10})NR^{10}_2$, $—O—NR^{10}_2$, $—O—NR^{10}(C=W)R^{10}$, $—SO_2NR^{10}_2$, $—NR^{10}SiO_2R^{10}$, $—SO_2OR^{10}$, $—OSO_2R^{10}$, $—OR^{10}$, $—NR^{10}_2$, $—SR^{10}$, $—SiR^{10}_3$, $—SeR^{10}$, $—PR^{10}_2$, $—P(=W)R^{10}_2$, $—SOR^{10}$, $—SO_2R^{10}$, $—PW_2R^{10}_2$, $—PW_3R^{10}_2$, aryl and heterocyclyl, the two last-mentioned radicals optionally being substituted by one or more radicals from the group $(C_1–C_6)$-alkyl, $(C_2–C_6)$-alkenyl, $(C_2–C_6)$-alkynyl, $(C_3–C_8)$-cycloalkyl, $(C_4–C_8)$-cycloalkenyl, $(C_6–C_8)$cycloalkynyl, $(C_1–C_6)$-haloalkyl, $(C_2–C_6)$-haloalkenyl, $(C_2–C_6)$-haloalkynyl, halogen, $—OR^{10}$, $—NR^{10}_2$, $—SR^{10}$, $—SiR^{10}_3$, $—C(=W)R^{10}$, $—C(=W)OR^{10}$, $—C(=W)NR^{10}_2$, $—SOR^{10}$, $—SO_2R^{10}$, nitro, cyano and hydroxyl; aryl, which is optionally substituted by one or more radicals from the group $(C_1–C_6)$-alkyl, $(C_2–C_6)$-alkenyl, $(C_2–C_6)$-alkynyl, $(C_3–C_8)$-cycloalkyl, $(C_4–C_8)$-cycloalkenyl and $(C_6C_8)$-cycloalkynyl, where these six abovementioned radicals are optionally substituted by one or more radicals from the group halogen, cyano, nitro, $—C(=W)R^{10}$, $—C(=W)OR^{10}$, $—C(=W)NR^{10}_2$, $—OR^{10}$, $—NR^{10}_2$, $—SR^{10}$, $—SOR^{10}$ and $—SO_2R^{10}$;

halogen, cyano, nitro, $—C(=W)R^{10}$, $—C(=W)OR^{10})R^{10}$, $—C(=NNR^{10}_2)R^{10}$, $—C(=W)OR^{10}$, $—C(=W)NR^{10}_2$, $—OC(=W)R^{10}$, $—OC(=W)OR^{10}$, $—NR^{10}C(=W)R^{10}$, $—N[C(=W)R^{10}]_2$, $—NR^{10}C(=W)OR^{10}$, $—OR^{10}$, $—NR^{10}_2$, $—SR^{10}$, $—SiR^{10}_3$, $—PR^{10}_2$, $—SOR^{10}$, $—SO_2R^{10}$, $—PW_2R^{10}_2$ and $—PW_3R^{10}_2$, heterocyclyl, which is optionally substituted by one or more radicals from the group $(C_1–C_6)$-alkyl, $(C_2–C_6)$-alkenyl, $(C_2–C_6)$-alkynyl, $(C_3–C_8)$-cycloalkyl, $(C_4–C_8)$-cycloalkenyl and $(C_6–C_8)$-cycloalkynyl, where the six abovementioned radicals are optionally substituted by one or more radicals from the group cyano, nitro, halogen, $—C(=W)R^{10}$, $—C(=W)OR^{10}$, $—C(=W)NR^{10}_2$, $—NR^{10}C(=W)R^{10}$, $—N[C(=W)R^{10}]_2$, $—OC(=W)R^{10}$, $—OC(=W)OR^{10}$, $—OR^{10}$, $—NR^{10}_2$, $—SR^{10}$, $—SOR^{10}$ and $—SO_2R^{10}$;

halogen, cyano, nitro, $—C(=W)R^{10}$, $—C(=W)OR^{10}$, $—C(=W)NR^{10}_2$, $—OC(=W)R^{10}$, $—OR^{10}$, $—NR^{10}_2$, $—SR^{10}$, $—SOR^{10}$ and $—SO_2R^{10}$, $—OR^{10}$, $—NR^{10}_2$, $—SR^{10}$, $—SOR^{10}$, $—SO_2R^{10}$, $—C(=W)R^{10}$, $—C(=NOR^{10})R^{10}$, $—C(=NNR^{10}_2)R^{10}$, $—C(=W)OR^{10}$, $—C(=W)NR^{10}_2$, $—OC(=W)R^{10}$, $—OC(=W)OR^{10}$, $—NR^{10}C(=W)R^{10}$, $—N[C(=W)R^{10}]_2$, $—NR^{10}C(=W)OR^{10}$, $—C(=W)NR^{10}—NR^{10}_2$, $—C(=W)NR^{10}—NR^{10}C(=W)R^{10}$, $—NR^{10}—C(=W)NR^{10}_2$, $—NR^{10}—NR^{10}C(=W)R^{10}$, $—NR^{10}—NC(=W)R^{10}_2$, $—N(C=W)R^{10}—NR^{10}_2$, $—NR^{10}-NR^{10}[(C=W)R^{10}]$, $—NR^{10}—NR^{10}[(C=W)WR^{10o}$, $—NR^{10}—NR^{10}[(C=W)NR^{10}_2]$, $—NR^{10}(C=NR^{10})R^{10}$, $—NR^{10}(C=NR^{10})NR^{10}_2$, $—O—NR^{10}_2$, $—O—NR^{10}(C=W)R^{10}$, $—SO_2NR^{10}_2$, $—NR^{10}SO_2R^{10}$, $—SO_2R^{10}$, $—OSO_2R^{10}$, $—SC(=W)R^{10}$, $—SC(=W)OR^{10}$, $—SC(=W)R^{10}$, $—PR^{10}_2$, $—PW_2R^{10}_2$, $—PW_3R^{10}_2$, $SiR^{10}_3$ or halogen;

$R^2$ and $R^3$ independently of one another have the definitions given in $R^1$; $R^2$ and $R^3$ together form a 5- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals $R^1$;

$R^4$ and $R^6$ independently of one another have the definitions given in $R^1$; $R^4$ and $R^6$ together form a 4- to 7-membered ring which may be partially or fully unsaturated and may be interrupted by one or more atoms from the group nitrogen, oxygen and sulfur, the oxygen atoms not being directly adjacent to one another, and the ring optionally being substituted by one or more, but at most 5, radicals $R^1$;

$R^5$ and $R^7$ independently of one another are hydrogen, $(C_1–C_{20})$-alkyl, $(C_2–C_{20})$-alkenyl, $(C_2–C_{20})$-alkynyl, $(C_3–C_8)$-cycloalkyl, $(C_4–C_8)$-cycloalkenyl, $(C_6–C_8)$-cycloalkynyl, where the six last-mentioned radicals are optionally substituted by one or more radicals from the group halogen, cyano, nitro, hydroxyl, $—C(=W)R^{10}$, $—C(=NOR^{10})R^{10}$, $—C(=NNR^{10}_2)R^{10}$, $—C(=W)OR^{10}$, $—C(=W)NR^{10}_2$, $—OC(=W)R^{10}$, $—OC(=W)OR^{10}$, $—NR^{10}C(=W)R^{10}$, $—N[C(=W)R^{10}]_2$, $—NR^{10}C(=W)OR^{10}$, $—C(=W)NR^{10}$-$NR^{10}_2$, $—C(=W)NR^{10}—NR^{10}[C(=W)R^{10}]$, $—NR^{10}—C(=W)NR^{10}$, $—NR^{10}—NR^{10}C(=W)R^{10}$, $—NR^{10}—N[C(=W)R^{10}]_2$, $—N[(C=W)R^{10}]-NR^{10}_2$, $—NR^{10}-NR^{10}[(C=W)R^{10}]$, $—NR^{10}—NR^{10}[(C=W)NR^{10}]$, $—NR^{10}O—NR^{10}[(C=W)NR^{10}]_2$, $—N R^{10}(C=N R^{10})R^{10}$, $—NR^{10}(C=NR^{10})NR^{10}_2$, $—O—NR^{10}_2$, $—O—NR^{10}(C=W)R^{10}$, $—OR^{10}$, $—NR^{10}_2$, $—SR^{10}$, $—SiR^{10}_3$, $—SeR^{10}$, $—PR^{10}_2$, $—P(=W)R^{10}_2$, $—SOR^{10}$, $—SO_2R^{10}$, $—PW_2R^{10}_2$, $—PW_3R^{10}_2$, aryl and heterocyclyl, of which the two mentioned last are optionally substituted by one or more radicals from the group $(C_1–C_6)$-alkyl, $(C_2–C_6)$-alkenyl, $(C_2–C_6)$-alkynyl, $(C_3–C_8)$-cycloalkyl, $(C_4–C_8)$-cycloalkenyl, $(C_4–C_8)$-cycloalkynyl, $(C_1–C_6)$-haloalkyl, $(C_2–C_6)$-haloalkenyl, $(C_2–C_6)$-haloalkynyl, halogen, $—OR^{10}$, $—NR^{10}_2$, $—SR^{10}$, $—SiR^{10}_3$, $—C(=W)R^{10}$, $—C(=W)OR^{10}$, $—C(=W)NR^{10}_2$, $—SOR^{10}$, $—SO_2R^{10}$, nitro, cyano and hydroxyl; aryl, which is optionally substituted by one or more radicals from the group $(C_1–C_6)$-alkyl, $(C_2–C_6)$-alkenyl, $(C_2–C_6)$-alkynyl, $(C_3–C_8)$-cycloalkyl, $(C_4–C_8)$-cycloalkenyl and $(C_6–C_8)$-cycloalkynyl, where these six abovementioned radicals are optionally substituted by one or more radicals from the group halogen, cyano, nitro, $—C(=W)R^{10}$, $—C(=W)OR^{10}$, $—C(=W)NR^{10}_2$, $—OR^{10}$, $—NR^{10}_2$, $—SR^{10}$, $—SOR^{10}$ and $—SO_2R^{10}$, halogen, cyano, nitro, $—C(=W)R^{10}$, —C(=NOR$^{10}$)R$^{10}$, —C(=NNR$^{10}_2$)R$^{10}$, —C(=W)OR$^{10}$, —C(=W)NR$^{10}_2$, —OC(=W)R$^{10}$, —OC(=W)OR$^{10}$, —NR$^{10}$C(=W)R$^{10}$, —N[C(=W)R$^{10}$]$_2$, —NR$^{10}$C(=W)OR$^{10}$, —OR$^{10}$, —NR$^{10}_2$, —SR$^{10}$, —SiR$^{10}_3$, —PR$^{10}_2$, —SORR$^{10}$, —SO$_2$R$^{10}$, —PW$_2$R$^{10}_2$ and —PW$_3$R$^{10}_2$; pyridyl, which is optionally substituted by one or more radicals from the group (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl and (C$_6$–C$_8$)-cycloalkynyl, where the six abovementioned radicals are optionally substituted by one or more radicals from the group cyano, nitro, halogen, —C(=W)R$^{10}$, —C(=W)OR$^{10}$, —C(=W)NR$^{10}_2$, —OR$^{10}$, —NR$^{10}_2$, —SR$^{10}$, —SOR$^{10}$ and —SO$_2$R$^{10}$; halogen, cyano, nitro, —C(=W)R$^{10}$, —C(=W)OR$^{10}$, —C(=W)NR$^{10}_2$, —OC(=W)R$^{10}$, —OR$^{10}$, —NR$^{10}_2$, —SR$^{10}$, —SOR$^{10}$ and —SO$_2$R$^{10}$, —C(=W)R$^{10}$, —C(=NOR$^{10}$)R$^{10}$, —C(=NNR$^{10}_2$)R$^{10}$, —C(=W)OR$^{10}$, —C(=W)NR$^{10}_2$ or halogen;

R$^4$ and R$^5$ together form a 4- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals R$^{10}$; R$^4$ and R$^5$ together form one of the groups =O, =S or =N—R$^9$;

R$^6$ and R$^7$ together form a 5- to 7-membered ring which may be partially unsaturated and may be interrupted by one or more atoms from the group nitrogen, oxygen and sulfur, oxygen atoms not being directly adjacent to one another, and the ring optionally being substituted by one or more, but at most 5, radicals R$^1$; R$^6$ and R$^7$ together form one of the groups =O, =S or =N—R$^9$;

R$^8$ is hydrogen, (C$_1$–C$_6$)-alkyl, (C$_2$–C$_6$)-alkenyl, (C$_2$–C$_6$)-alkynyl, (C$_3$–C$_8$)-cycloalkyl, (C$_4$–C$_8$)-cycloalkenyl, (C$_3$–C$_8$)-cycloalkyl-(C$_1$–C$_4$)-alkyl, (C$_4$–C$_8$)-cycloalkenyl-(C$_1$–C$_4$)-alkyl, (C$_3$–C$_8$)-cycloalkyl-(C$_2$–C$_4$)-alkenyl, (C$_4$–C$_8$)-cycloalkenyl-(C$_1$–C$_4$)-alkenyl, (C$_1$–C$_6$)-alkyl-(C$_3$–C$_8$)-cycloalkyl, (C$_2$–C$_6$)-alkenyl-C$_3$–C$_8$)-cycloalkyl, (C$_2$–C$_6$)-alkynyl-(C$_3$–C$_8$)-cycloalkyl, (C$_1$–C$_6$)-alkyl-(C$_4$–C$_8$)-cycloalkenyl, (C$_2$–C$_6$)-alkenyl-(C$_4$–C$_8$)-cycloalkenyl, where the fourteen last-mentioned radicals are optionally substituted by one or more radicals from the group halogen, cyano, nitro, hydroxyl, thio, amino, formyl, (C$_1$–C$_6$)-alkoxy, (C$_2$–C$_6$)-alkenyloxy, (C$_2$–C$_6$)-alkynyloxy, (C$_1$–C$_6$)-haloalkyloxy, (C$_2$–C$_6$)-haloalkenyloxy, (C$_2$–C$_6$)-haloalkynyloxy, (C$_3$–C$_8$)-cycloalkoxy, (C$_4$–C$_8$)-cycloalkenyloxy, (C$_3$–C$_8$)-halocycloalkoxy, (C$_4$–C$_8$)-halocycloalkenyloxy, (C$_3$–C$_8$)-cycloalkyl-(C$_1$–C$_4$)-alkoxy, (C$_4$–C$_8$)-cycloalkenyl-(C$_1$–C$_4$)-alkoxy, (C$_3$–C$_8$)-cycloalkyl-(C$_2$–C$_4$)-alkenyloxy, (C$_4$–C$_8$)-cycloalkenyl-(C$_1$–C$_4$)-alkenyloxy, (C$_1$–C$_6$)-alkyl-(C$_3$–C$_8$)-cycloalkoxy, (C$_2$–C$_6$)-alkenyl-(C$_3$–C$_8$)-cycloalkoxy, (C$_2$–C$_4$)-alkynyl-(C$_3$–C$_8$)-cycloalkoxy, (C$_1$–C$_6$)-alkyl-(C$_4$–C$_8$)-cycloalkenyloxy, (C$_2$–C$_6$)-alkenyl-(C$_4$–C$_8$)-cycloalkenyloxy, (C$_1$–C$_4$)-alkoxy-(C$_1$–C$_6$)-alkoxy, (C$_1$–C$_4$)-alkoxy-(C$_2$–C$_6$)-alkenyloxy, carbamoyl, (C$_1$–C$_6$)-mono- or dialkylcarbamoyl, (C$_1$–C$_6$)-mono- or dihaloalkylcarbamoyl, (C$_3$–C$_6$)-mono- or dicycloalkylcarbamoyl, (C$_1$–C$_6$)-alkoxycarbonyl, (C$_3$–C$_8$)-cycloalkoxycarbonyl, (C$_1$–C$_6$)-alkanoyloxy, (C$_3$–C$_8$)-cycloalkanoyloxy, (C$_1$–C$_6$)-haloalkoxycarbonyl, (C$_1$–C$_6$)-haloalkanoyloxy, (C$_1$–C$_6$)-alkaneamido, (C$_1$–C$_6$)-haloalkaneamido, (C$_2$–C$_6$)-alkeneamido, (C$_3$–C$_8$)-cycloalkaneamido, (C$_3$–C$_8$)-cycloalkyl-(C$_1$–C$_4$)-alkaneamido, (C$_1$–C$_6$)-alkylthio, (C$_2$–C$_6$)-alkenylthio, (C$_2$–C$_6$)-alkynylthio, (C$_1$–C$_6$)-haloalkylthio, (C$_2$–C$_6$)-haloalkenylthio, (C$_2$–C$_6$)-haloalkynylthio, (C$_3$–C$_8$)-cycloalkylthio, (C$_4$–C$_8$)-cycloalkenylthio, (C$_3$–C$_8$)-halocycloalkylthio, (C$_4$–C$_8$)-halocycloalkenylthio, (C$_3$–C$_8$)-cycloalkyl-(C$_1$–C$_4$)-alkylthio, (C$_4$–C$_8$)-cycloalkenyl-(C$_1$–C$_4$)-alkylthio, (C$_3$–C$_8$)-cycloalkyl-(C$_2$–C$_4$)-alkenylthio, (C$_4$–C$_8$)-cycloalkenyl-(C$_1$–C$_4$)-alkenylthio, (C$_1$–C$_6$)-alkyl-(C$_3$–C$_8$)-cycloalkylthio, (C$_2$–C$_6$)-alkenyl-(C$_3$–C$_8$)-cycloalkylthio, (C$_2$–C$_6$)-alkynyl-(C$_3$–C$_8$)-cycloalkylthio, (C$_1$–C$_6$)-alkyl-(C$_4$–C$_8$)-cycloalkenylthio, (C$_2$–C$_6$)-alkenyl-(C$_4$–C$_8$)-cycloalkenylthio, (C$_1$–C$_6$)-alkylsulfinyl, (C$_2$–C$_6$)-alkenylsulfinyl, (C$_2$–C$_6$)-alkynylsulfinyl, (C$_1$–C$_6$)-haloalkylsulfinyl, (C$_2$–C$_6$)-haloalkenylsulfinyl, (C$_2$–C$_6$)-haloalkynylsulfinyl, (C$_3$–C$_8$)-cycloalkylsulfinyl, (C$_4$–C$_8$)-cycloalkenylsulfinyl, (C$_3$–C$_8$)-halocycloalksulfinyl, (C$_4$–C$_8$)-halocycloalkenylsulfinyl, (C$_3$–C$_8$)-cycloalkyl-C$_1$–C$_4$)-alkylsulfinyl, (C$_4$–C$_8$)-cyloalkenyl-(C$_1$–C$_4$)-alkylsulfinyl, (C$_3$–C$_8$)-cycloalkyl-(C$_2$–C$_4$)-alkenylsulfinyl, (C$_4$–C$_8$)-cycloalkenyl-(C$_1$–C$_4$)-alkenylsulfinyl, (C$_1$–C$_6$)-alkyl-(C$_3$–C$_8$)-cycloalkylsulfinyl, (C$_2$–C$_6$)-alkenyl-(C$_3$–C$_8$)-cycloalkylsulfinyl, (C$_2$–C$_6$)-alkynyl-C$_3$–C$_8$)-cycloalkylsulfinyl, (C$_1$–C$_6$)-alkyl-(C$_4$–C$_8$)-cycloalkenylsulfinyl, (C$_2$–CB)-alkenyl-(C$_4$–C$_8$)-cycloalkenylsulfinyl, (C$_1$–C$_6$)-alkylsulfonyl, (C$_2$–C$_6$)-alkenylsulfonyl, (C$_2$–C$_6$)-alkynylsulfonyl, (C$_1$–C$_6$)-haloalkylsulfonyl, (C$_2$–C$_6$)-haloalkenylsulfonyl, (C$_2$–C$_6$)-haloalkynylsulfonyl, (C$_3$–C$_8$)-cycloalkylsulfonyl, (C$_4$–C$_8$)-cycloalkenylsulfonyl, (C$_3$–C$_8$)-halocycloalkylsulfonyl, (C$_4$–C$_8$)-halocycloalkenylsulfonyl, (C$_3$–C$_8$)-cycloalkyl-(C$_1$–C$_4$)-alkylsulfonyl, (C$_4$–C$_8$)-cycloalkenyl-(C$_1$–C$_4$)-alkyl sulfonyl, (C$_3$–C$_8$)-cycloalkyl-(C$_2$–C$_4$)-alkenylsulfonyl, (C$_4$–C$_8$)-cycloalkenyl-(C$_1$–C$_4$)-alkenylsulfonyl, (C$_1$–C$_6$)-alkyl-(C$_3$–C$_8$)-cycloalkylsulfonyl, (C$_2$–C$_6$)-alkenyl-(C$_3$–C$_8$)-cycoalkylsulfonyl, (C$_2$–C$_6$)-cycloalkenyl-(C$_3$–C$_8$)-cycloalkylsulfonyl, (C$_1$–C$_6$)-alkyl-(C$_4$–C$_8$)-cycloalkenylsulfonyl, (C$_2$–C$_6$)-alkenyl-(C$_4$–C$_8$)-cycloalkenylsulfonyl, (C$_1$–C$_6$,)-alkylamino, (C$_2$–C$_6$)-alkenylamino, (C$_2$–C$_6$)-alkynylamino, (C$_1$–C$_6$)-haloalkylamino, (C$_2$–C$_6$)-haloalkenylamino, (C$_2$–C$_6$)-haloalkynylamino, (C$_3$–C$_8$)-cycloalkylamino, (C$_4$–C$_8$)-cycloalkenylamino, (C$_3$–C$_8$)-halocycloalkamino, (C$_4$–C$_8$)-halocycloalkenylamino, (C$_3$–C$_8$)-cycloalkyl-(C$_1$–C$_4$)-alkylamino, (C$_4$–C$_8$)-cycloalkenyl-(C$_1$–C$_4$)-alkylamino, (C$_3$–C$_8$)-cycloalkyl-(C$_2$–C$_4$)-alkenylamino, (C$_4$–C$_8$)-cycloalkenyl-(C$_1$–C$_4$)-alkenylamino, (C$_1$–C$_6$)-alkyl-(C$_3$–C$_8$)-cycloalkylamino, (C$_2$–C$_6$)-alkenyl-(C$_3$–C$_8$)-cycloalkylamino, (C$_2$–C$_6$)-alkynyl-(C$_3$–C$_8$)-cycloalkylamino, (C$_1$–C$_6$)-alkyl-(C$_4$–C$_8$)-cycloalkenylamino, (C$_2$–C$_6$)-alkenyl-(C$_4$–C$_8$)-cycloalkenylamino, (C$_1$–C$_6$)-trialkylsilyl, aryl, aryloxy, arylthio, arylamino, arylcarbamoyl, aroyl, aroyloxy, aryloxycarbonyl, aryl-(C$_1$–C$_4$)-alkoxy, aryl-(C$_2$–C$_4$)-alkenyloxy, aryl-(C$_1$–C$_4$)-alkylthio, aryl-(C$_2$–C$_4$)-alkenylthio, aryl-(C$_1$–C$_4$)-alkylamino, aryl-(C$_2$–C$_4$)-alkenylamino, aryl-(C$_1$–C$_6$)-dialkylsilyl, diaryl-(C$_1$–C$_6$)-alkylsilyl, triarylsilyl and 5- or 6-membered heterocyclyl; of which the nineteen last-mentioned radicals are optionally substituted in their cyclic moiety by one or more substituents from the group halogen, cyano, nitro, amino, hydroxyl, thio, ($C_1$–$C_4$)-alkyl, ($C_1$–$C_4$)-haloalkyl, ($C_1$–$C_4$)-alkoxy, ($C_1$–$C_4$)-haloalkoxy, ($C_1$–$C_4$)-alkylthio, ($C_1$–$C_4$)-haloalkylthio, ($C_1$–$C_4$)-alkylamino, ($C_1$–$C_4$)-haloalkylamino, formyl and ($C_1$–$C_4$)-alkanoyl; aryl, which is optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, carbamoyl, ($C_1$–$C_6$)-mono- or dialkylcarbamoyl, ($C_1$–$C_6$)-alkoxycarbonyl, ($Ci$–$C_6$)-alkanoyloxy, ($C_1$–$C_6$)-mono- or dihaloalkylcarbamoyl, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_1$–$C_6$)-alkylthio, ($C_2$–$C_6$)-alkenylthio, ($C_2$–$C_6$)-alkynylthio, ($C_1$–$C_6$)-haloalkylthio, ($C_2$–$C_6$)-haloalkenylthio, ($C_2$–$C_6$)-haloalkynylthio, ($C_3$–$C_8$)-cycloalkylthio, ($C_4$–$C_8$)-cycloalkenylthio, ($C_3$–$C_8$)-halocycloalkthio, ($C_3$–$C_8$)-halocycloalkenylthio, ($C_1$–$C_6$)-alkylsulfinyl, ($C_2$–$C_6$)-alkenylsulfinyl, ($C_2$–$C_6$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_1$–$C_6$)-alkylsulfonyl, ($C_2$–$C_6$)-alkenylsulfonyl, ($C_2$–$C_6$)-alkynylsulfonyl, ($C_1$–$C_6$)-haloalkylsulfonyl, ($C_2$–$C_6$)-haloalkenylsulfonyl, ($C_2$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalksulfonyl, ($C_4$–$C_8$)-halocycloalkenylsulfonyl, ($C_1$–$C_6$)-alkylamino, ($C_2$–$C_6$)-alkenylamino, ($C_2$–$C_6$)-alkynylamino, ($C_1$–$C_6$)-haloalkylamino, ($C_2$–$C_6$)-haloalkenylamino, ($C_2$–$C_6$)-haloalkynylamino, ($C_3$–$C_8$)-cycloalkylamino, ($C_4$–$C_8$)-cycloalkenylamino, ($C_3$–$C_8$)-halocycloalkamino and ($C_4$–$C_8$)-halocycloalkenylamino; —C(=W)$R^{10}$, $OR^{10}$ or $NR^{11}_2$;

$R^9$ is ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_3$–$C_8$)-cycloalkyl-($C_1$–$C_4$)-alkyl, ($C_4$–$C_8$)-cycloalkenyl-($C_1$–$C_4$)-alkyl, ($C_3$–$C_8$)-cycloalkyl-($C_2$–$C_4$)-alkenyl, ($C_4$–$C_8$)-cycloalkenyl-($C_1$–$C_4$)-alkenyl, where the nine last-mentioned radicals are optionally substituted by one or more radicals from the group halogen, cyano, ($C_1$–$C_6$)-alkoxy, ($C_2$–$C_6$)-alkenyloxy, ($C_2$–$C_6$) alkynyloxy and ($C_1$–$C_6$)-haloalkyloxy;

$R^{10}$ is hydrogen, ($C_1$–$C_6$)-alkyl, ($C_2$–$C_6$)-alkenyl, ($C_2$–$C_6$)-alkynyl, ($C_3$–$C_8$)-cycloalkyl, ($C_4$–$C_8$)-cycloalkenyl, ($C_3$–$C_8$)-cycloalkyl-($C_1$–$C_4$)-alkyl, ($C_4$–$C_8$)-cycloalkenyl-($C_1$–$C_4$)-alkyl, ($C_3$–$C_8$)-cycloalkyl-($C_2$–$C_4$)-alkenyl, ($C_4$–$C_8$)-cycloalkenyl-($C_1$–$C_4$)-alkenyl, ($C_1$–$C_6$)-alkyl-($C_3$–$C_8$)-cycloalkyl, ($C_2$–$C_6$)-alkenyl-($C_3$–$C_8$)-cycloalkyl, ($C_2$–$C_6$)-alkynyl-($C_3$–$C_8$)-cycloalkyl, ($C_1$–$C_6$)-alkyl-($C_4$–$C_8$)-cycloalkenyl, ($C_2$–$C_6$)-alkenyl-($C_4$–$C_8$)-cycloalkenyl, where the fourteen last-mentioned radicals are optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, ($C_3$–$C_8$)-cycloalkyl-($C_1$–$C_4$)-alkoxy, ($C_4$–$C_8$)-cycloalkenyl-($C_1$–$C_4$)-alkoxy, ($C_3$–$C_8$)-cycloalkyl-($C_2$–$C_4$)-alkenyloxy, ($C_4$–$C_8$)-cycloalkenyl-($C_1$–$C_4$)-alkenyloxy, ($C_1$–$C_6$)-alkyl-($C_3$–$C_8$)-cycloalkoxy, ($C_2$–$C_6$)-alkenyl-($C_3$–$C_8$)-cycloalkoxy, ($C_2$–$C_6$)-alkynyl-($C_3$–$C_8$)-cycloalkoxy, ($C_1$–$C_6$)-alkyl-($C_4$–$C_8$)-cycloalkenyloxy, ($C_2$–$C_6$)-alkenyl-($C_4$–$C_8$)-cycloalkenyloxy, ($C_1$–$C_4$)-alkoxy-($C_1$–$C_6$)-alkoxy, ($C_1$–$C_4$)-alkoxy-($C_2$–$C_6$)-alkenyloxy, carbamoyl, ($C_1$–$C_6$)-mono- or dialkylcarbamoyl, ($C_1$–$C_6$)-mono- or dihaloalkylcarbamoyl, ($C_3$–$C_8$)-mono- or dicycloalkylcarbamoyl, ($C_1$–$C_6$)-alkoxycarbonyl, ($C_3$–$C_8$)-cycloalkoxycarbonyl, ($C_1$–$C_6$)-alkanoyloxy, ($C_3$–$C_8$)-cycloalkanoyloxy, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_3$–$C_8$)-cycloalkaneamido, ($C_3$–$C_8$)-cycloalkyl-($C_1$–$C_4$)-alkaneamido, ($C_1$–$C_6$)-alkylthio, ($C_2$–$C_6$)-alkenylthio, ($C_2$–$C_6$)-alkynylthio, ($C_1$–$C_6$)-haloalkylthio, ($C_2$–$C_6$)-haloalkenylthio, ($C_2$–$C_6$)-haloalkynylthio, ($C_3$–$C_8$)-cycloalkylthio, ($C_4$–$C_8$)-cycloalkenylthio, ($C_3$–$C_8$)-halocycloalkthio, ($C_4$–$C_8$)-halocycloalkenylthio, ($C_3$–$C_8$)-cycloalkyl-($C_1$–$C_4$)-alkylthio, ($C_4$–$C_8$)-cycloalkenyl-($C_1$–$C_4$)-alkylthio, ($C_3$–$C_8$)-cycloalkyl-($C_2$–$C_4$)-alkenylthio, ($C_4$–$C_8$)-cycloalkenyl-$C_1$–$C_4$)-alkenylthio, ($C_1$–$C_6$)-alkyl-($C_3$–$C_8$)-cycloalkylthio, ($C_2$–$C_6$)-alkenyl-($C_3$–$C_8$)-cycloalkylthio, ($C_2$–$C_6$)-alkynyl-($C_3$–$C_8$)-cycloalkylthio, ($C_1$–$C_6$)-alkyl-($C_4$–$C_8$)-cycloalkenylthio, ($C_2$–$C_6$)-alkenyl-($C_4$–$C_8$)-cycloalkenylthio, ($C_1$–$C_6$)-alkylsulfinyl, ($C_2$–$C_6$)-alkenylsulfinyl, ($C_2$–$C_6$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_3$–$C_8$)-cycloalkyl-($C_1$–$C_4$)-alkylsulfinyl, ($C_4$–$C_8$)-cycloalkenyl-($C_1$–$C_4$)-alkylsulfinyl, ($C_3$–$C_8$)-cycloalkyl-($C_2$–$C_4$)-alkenylsulfinyl, ($C_4$–$C_8$)-cycloalkenyl-($C_1$–$C_4$)-alkenylsulfinyl, ($C_1$–$C_6$)-alkyl-($C_3$–$C_8$)-cycloalkylsulfinyl, ($C_2$–$C_6$)-alkenyl-($C_3$–$C_8$)-cycloalkylsulfinyl, ($C_2$–$C_6$)-alkynyl-($C_3$–$C_8$)-cycloalkylsulfinyl, ($C_1$–$C_6$)-alkyl-($C_4$–$C_8$)-cycloalkenyl-sulfinyl, ($C_2$–$C_6$)-alkenyl-($C_4$–$C_8$)-cycloalkenylsulfinyl, ($C_1$–$C_6$)-alkylsulfonyl, ($C_2$–$C_6$)-alkenylsulfonyl, ($C_2$–$C_6$)-alkynylsulfonyl, ($C_1$–$C_6$)-haloalkylsulfonyl, ($C_2$–$C_6$)-haloalkenylsulfonyl, ($C_2$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalksulfonyl, ($C_4$–$C_8$)-halocycloalkenylsulfonyl, ($C_3$–$C_8$)-cycloalkyl-($C_1$–$C_4$)-alkylsulfonyl, ($C_4$–$C_8$)-cycloalkenyl-($C_1$–$C_4$)-alkylsulfonyl, ($C_3$–$C_8$)-cycloalkyl-($C_2$–$C_4$)-alkenylsulfonyl, ($C_4$–$C_8$)-cycloalkenyl-($C_1$–$C_4$)-alkenylsulfonyl, ($C_1$–$C_6$)-alkyl-($C_3$–$C_8$)-cycloalkylsulfonyl, ($C_2$–$C_6$)-alkenyl-($C_3$–$C_8$)-cycloalkylsulfonyl, ($C_2$–$C_6$)-alkynyl-$C_3$–$C_8$)-cycloalkylsulfonyl, ($C_1$–$C_6$)-alkyl-($C_4$–$C_8$)-cycloalkenylsulfonyl, ($C_2$–$C_6$)-alkenyl-($C_4$–$C_8$) cycloalkenylsulfonyl, ($C_1$–$C_6$)-alkylamino, ($C_2$–$C_6$)-alkenylamino, ($C_2$–$C_6$)-alkynylamino, ($C_1$–$C_6$)-haloalkylamino, ($C_2$–$C_6$)-haloalkenylamino, ($C_2$–$C_6$)-haloalkynylamino, ($C_3$–$C_8$)-cycloalkylamino, ($C_4$–$C_8$)-cycloalkenylamino, ($C_3$–$C_8$)-halocycloalkamino, ($C_4$–$C_8$)-halocycloalkenylamino, ($C_3$–$C_8$)-cycloalkyl-($C_1$–$C_4$)-alkylamino, ($C_4$–$C_8$)-cycloalkenyl-($C_1$–$C_4$)-alkylamino, ($C_3$–$C_8$)-cycloalkyl-($C_2$–$C_4$)-alkenylamino, ($C_4$–$C_8$)-cycloalkenyl-($C_1$–$C_4$)-alkenylamino, ($C_1$–$C_6$)-alkyl-($C_3$–$C_8$)-cycloalkylamino, ($C_2$–$C_6$)-alkenyl-($C_3$–$C_8$)-cycloalkylamino, ($C_2$–$C_6$)-alkynyl-($C_3$–$C_8$)-cycloalkylamino, ($C_1$–$C_6$)-alkyl-($C_4$–$C_8$)-cycloalkenylamino, ($C_2$–$C_6$)-alkenyl-($C_4$–$C_8$)-cycloalkenylamino, ($C_1$–$C_6$)-trialkylsilyl, aryl, aryloxy, arylthio, arylamino, aryl-($C_1$–$C_4$)-alkoxy, aryl-($C_2$–$C_4$)-alkenyloxy, aryl-($C_1$–$C_4$)-alkylthio, aryl-($C_2$–$C_4$)-alkenylthio, aryl-($C_1$–$C_4$)-alkylamino, aryl-($C_2$–$C_4$)-alkenylamino, aryl-($C_1$–$C_6$)-dialkylsilyl, diaryl-($C_1$–$C_6$)-alkylsilyl, triarylsilyl and 5- or 6-membered heterocycyl, where the cyclic moiety of the fourteen last-mentioned radicals is optionally substituted by one or more radicals from the group halogen, cyano, nitro, amino, hydroxyl, thio, ($C_1$–$C_4$)-alkyl, ($C_1$–$C_4$)-haloalkyl, ($C_3$–$C_8$)-cycloalkyl, ($C_1$–$C_4$)-alkoxy, ($C_1$–$C_4$)-haloalkoxy, ($C_1$–$C_4$)-alkylthio, ($C_1$–$C_4$)-haloalkylthio, ($C_1$–$C_4$)-alkylamino, ($C_1$–$C_4$)-haloalkylamino, formyl and ($C_1$–$C_4$)-alkanoyl; aryl, 5- or 6-membered heteroaromatic, where the two last-mentioned radicals are optionally substituted by one or more radicals from the group halogen, cyano, nitro, hydroxyl, thio, amino, formyl, ($C_1$–$C_6$)-alkoxy, ($C_2$–$C_6$)-alkenyloxy, ($C_2$–$C_6$)-alkynyloxy, ($C_1$–$C_6$)-haloalkyloxy, ($C_2$–$C_6$)-haloalkenyloxy, ($C_2$–$C_6$)-haloalkynyloxy, ($C_3$–$C_8$)-cycloalkoxy, ($C_4$–$C_8$)-cycloalkenyloxy, ($C_3$–$C_8$)-halocycloalkoxy, ($C_4$–$C_8$)-halocycloalkenyloxy, carbamoyl, ($C_1$–$C_6$)-mono- or dialkylcarbamoyl, ($C_1$–$C_6$)-alkoxycarbonyl, ($C_1$–$C_6$)-alkanoyloxy, ($C_1$–$C_6$)-mono- or dihaloalkylcarbamoyl, ($C_1$–$C_6$)-haloalkoxycarbonyl, ($C_1$–$C_6$)-haloalkanoyloxy, ($C_1$–$C_6$)-alkaneamido, ($C_1$–$C_6$)-haloalkaneamido, ($C_2$–$C_6$)-alkeneamido, ($C_1$–$C_6$)-alkylthio, ($C_2$–$C_6$)-alkenylthio, ($C_2$–$C_6$)-alkynylthio, ($C_1$–$C_6$)-haloalkylthio, ($C_2$–$C_6$)-haloalkenylthio, ($C_2$–$C_6$)-haloalkynylthio, ($C_3$–$C_8$)-cycloalkylthio, ($C_4$–$C_8$)-cycloalkenylthio, ($C_3$–$C_8$)-halocycloalkthio, ($C_4$–$C_8$)-halocycloalkenylthio, ($C_1$–$C_6$)-alkylsulfinyl, ($C_2$–$C_6$)-alkenylsulfinyl, ($C_2$–$C_6$)-alkynylsulfinyl, ($C_1$–$C_6$)-haloalkylsulfinyl, ($C_2$–$C_6$)-haloalkenylsulfinyl, ($C_2$–$C_6$)-haloalkynylsulfinyl, ($C_3$–$C_8$)-cycloalkylsulfinyl, ($C_4$–$C_8$)-cycloalkenylsulfinyl, ($C_3$–$C_8$)-halocycloalksulfinyl, ($C_4$–$C_8$)-halocycloalkenylsulfinyl, ($C_1$–$C_6$)-alkylsulfonyl, ($C_2$–$C_6$)-alkenylsulfonyl, ($C_2$–$C_6$)-alkynylsulfonyl, ($C_1$–$C_6$)-haloalkylsulfonyl, ($C_2$–$C_6$)-haloalkenylsulfonyl, ($C_2$–$C_6$)-haloalkynylsulfonyl, ($C_3$–$C_8$)-cycloalkylsulfonyl, ($C_4$–$C_8$)-cycloalkenylsulfonyl, ($C_3$–$C_8$)-halocycloalkylsulfonyl, ($C_4$–$C_8$)-halocycloalkenylsulfonyl, ($C_1$–$C_6$)-alkylamino, ($C_2$–$C_6$)-alkenylamino, ($C_2$–$C_6$)-alkynylamino, ($C_1$–$C_6$)-haloalkylamino, ($C_2$–$C_6$)-haloalkenylamino, ($C_1$–$C_6$)-haloalkynylamino, ($C_3$–$C_8$)-cycloalkylamino, ($C_4$–$C_8$)-cycloalkenylamino, ($C_3$–$C_8$)-halocycloalkamino and ($C_4$–$C_8$)-halocycloalkenylamino;

$R^{11}$ is ($C_1$–$C_{10}$)-alkyl, haloalkyl, aryl, which is optionally substituted by one or more radicals from the group halogen, cyano, nitro, ($C_1$–$C_4$)-alkoxy, ($C_1$–$C_4$)-alkyl, amino, ($C_1$–$C_4$)-monoalkylamino and ($C_1$–$C_4$)-dialkylamino;

$NR^{10}_2$, $OR^{10}$ or $SR^{10}$ with the proviso that the compounds listed below are not included:

3-(2-chlorophenyl)-1-methyl-5-(4-trifluoromethyl-3-pyridyl)-1H-1,2,4-triazole 3-(2,6-difluorophenyl)-1-methyl-5-(4-trifluoromethyl-3-pyridyl)-1H-1,2,4-triazole 3-(2chloro4-fluorophenyl)-1-methyl-5-(4-trifluoromethyl-3-pyridyl)-1H-1,2,4-triazole 3-(3,5-dichlorophenyl)-5-(4-trifluoromethyl-3-pyridyl)-1,2,4-oxadiazole 5-(4-trifluoromethyl-3-pyridyl)-3-phenyl-1,2,4-oxadiazole 3-(4-trifluoromethyl-3-pyridyl)-5-phenyl-1,2,4-oxadiazole 5-(2-chlorophenyl)-3-(4-trifluoromethyl-3-pyridyl)-1,2,4-oxadiazole 5-(3-chlorophenyl)-3-(4-trifluoromethyl-3-pyridyl)-1,2,4-oxadiazole 5-(4-chlorophenyl)-3-(4-trifluoromethyl-3-pyridyl)-1,2,4-oxadiazole 5-(2-fluorophenyl)-3-(4-trifluoromethyl-3-pyridyl)-1,2,4-oxadiazole 5-(4-fluorophenyl)-3-(4-trifluoromethyl-3-pyridyl)-1,2,4-oxadiazole 5-(2,4-dichlorophenyl)-3-(4-trifluoromethyl-3-pyridyl)-1,2,4-oxadiazole 5-(3,4-dichlorophenyl)-3-(4-trifluoromethyl-3-pyridyl)-1,2,4-oxadiazole 5-(3,5ichlorophenyl)-3-(4-trifluoromethyl-3-pyridyl)-1,2,4-xadiazole 5-(2,6-dichloro4-pynidyl)-3-(4-trifluoromethyl-3-pyridyl)-1,2,4-oxadiazole 5-(3,5-bistrifluoromethylp heny l)-3- (4-trifluoromethyl-3-pyridyl)-1,2,4oxadiazo le 2-(2-chloro phenyl)-5-( 4-trifluoromethyl -3-pyridyl)-1,3,4-xadiazole 2-(3chlorophenyl)-5-(4-trifluoromethyl-3-pyridyl)-1,3,4-oxadiazole 2-(4-chlorophenyl)-5-(4-trifluoromethyl-3-pyridyl)-1,3,4-oxadiazole 2-(2-trfluoromethoxyphenyl)-5-(4-trifluoromethyl-3-pyridyl)-1,3,4-oxadiazo le 2-(4-trifluoromethoxyphenyl)-5-(4-trifluoromethyl-3-pyridyl)-1,3,4-oxadiazole 2-(4-trifluoromethyl-3-pyridyl)-5-phenyl-1,3,4-oxadiazole 2-(4-trifluoromethyl-3-pyridyl)4-methylthiazolecarbohydrazide ethyl 2-(4-trifluoromethyl-3-pyridyl)-4-methylthiazolecarboxylate N-(4-chlorophenyl)-carbonyl-N'-[2-(4-trifluoromethyl-3-pyridyl)4-methyl-5-thiazolyl]carbonylhydrazine 2-(4-trifluoromethyl-3-pyridyl)4-thiazolecarbohydrazide 4-(4-chlorophenyl)-2-(4-trifluoromethyl-3-pyridyl)thiazole 4-(4-yanophenyl)-2-(4-trifluoromethyl-3-pyridyl)thiazole N-(4-trifluoromethylphenyl)carbonyl—N'-[2-(4-trifluoromethyl-3-pyridyl)4-thiazolyl]carbonylhydrazine 2-(2-(4-trifluoromethyl-3-pyridyl)thiazolyi)-5chloro-3-methylbenzo[b]thiophene 2-(4-chlorophenylmethylthio)-5-(4-trifluoromethyl-3-pyridyl)-1-methyl-1H-1,3,4-triazole 2-(4-chlorophenylcarbonylmethylthio)-5-(4-trifluoromethyl-3-pyridyl)-1-methyl-1H-1,3,4-triazole and 2-ethoxycarbonylmethylthio-5-(4-trifluoromethyl-3-pyridyl)-1-methyl-1H-1,3,4-triazole.

2. A 4-haloalkyl-3-heterocyclylpyridine or 4-haloalkyl-5-heterocyclylpyrimidine as claimed in claim 1, wherein Y is $C_1$–$C_6$–alkyl which is mono- or polysubstituted by chlorine and/or fluorine;

m is zero;

Q is a 5-membered heterocyclic group

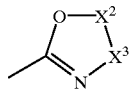

in which
a) $X^2$=$NR^a$ and $X^3$=$CR^bR^{10}$ or
b) $X^2$=$CR^aR^2$ and $X^3$=$CR^bR^3$ or
c) $X^2$=$CR^4R^5$ and $X^3$=$CR^6R^7$;

$R^a$ and $R^b$ together are a bond;

$R^1$, $R^2$, $R^3$, $R^4$ and $R^6$ are each independently of one another hydrogen, halogen, $C_1$–$C_{12}$-alkyl, $C_3$–$C_8$–cycloalkyl, $C_2$–$C_8$–alkenyl, $C_2$–$C_8$–alkynyl, where the four last-mentioned hydrocarbon radicals are optionally mono- or polysubstituted by identical or different radicals from a group A1 consisting of $C_1$–$C_6$–alkylcarbonyl, $C_1$–$C_6$–alkylaminocarbonyl, $C_1$–$C_6$–alkoxy, $C_1$–$C_6$–alkylthio, $C_1$–$C_6$–alkylamino, $C_1$–$C_6$–alkylcarbonylamino, $C_1$–$C_6$–alkylsulfonylamino, phenyl, furyl, pyrryl, thienyl, halogen, cyano, phenyloxy, phenylthio and phenylamino, where the eleven first-mentioned radicals of group A1 are each optionally mono- or polysubstituted by identical or different radicals from a group B1 consisting of halogen, cyano, $C_1$–$C_3$–alkoxy and phenyl which is optionally mono- or polysubstituted by one or more halogen atoms and where the three last-mentioned radicals of group A1 are each optionally mono- or polysubstituted by identical or different radicals from a group B2 consisting of halogen, cyano, nitro, $C_1$–$C_3$–alkyl and $C_1$–$C_3$–alkoxy, or are $C_1$–$C_6$–alkylcarbonyl, $C_1$–$C_6$–alkylaminocarbonyl, $C_1$–$C_6$–alkoxycarbonyl, phenyl, pyridyl, furyl, thienyl, pyrryl, where the eight last-mentioned radicals are optionally mono- or polysubstituted by identical or different radicals from group B1, or are $OR^{10}$, $SR^{10}$ or $N(R^{10})_2$;

$R^5$ and $R^7$ are each independently of one another hydrogen, halogen, $C_1$–$C_{12}$-alkyl, $C_3$–$C_8$cycloalkyl, $C_2$–$C_8$–alkenyl, $C_2$–$C_8$–alkynyl, where the four last-mentioned hydrocarbon radicals are optionally mono- or polysubstituted by identical or different radicals from a group A2 consisting of $C_1$–$C_6$–alkylcarbonyl, $C_1$–$C_6$–alkylaminocarbonyl, $C_1$–$C_6$–alkoxy, $C_1$–$C_6$–alkylthio, $C_1$–$C_6$–alkylamino, $C_1$–$C_6$–alkylcarbonylamino, phenyl, furyl, pyrryl, thienyl, halogen, cyano, phenyloxy, phenylthio and phenylamino, where the ten first-mentioned radicals of group A2 are each optionally mono- or polysubstituted by identical or different radicals from the group B1 and the three last-mentioned radicals of group A2 are each optionally mono- or polysubstituted by identical or different radicals from the group B2, or are $C_1$–$C_6$–alkylcarbonyl, $C_1$–$C_6$–alkylaminocarbonyl, $C_1$–$C_6$–alkoxycarbonyl, phenyl, pyridyl, furyl, thienyl, fluorine, chlorine, bromine, pyrryl, where the eight last-mentioned radicals are optionally mono- or polysubstituted by identical or different radicals from the group B1, or are $OR^{10}$, $SR^{10}$ or $N(R^{10})_2$;

$R^{10}$ is hydrogen, benzyl, $C_1$–$C_6$–alkyl, $C_1$–$C_6$–cycloalkyl, $C_2$–$C_6$–alkenyl, $C_2$–$C_6$–alkynyl, phenyl, $C_1$–$C_6$–alkylcarbonyl or $C_1$–$C_6$–alkylsulfonyl, where the eight last-mentioned radicals are optionally mono- or polysubstituted by identical or different halogen atoms.

3. A 4-haloalkyl-3-heterocyclylpyridine or 4-haloalkyl-5-heterocyclylpyrimidine as claimed in claim 1, wherein Y is trifluoromethyl;

$R^1$, $R^2$, $R^3$, $R^4$ and $R^6$ are each independently of one another halogen, $C_1$–$C_{12}$-alkyl, $C_2$–$C_{12}$-alkenyl, where the two last-mentioned radicals are optionally mono- or polysubstituted by identical or different radicals from a group A3 consisting of $C_1$–$C_4$–alkylcarbonyl, $C_1$–$C_4$–alkylaminocarbonyl, $C_1$–$C_4$–alkoxy, $C_1$–$C_4$–alkylthio, $C_1$–$C_4$–alkylamino, $C_1$–$C_4$–alkylcarbonylamino, $C_1$–$C_4$–alkylsulfonylamino, phenyl, furyl, pyrryl, thienyl, fluorine, chlorine, bromine, cyano, phenyloxy, phenylthio and phenylamino, where the eleven first-mentioned radicals of group A3 are each optionally mono- or polysubstituted by identical or different radicals from the group B1 and the three last-mentioned radicals of group A3 are each optionally mono- or polysubstituted by identical or different radicals from the group B2, or are $OR^{10}$, $SR^{10}$ or $N(R^{10})_2$;

$R^5$ and $R^7$ are each independently of one another halogen, $C_1$–$C_{12}$-alkyl, $C_2$–$C_{12}$-alkenyl, where the two last-mentioned radicals are optionally mono- or polysubstituted by identical or different radicals from a group A4 consisting of $C_1$–$C_4$–alkylcarbonyl, $C_1$–$C_4$–alkylaminocarbonyl, $C_1$–$C_4$–alkoxy, $C_1$–$C_4$–alkylthio, $C_1$–$C_4$–alkylamino, $C_1$–$C_4$–alkylcarbonylamino, phenyl, furyl, pyrryl, thienyl, fluorine, chlorine, bromine, cyano, phenyloxy, phenylthio and phenylamino, where the ten first-mentioned radicals of group A4 are each optionally mono- or polysubstituted by identical or different radicals from the group B1 and the three last-mentioned radicals of group A4 are each optionally mono- or polysubstituted by identical or different radicals from the group B2, or are $OR^{10}$, $SR^{10}$ or $N(R^{10})_2$;

$R^{10}$ is hydrogen, $C_1$–$C_6$–alkyl, $C_2$–$C_6$–alkenyl, $C_2$–$C_6$–alkynyl, phenyl, $C_1$–$C_4$–alkylcarbonyl or $C_1$–$C_4$–alkylsulfonyl, where the six last-mentioned radicals are optionally mono- or polysubstituted by identical or different halogen atoms.

4. A 4-haloalkyl-3-heterocyclylpyridine or 4-haloalkyl-5-heterocyclyl-pyrimidine as claimed in claim 1, wherein $R^1$, $R^2$, $R^3$ $R^4$ and $R^6$ are each independently of one another $C_1$–$C_{10}$-alkyl, $C_2$–$C_{10}$-alkenyl, where the two last-mentioned radicals are optionally mono- or polysubstituted by identical or different radicals from a group A5 consisting of $C_1$–$C_4$–alkylcarbonyl, $C_1$–$C_4$–alkylaminocarbonyl, $C_1$–$C_4$–alkoxy, $C_1$–$C_4$–alkylthio, $C_1$–$C_4$–alkylamino, $C_1$–$C_4$–alkylcarbonylamino, $C_1$–$C_4$–alkylsulfonylamino, phenyl, fluorine, chlorine, bromine, cyano, phenyloxy, phenylthio and phenylamino, where the eight first-mentioned radicals of group A5 are each optionally mono- or polysubstituted by identical or different radicals from the group B1 and the three last-mentioned radicals of group A5 are each optionally mono- or polysubstituted by identical or different radicals from the group B2;

$R^5$ and $R^7$ are each independently of one another $C_1$–$C_{10}$-alkyl, $C_2$–$C_{10}$-alkenyl, where the two last-mentioned radicals are optionally mono- or polysubstituted by identical or different radicals from a group A6 consisting of $C_1$-$C_4$-alkylcarbonyl, $C_1$-$C_4$-alkylaminocarbonyl, $C_1$-$C_4$-alkoxy, $C_1$-$C_4$-alkylthio, $C_1$-$C_4$-alkylamino, $C_1$-$C_4$-alkylcarbonylamino, phenyl, fluorine, chlorine, bromine, cyano, phenyloxy, phenylthio and phenylamino, where the seven first-mentioned radicals of group A6 are each optionally mono- or polysubstituted by identical or different radicals from the group B1 and the three last-mentioned radicals of group A6 are each optionally mono- or polysubstituted by identical or different radicals from the group B2.

5. A process for preparing compounds of the formula I as claimed in claim 1, which comprises reacting, if A) $X^1$=O, $X^2$=$NR^a$, $X^3$=$CR^bR^1$ activated derivatives of the acid of the formula (II),

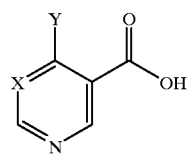

(II)

where X and Y are as defined above, in the presence of a base with a compound of the formula (III),

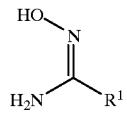

(III)

in which the radical $R^1$ is as defined in formula (I), or, if

B) $X^1$=S, $X^2$=$NR^a$, $X^3$=CR $R^1$ compounds of the formula (VII) with an electrophilic amination agent

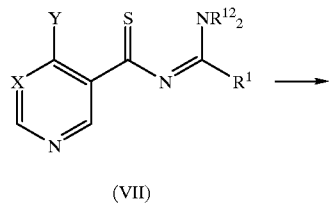

(VII)

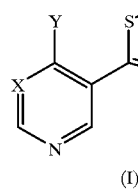

(I)

or, if

C) $X^1$=$NR^a$, $X^2$=$CR^bR_1$, $X^3$=O amidoximes of the formula (V) with activated derivatives of acids of the formula (VI) or with the acids of the formula (VI) themselves

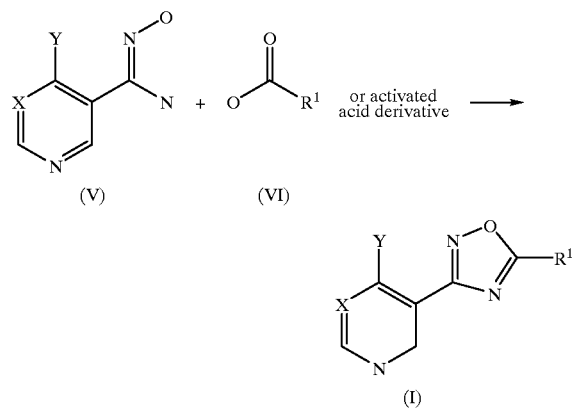

or, if

D) $X^1$=S, $X^2$=$CR^aR^1$, $X^3$=$NR^b$ N,N'-diacylhydrazines of the formula (XIII) with a thiolation agent, such as Lawessons reagent, in an inert solvent

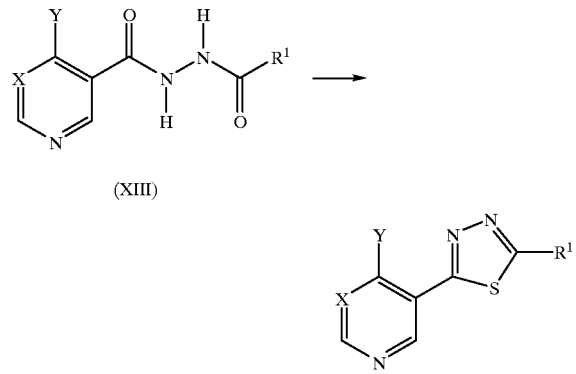

or, if

E) $X^1$=O, $X^2$=$CR^aR^1$, $X^3$=$NR^b$ acids of the formula (II) with hydrazides of the formula (X), in which $R^{10}$ is as defined above using an activating reagent, such as phosphorus oxychloride or phosphorus pentachloride,

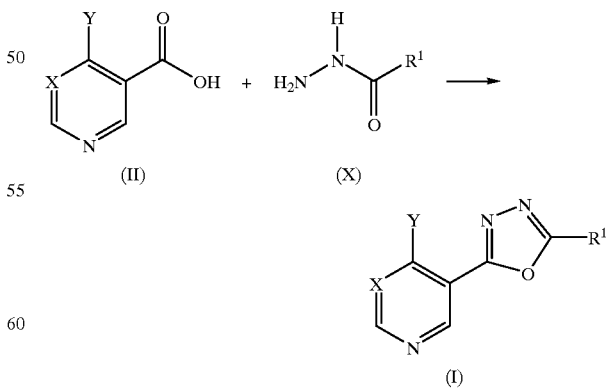

or acid hydrazides of the formula (XI) with orthoesters of the formula (XII), where $R^1$ is as defined above, and $R^{12}$ is ($C_1$-$C_4$)-alkyl

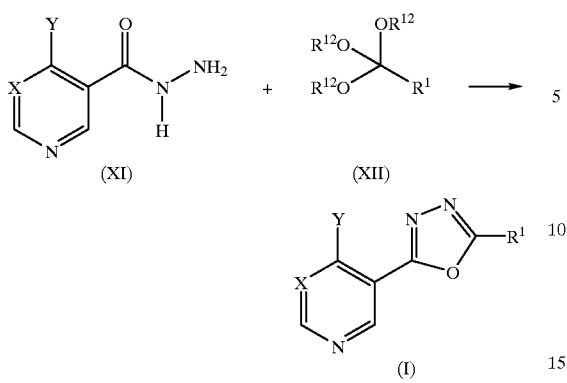

or, if

F) $X^1=O$, $X^2=CR^aR^2$, $X^3=CR^bR^3$ and $R^a$, $R^b$ and $R^3$ are as defined above, compounds of the formula (XIV) with a dehydrating reagent, such as inorganic acid chlorides, inorganic acids and anhydrides,

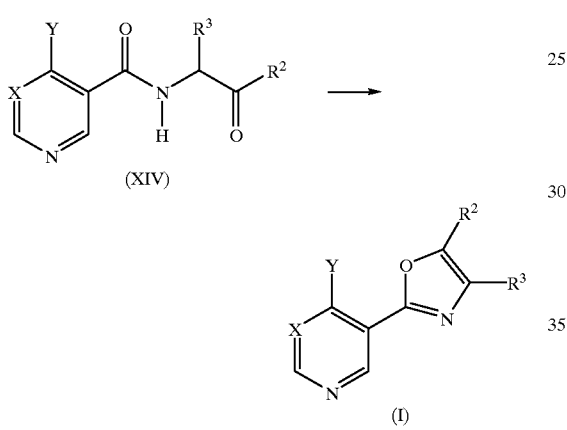

or, if

G) $X^1=S$, $X^2=CR^aR^2$, $X^3=CR^bR^3$ thioamides of the formula (XVII) with carbonyl derivatives of the formula (XVIII) where Z is halogen, in particular chlorine or bromine, acyloxy or sulfonyloxy, in particular methanesulfonyloxy or tolylsulfonyloxy

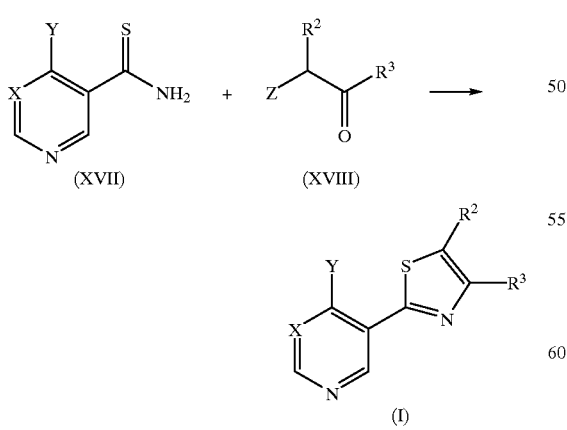

or, if

H) $X^1=S$, $X^2=CR^4R^5$, $X^3=CR^6R^7$ thioamides of the formula (XVII) with compounds of the formula (XIX)

where the two substituents Z are as defined above and may either be identical or different

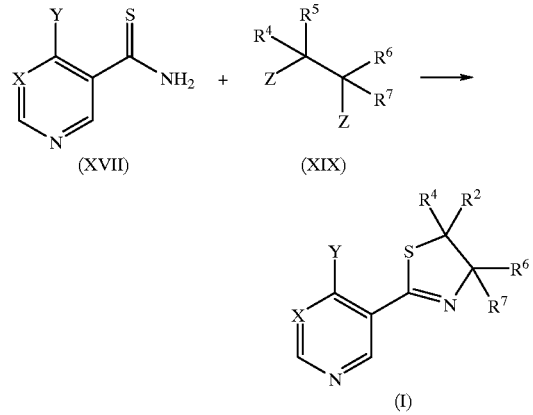

or, if

I) $X^1=NR^a$, $X^2=CR^bR^1$, $X^3=NR^8$ and $R^a$, $R^b$, $R^1$ and $R^8$ are as defined above, hydrazides of the formula (XX)

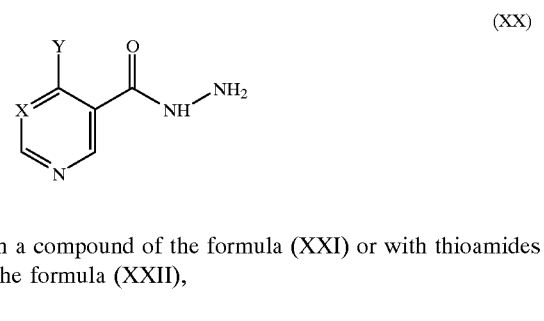

with a compound of the formula (XXI) or with thioamides of the formula (XXII),

6. A composition having insecticidal, acaricidal and/or nematicidal action, comprising an effective amount of at least one compound as claimed in claim 1.

7. The composition according to claim 6, further comprising carriers and/or surfactants.

8. The composition according to claim 6, further comprising an effective amount of a further active compound selected from the group consisting of acaricides, fungicides, herbicides, insecticides, nematicides and growth-regulating substances.

9. A veterinary formulation, comprising a compound as claimed in claim 1 or a composition as claimed in claim 6, and a veterinarily acceptable carrier and/or surfactant.

10. The veterinary formulation according to claim 9, wherein said formulation controls endo- and ectoparasites.

11. A method for controlling harmful insects, acarina and nematodes, which comprises applying an effective amount of a compound as claimed in claim 1 or of a composition as claimed in claim 6 to the area where the action is desired.

12. A process for protecting useful plants against the undesired action of harmful insects, acarina and nematodes, which comprises using at least one of the compounds as claimed in claim 1 for treating the seed of the useful plants.

* * * * *